US007201899B2

(12) United States Patent
d'Apice et al.

(10) Patent No.: US 7,201,899 B2
(45) Date of Patent: Apr. 10, 2007

(54) MATERIALS AND METHODS FOR MANAGEMENT OF HYPERACUTE REJECTION IN HUMAN XENOTRANSPLANTATION

(75) Inventors: Anthony J. F. d'Apice, Balwyn (AU); Martin J. Pearse, Mordialloc (AU); Allan J. Robins, Waterloo Corner (AU); Robert J. Crawford, West Lake Shores (AU); Peter D. Rathjen, Blackwood (AU)

(73) Assignees: BresaGen Limited, Thebarton SA (AU); St. Vincent's Hospital, Victoria (AU)

( * ) Notice: Subject to any disclaimer, the term of this patent is extended or adjusted under 35 U.S.C. 154(b) by 366 days.

(21) Appl. No.: 10/762,888

(22) Filed: Jan. 21, 2004

(65) Prior Publication Data

US 2004/0171155 A1    Sep. 2, 2004

Related U.S. Application Data

(60) Continuation of application No. 08/984,900, filed on Dec. 4, 1997, now Pat. No. 6,849,448, which is a division of application No. 08/378,617, filed on Jan. 26, 1995, now Pat. No. 5,849,991, which is a continuation-in-part of application No. 08/188,607, filed on Jan. 27, 1994, now abandoned.

(51) Int. Cl.
*A01N 63/00* (2006.01)
*C12N 15/00* (2006.01)
*C12N 15/63* (2006.01)
*C12N 15/87* (2006.01)
*C07H 21/04* (2006.01)

(52) U.S. Cl. .............................. 424/93.21; 435/320.1; 435/455; 435/463; 536/23.1; 536/23.5

(58) Field of Classification Search ............. 424/93.21; 435/320.1, 455, 463; 536/23.1, 23.5
See application file for complete search history.

(56) References Cited

FOREIGN PATENT DOCUMENTS

| AU | PL 7854 | 10/1994 |
|---|---|---|
| CA | 2011784 | 3/1990 |
| CA | 2157659 | 9/1994 |
| EP | 235805 | 9/1987 |
| WO | WO 88/07548 | 10/1988 |
| WO | WO 90/03432 | 4/1990 |
| WO | WO 90/08188 | 7/1990 |
| WO | WO 91/13985 | 9/1991 |
| WO | WO 91/19796 | 12/1991 |
| WO | WO 92/07581 | 5/1992 |
| WO | WO 93/16729 | 9/1993 |
| WO | WO 94/02616 | 2/1994 |
| WO | WO 94/21799 | 9/1994 |

OTHER PUBLICATIONS

Verma et al., Sep. 1997, Nature, vol. 389, pp. 239-242.*
Eck et al., 1996, Goodman & Gilman's The Pharmacological Basis of Therapeutics, McGraw-Hill, New York, p. 77-101.*
Gorecki, 2001, Expert Opin. Emerging Drugs, 6(2): 187-198.*
GenBank Nucleotide Sequence Access No. NCBI: J04989, deposited Apr. 27, 1993.
GenBank Nucleotide Sequence Access No. NCBI: X12810, deposited Mar. 31, 1995.
GenBank Nucleotide Sequence Access No. NCBI: X13967, deposited Sep. 9, 2004.
Abstracts from the 2nd International Congress on Xenotransplantation, Cambridge, England, Sep. 26-29, 1993.
Abstracts from 11th Meeting of Transplant Society of Australia and New Zealand, Australia, May 5-7, 1993.
Letter to Examiner disclosing grounds for an opposition filed by the Austin Research Institute in corresponding Australian patent application No. 711,144 (2 pages).
Fournier et al., "A Human Naturally Occurring Antibody, Anti-Gal, Recognises Epitopes in Pig Kidney, Heart and Liver and is Cytotoxic to Endothelial Cells in the Presence of Rabbit Complement," Abstract, #113, p. 142, Second International Congress on Xenotransplantation held in Cambridge, England Sep. 26-29, 1993.
Dabkowski et al., "Isolation of a cDNA Clone Encoding the Pig $\alpha$1,3 Galactosyltransferase," Transplantation Proceedings 26(3):1335, 1994.
Cooper et al., "Genetically engineered pigs," The Lancet 342:682-683, 1993.
Hogan et al., "Getting nearer the mark," Nature 336:304-305, 1988.
Mansour et al., "Disruption of the proto-oncogene int-2 in mouse embryo-derived stem cells: a general strategy for targeting mutations to non-selectable genes," Nature 336:348-352, 1988.
O'Gorman et al., "Recombinase-Mediated Gene Activation and Site-Specific Integration in Mammalian Cells," Science 251:1351-1355, 1991.
Capecchi, "Tapping the cellular telephone," Nature 344:10, 1990.
Alberts et al., (eds.) *Molecular Biology of the Cell*, Garland Publishing, Inc.: New York and London, 1989, pp. 194, 195, 894-896, 900, 901.

(Continued)

Primary Examiner—Shin-Lin Chen
(74) Attorney, Agent, or Firm—Fish & Richardson, P.C.

(57) ABSTRACT

Human pre-formed xenoantibodies play an important role in the hyperacute rejection response in human xenotransplantation. Disclosed are materials and methods for removing or neutralizing such antibodies. Also disclosed are materials and methods for reducing or eliminating the epitopes in the donor organs that are recognized by such antibodies. Such epitopes are formed as the result of activity by the enzyme $\alpha$-1,3 galactosyltransferase. The porcine gene encoding $\alpha$-1,3 galactosyltransferase is disclosed, as are materials and methods for inactivating ("knocking out") the $\alpha$-1,3 galactosyltransferase gene in mammalian cells and embryos. Included are nucleic acid constructs useful for inactivating the $\alpha$-1,3 galactosyltransferase gene in a target cell. Also disclosed is a novel leukemia inhibitory factor (T-LIF) that is useful for maintenance of embryonic stem cells and primordial germ cells in culture.

10 Claims, 42 Drawing Sheets

OTHER PUBLICATIONS

Sandrin et al., "Studies on Human Naturally Occurring Antibodies to Pig Xenografts," Transplantation Proceedings, 25(5):2917-2918, 1993.
Vaughan et al., "Biochemical Analysis of Pig Xenoantigens Detected by Human Antibodies," Transplantation Proceedings 25(5):2919-2920, 1993.
Mortensen, "Double Knockouts: Production of Mutant Cell lines in Cardiovascular Research," Hypertension 22:646-651, 1993.
Robertson, "Embryo-derived stem cell lines," In *Teratocarcinomas and embryonic stem cells: a practical approach*, E.J. Robertson (ed.), IRL Press: Oxford, England, 1987, Chapter 4.
Zijlstra et al., "Germ-line transmission of a disrupted B2-microglobulin gene produced by homologous recombination in embryonic stem cells," Nature 342:435-438, 1989.
Merlino, "Transgenic animals in biomedical research," FASEB J. 5:2996-3001, 1991.
Broach et al., "Replication and Recombination Functions Associated with the Yeast Plasmid, 2µ Circle," Cell 21:501-508, 1980.
Thall et al., "Oocyte Galα1,3Gal Epitopes Implicated in Sperm Adhesion to the Zona Pellucida Glycoprotein ZP3 Are Not Required for Fertilization in the Mouse," The Journal of Biological Chemistry 270(37):21437-21440, 1995.
Tearle et al., "The α-1,3-Galactosyltransferase Knockout Mouse," Transplantation 61:13-19, 1996.
McKenzie et al., "Human Lymphocytotoxic and Haemagglutinating Activity Against Sheep and Pig Cells," The Lancet, Aug. 17, 1968, 386-387.
Galili et al., "A Unique Natural Human IgG Antibody with Anti-α-Galactosyl Specificity," J. Exp. Med. 160:1519-1531, 1984.
Cosgrove et al., "Mice Lacking MHC Class II Molecules," Cell 66:1051-1066, 1991.
Sandrin et al., *Proc. Natl. Acad. Sci. USA*, 90:11391-11395 (1993).
Liu et al., *Int. J. Dev. Biol.*, 39:639-644 (1995).
Matsui et al., *Cell*, 70:841-847 (1992).
Sandrin et al., *Immunological Reviews*, 141:169-190 (1994).
Gustafsson et al., *Immunological Reviews*, 141:59-70 (1994).
Galili, *Immunology Today*, 14:480-482 (1993).
Larsen et al, *Proc. Natl. Acad. Sci. USA*, 86:8227-8231 (1989).
Fletcher et al., *J. of Exp. Medicine*, 174:837-845 (1991).
Samal et al., *Biochimica et Biophysica Acta*, 1260:27-34 (1995).
Willson et al., *European J. of Biochem.*, 204:21-30 (1992).
Gough et al. *Proc. Natl. Acad. Sci.*, 85:2623-2627 (1988).
Gearing et al., *Nucleic Acids Res.*, 16:9857 (1988).
Moreau et al., *Nature*, 336:690-692 (1988).
Gearing et al., *Bio/Technology*, 7:1157-1161 (1989).
Yamamori et al., *Science*, 246:1412-1416 (1989).
Lowe et al., *DNA*, 8:351-359 (1989).
Stahl et al., *J. Biol. Chem.*, 265:8833-8841 (1990).
Vaughan et al., *Transplantation*, 58:879-882 (1994).
Latinne et al., *Immunological Reviews*, 141:95-125 (1994).
Soares et al., *Transplantation*, 57:1003-1009 (1994).
Soares et al., *Transplantation*, 56:1427-1433 (1993).
Gambiez et al., *Transplantation*, 54:577-583 (1992).
Oriol et al., *Transplant Internationa*, 7:405-413 (1994).
Hale et al., *Blood*, 62:873-882 (1983).
Dabkowski et al., *Transplant. Proc.*, 25:2921 (1993).
Paulson et al., *J. Biol. Chem.*, 264:17615-17618 (1989).
Joziasse et al., *J. Biol. Chem.*, 267:5534-5541 (1992).
Thomas et al., *Cell*, 51:503-512 (1987).
Capecchi, *Trends in Genetics*, 5:70-76 (1989).
Jung et al., *Science*, 259:984-987 (1993).
Joziasse et al., *J. Biol. Chem.*, 264:14290-14297 (1989).
Brinster et al., *Proc. Nat. Acad. Sci. USA*, 86:7087-7091 (1989).
Rathjen et al., *Cell*, 62:1105-1114 (1990).
Galili, *The Lancet*, pp. 358-360, Aug. 12, 1989.
Thall et al., *Autoimmunity*, 10:81-87 (1991).
Good et al., *Transplant. Proc.*, 24:559-62 (1992).
Galili, *Springer Sem. Immunopathol.*, 15:155-71 (1993).
Galili, *Xeno*, 2:84-87 (1994).
Resnick et al., *Nature*, 359:550-551 (1992).
Capecchi, M.R., (ed.), *Molecular Genetics of Early Drosophilia and Mouse Development* pp. 39-44 (Cold Springs Harbor Lab. Press, 1989).
Jaenisch, R., *Science*, 240:1468-1474 (1988).
Laus, et al., *Int. Archs Allergy Appl. Immun.*, 85:201-207 (1988).
Hendricks, S.P., et al., *J. Bio. Chem.*, 265:17621-17626 (1990).
Platt, J.L., et al., *Transplantation*, 50:817-822 (1990).
Galili, U., et al., *J. Bio. Chem.*, 263:17755-17762 (1988).
Smith, D.F., et al., *J. Fed. Am. Soc. Exp. Biol.*, 4:A1979 (1990).
Hindsgaul, D., et al., *J. Bio. Chem.*, 266:17858-17862 (1991).
Cooper, D.K.C., et al., *Transplantation Proceedings*, 24:566-571 (1992).
Cooper, D.K.C., et al., *Xeno-transplantation*, pp. 47-99, 170-178, 312-321, 429-438, 500-510, (Springer-Verlag Berlin Heidelberg, 1991).
Platt, J.L., et al., *Immunology*, 3:735-739 (1991).
Miyagawa, S., et al., *Transplantation Proceedngs*, 21:520-521 (1989).
Platt, J.L., et al., *Immunology Today*, 11:450-456 (1990).
Ware, C.B., et al., *Biology of Reproduction (Supplement)*, 38:129 (1988).
Piedrahita, J.A., *Theriogenology*, 29:286 (1988).
Thompson, S., et al., *Cell*, 56:313-321 (1989).
Zimmer, A., et al., *Nature*, 338:150-153 (1989).
Capecchi, M.R., *Science*, 244:1288-1292 (1989).
Kidd, V.J., et al., *J. Cell Biochem. (Suppl.)*, p. 200 (1988).

* cited by examiner

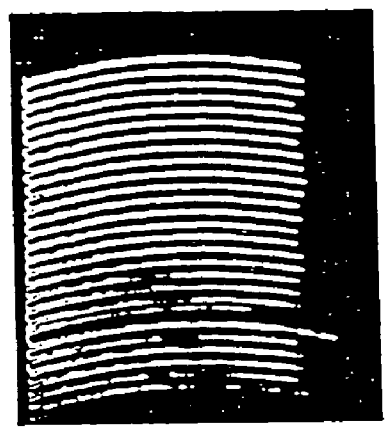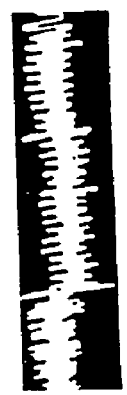
13% plasma
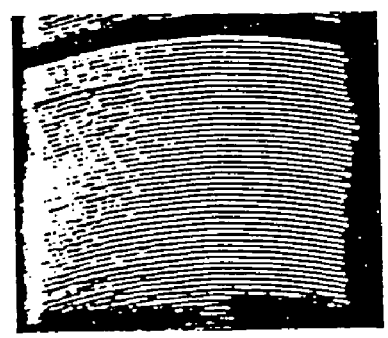
5 % plasma
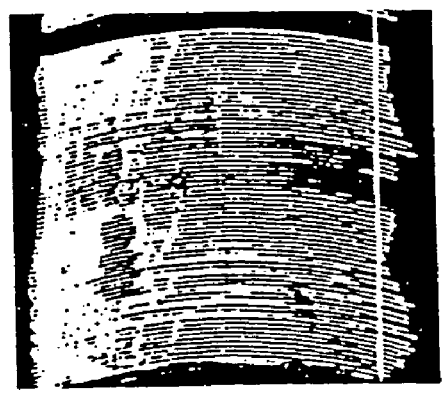
10mM Melibiose
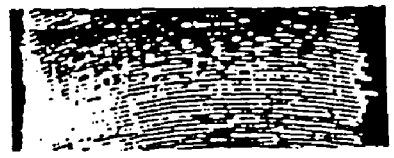
Baseline
FIG. 3

| | | | | | | | |
|---|---|---|---|---|---|---|---|
| PGTCD | 1 | ---------- | ---------- | ---------- | ---------- | ---------- | 50 |
| BOVGSTA | 1 | CCGGGGGCCG | GGCCGAGCTG | GGAGCGTCGA | GCCCGCTGCC | CAGCGCCCGC | 50 |
| MUSGLYTNS | 1 | ---------- | ---------- | ---------- | ---------- | ---------- | 50 |
| | | | | | | | |
| PGTCD | 51 | ---------- | ---------- | ---------- | ---------- | ---------- | 100 |
| BOVGSTA | 51 | CGGCTCCCTC | GCGCCCCTGC | CCGCCGCCCC | GGAGGAGCGC | CCGGCGGGCCG | 100 |
| MUSGLYTNS | 51 | ---------- | ---------- | ---------- | ---------- | ---------- | 100 |
| | | | | | | | |
| PGTCD | 101 | ---------- | ---------- | ---------- | ---------- | ---------- | 150 |
| BOVGSTA | 101 | GCCGACGGGA | GCGCAGCGGC | ACACCCCGCC | CCGGCACGCC | CGGCGGGGCTC | 150 |
| MUSGLYTNS | 101 | ---------- | ---------- | ---------- | ---------- | ---------- | 150 |
| | | | | | | | |
| PGTCD | 151 | ---------- | ---------- | ---------- | ---------- | ---------- | 200 |
| BOVGSTA | 151 | GGGAGGAGGC | AGCGCGGCCGA | CTGTTCCGGC | AGCCGAGGAC | GCCGCCGGGG | 200 |
| MUSGLYTNS | 151 | ---------- | ---------- | ---------- | ---------- | ---------- | 200 |
| | | | | | | | |
| PGTCD | 201 | ---------- | ---------- | ---------- | ---------- | ---------- | 250 |
| BOVGSTA | 201 | AGCCGAGGCG | CCGGCCAGCC | CCCAGCCGCG | CCAGCTTCTG | CGGATCAGGG | 250 |
| MUSGLYTNS | 201 | ------CG | TCTTAGGAGG | CTGGAGATTC | TGGGTGGAGC | CCTAGCCCTG | 250 |
| | | | | | | | |
| PGTCD | 251 | ---------- | ---------- | ---------- | ---------- | ---------- | 300 |
| BOVGSTA | 251 | AAACCACGTG | TCCTCAAGTG | GCCAGCCAGC | TGTCCCCAAG | AGGAACTTGC | 300 |
| MUSGLYTNS | 251 | CCTTTTCTTA | GCTGGCTGAC | ACCTTCCCTT | GTAGACTCTT | CTTGGAATGA | 300 |
| | | | | | | | |
| PGTCD | 301 | ---------- | ---------- | ---------- | ---------- | ---------- | 350 |
| BOVGSTA | 301 | CTGGCATTTG | CACGGAAAGA | CGAGACACTT | CACAAAATCA | ACGGAGTCAG | 350 |
| MUSGLYTNS | 301 | GAAGTACCGA | TTCTGCTGAA | GACCTCGCGC | TCTCAGGCTC | TGGGAGTTGG | 350 |

Exon 1 ←|→ Exon 2

FIG.4A

| | | | | | |
|---|---|---|---|---|---|
| PGTCD | 351 | ---------- | ---------- | ------AGC | CCTGCCTCCT TCTGCAGAGC | 400 |
| BOVGSTA | 351 | AAGGCTGCAC | CTTCGCTTCC | TCCC---AGC | CCTGCCTCCT TCTGCAGAAC | 400 |
| MUSGLYTNS | 351 | AACCCTGTAC | CTTCCTTTCC | TCTGCTGAGC | CCTGCCTCCT TCGGCAGGCC | 400 |

| | | | | | |
|---|---|---|---|---|---|
| PGTCD | 401 | AGAGCTCACT | AGAACTT-GT | TTC----GCC | TTTTACTCTG GGGGGAGAGA | 450 |
| BOVGSTA | 401 | GGAGCTCAGT | AGAACTT-GG | TACTTTTGCC | TTTTACTCTA GGAGGAGAGA | 450 |
| MUSGLYTNS | 401 | AGAGCTCGAC | AGAAGCTCGG | TTGCTTTGCT | GTTTGCTTTG GAGGAACAC | 450 |

Exon 2 ↓↑ Exon 3

| | | | | | |
|---|---|---|---|---|---|
| PGTCD | 451 | AGCAGAGGAT | GAG------- | ---------- | ---------- | 500 |
| BOVGSTA | 451 | AGCAGACGAT | GAG------- | ---------- | ---------- | 500 |
| MUSGLYTNS | 451 | AGCTGACGAT | GAGGCTGACT | TTGAACTCAA GAGATCTGCT | TACCCCAGTC | 500 |

| | | | | | |
|---|---|---|---|---|---|
| PGTCD | 501 | ---------- | ---------- | ---------- | ---------- | 550 |
| BOVGSTA | 501 | ---------- | ---------- | ---------- | ---------- | 550 |
| MUSGLYTNS | 501 | TCCTGGAATT | AAAGGCCTGT ACTACCTGC | CTGGACCTAA | GATTTTCATG | 550 |

| | | | | | |
|---|---|---|---|---|---|
| PGTCD | 551 | ---------- | ---------- | ---------- | ---------- | 600 |
| BOVGSTA | 551 | ---------- | ---------- | ---------- | ---------- | 600 |
| MUSGLYTNS | 551 | ATCACTATGC | TTCAAGATCT | CCATGTCAAC AAGATCTCCA | TGTCAAGATC | 600 |

Exon 3 ↓↑ Exon 4

| | | | | | |
|---|---|---|---|---|---|
| PGTCD | 601 | ---------- | ---------- | ---------- | ----GAGAAAA | 650 |
| BOVGSTA | 601 | ---------- | ---------- | ---------- | ---GAGAAAA | 650 |
| MUSGLYTNS | 601 | CAAGTCAGAA | ACAAGTCTTC | CATCCTCAAG ATCTGGATCA | CAGGAGAAAA | 650 |

| | | | | | |
|---|---|---|---|---|---|
| PGTCD | 651 | TAATGAATGT | CAAAGGAAGA | GTGGTTCTGT | CAATGCTGCT TGTCTCAACT | 700 |
| BOVGSTA | 651 | TAATGAATGT | CAAAGGAAAA | GTGATTCTGT | CAATGCTGGT TGTCTCAACT | 700 |
| MUSGLYTNS | 651 | TAATGAATGT | CAAGGAAAA | GTAATCCTGT | TGATGCTGAT TGTCTCAACC | 700 |

Start

FIG.4B

|         |      |              |              | Exon 4↓↑Exon 5 |              |              |      |
|---------|------|--------------|--------------|----------------|--------------|--------------|------|
| PGTCD   | 701  | GTAATGGTTG   | TGTTTTGGGA   | ATACATCAAC     | AGCCCAGAAG   | GTTCTTTGTT   | 750  |
| BOVGSTA | 701  | GTCATTGTTG   | TGTTTTGGGA   | ATATATCCAC     | AGCCCAGAAG   | GCTCTTTGTT   | 750  |
| MUSGLYTNS | 701 | GTGGTTGTCG  | TGTTTTGGGA   | ATATGTCAAC     | AGCCCAGACG   | GCTCTTTCTT   | 750  |

Exon 5↓↑Exon 6

| PGTCD   | 751  | CTGGATATAC   | CAGTCAAAAA   | ACCCAGAAGT     | TGGCAGCAGT   | GCTCAGAGGG   | 800  |
| BOVGSTA | 751  | CTGGATAAAC   | CCATCAAGAA   | ACCCAGAAGT     | TGGTGGCAGC   | AGCATTCAGA   | 800  |
| MUSGLYTNS | 751 | GTGGATATAT  | CACACAAAAA   | TTCCAGAGGT     | TGGTGAGAAC   | AGATGGCAGA   | 800  |

Exon 6↓↑Exon 7

| PGTCD   | 801  | GCTGGTGG--   | -TTTCCGAGC   | TGGTTAACA      | ATGGGACTCA   | CAGTTACCAC   | 850  |
| BOVGSTA | 801  | AGGGCTGGTG   | GCTTCCGAGA   | TGGTTTAACA     | ATG-------   | --GTTACCAT   | 850  |
| MUSGLYTNS | 801 | AGGACTGGTG  | GTTCCCAAGC   | TGGTTTAAAA     | ATGGGACCCA   | CAGTTATCAA   | 850  |

Exon 7↓↑Exon 8

| PGTCD   | 851  | GAAGAAGAAG   | ACGCTATAGG   | CAACGAAAAG     | GAACAAAGAA   | AAGAAGACAA   | 900  |
| BOVGSTA | 851  | GAAGAAGATG   | GAGACATAAA   | CGAAGAAAAG     | GAACAAAGAA   | ACGAAGACGA   | 900  |
| MUSGLYTNS | 851 | GAAGACAACG  | TAGAAGGACG   | GAGAGAAAAG     | GGTAGAAATG   | GAGATCGCAT   | 900  |

| PGTCD   | 901  | CAGAGGAGAG   | CTTCCGCTAG   | TGGACTGGTT     | TAATCCTGAG   | AAACGCCCAG   | 950  |
| BOVGSTA | 901  | ---AAGCAAG   | CTTAAGCTAT   | CGGACTGGTT     | CAACCCATTT   | AAACGCCCCG   | 950  |
| MUSGLYTNS | 901 | ---TGAAGAG  | CCTCAGCTAT   | GGGACTGGTT     | CAATCCAAAG   | AACCGCCCGG   | 950  |

| PGTCD   | 951  | AGTCGTGAC    | CATAACCAGA   | TGGAAGGCTC     | CAGTGGTATG   | GGAAGGCACT   | 1000 |
| BOVGSTA | 951  | AGTTGTGAC    | CATGACGAAG   | TGGAAGGCTC     | CAGTGGTGTG   | GGAAGGCACT   | 1000 |
| MUSGLYTNS | 951 | ATGTTTTGAC  | AGTGACCCCG   | TGGAAGGCGC     | CGATTGTGTG   | GGAAGGCACT   | 1000 |

| PGTCD   | 1001 | TACAACAGAG   | TAATTATTAT   | GCCAAACAGA     | AAATTACCGT   | 1050 |
| BOVGSTA | 1001 | TACAACAGAG   | CAATTATTAT   | GCCAAGCAGA     | AAATTACCGT   | 1050 |
| MUSGLYTNS | 1001 | CTCTGCTGGA  | AAAGTACTAC   | GCCACACAGA     | AACTCACTGT   | 1050 |

FIG.4C

```
                        Exon 8 ←→ Exon 9
PGTCD    1051 GGGCTTGACG GTTTTTGCTG TCGGAAGATA CATTGAGCAT TACTTGGAGG 1100
BOVGSTA  1051 CGGCCTGACG GTTTTCGCCG TCGGAAGATA CATTGAGCAT TACTTGGAGG 1100
MUSGLYTNS 1051 GGGGCTGACA GTGTTTGCTG TGGGAAAGTA CATTGAGCAT TACTTAGAAG 1100

PGTCD    1101 AGTTCTTAAT ATCTGCAAAT ACATACTTCA TGGTTGGCCA CAAAGTCATC 1150
BOVGSTA  1101 AGTTCTTAAC GTCTGCTAAT AAGCACTTCA TGGTGGGCCA CCCAGTCATC 1150
MUSGLYTNS 1101 ACTTTCTGGA GTCTGCTGAC ATGTACTTCA TGGTTGGCCA TCGGGTCATA 1150

PGTCD    1151 TTTTACATCA TGGTGGATGA TATCTCCAGG ATGCCTTTGA TAGAGCTGGG 1200
BOVGSTA  1151 TTTTATATCA TGGTAGATGA TGTCTCCAGG ATGCCTTTGA TAGAGTTGGG 1200
MUSGLYTNS 1151 TTTTACGTCA TGATAGATGA CACCTCCCGG ATGCCTGTCG TGCACCTGAA 1200

PGTCD    1201 TCCTCTGCGT TCCTTTAAAG TGTTTGAGAT CAAGTCCGAG AAGAGGTGGC 1250
BOVGSTA  1201 TCCTCTGCGC TCCTTCAAAG TGTTTAAGAT CAAGCCTGAG AAGAGGTGGC 1250
MUSGLYTNS 1201 CCCTCTACAT TCCTTACAAG TCTTTGAGAT CAGGTTCTGAG AAGAGGTGGC 1250

PGTCD    1251 AAGACATCAG CATGATGCGC ATGAAGACCA TCGGGGAGCA CATCCTGGCC 1300
BOVGSTA  1251 AGGACATCAG CATGATGCGC ATGAAGACTA TCGGGGAGCA CATTGTGGCC 1300
MUSGLYTNS 1251 AGGATATCAG CATGATGCGC ATGAAGACCA TTGGGGAGCA CATCCTGGCC 1300

PGTCD    1301 CACATCCAGC ACGAGGTGGA CTTCCTCTTC TGCATGGACG TGGATCAGGT 1350
BOVGSTA  1301 CACATCCAGC ATGAGGTTGA CTTCCTTTTC TGCATGGATG TGGACCAGGT 1350
MUSGLYTNS 1301 CACATCCAGC ACGAGGTCGA CTTCCTCTTC TGCATGGACG TGGATCAAGT 1350

PGTCD    1351 CTTCCAAAAC AACTTTGGGG TGGAGACCCT GGGCCAGTCG GTGGCTCAGC 1400
BOVGSTA  1351 CTTCCAAGAC AAGTTTGGGG TGGAGACCCT GGGCGAGTCG GTGGCCCAGC 1400
MUSGLYTNS 1351 CTTTCAAGAC AACTTCGGGG TGGAAACTCT GGGCCAGCTG GTAGCACAGC 1400
```

FIG. 4D

| | | | | | | | |
|---|---|---|---|---|---|---|---|
| PGTCD | 1401 | TACAGGCCTG | GTGGTACAAG | GCACATCCTG | ACGAGTTCAC | CTACGAGAGG | 1450 |
| BOVGSTA | 1401 | TACAAGCCTG | GTGGTACAAG | GCAGATCCCA | ATGACTTCAC | CTACGAGAGG | 1450 |
| MUSGLYTNS | 1401 | TCCAGGCCTG | GTGGTACAAG | GCCAGTCCCG | AGAAGTTCAC | CTATGAGAGG | 1450 |
| PGTCD | 1451 | CGGAAGGAGT | CCGCAGCCTA | CATTCCGTTT | GGCCAGGGGG | ATTTTTATTA | 1500 |
| BOVGSTA | 1451 | CGGAAGGAGT | CTGCAGCATA | CATTCCCCTTC | GGCGAAGGGG | ATTTTTATTA | 1500 |
| MUSGLYTNS | 1451 | CGGGAACTGT | CGGCCGCGTA | CATTCCATTC | GGAGAGGGGG | ATTTTTACTA | 1500 |
| PGTCD | 1501 | CCACGCAGCC | ATTTTTGGGG | GAACACCCAC | TCAGGTTCTA | AACATCACTC | 1550 |
| BOVGSTA | 1501 | CCATGCAGCC | ATTTTTGGGG | GAACACCCAC | TCAGGTCCTT | AACATCACCC | 1550 |
| MUSGLYTNS | 1501 | CCACGCGGCC | ATTTTTGGAG | GAACGCCTAC | TCACATTCTC | AACCTCACCA | 1550 |
| PGTCD | 1551 | AGGAGTGCTT | CAAGGGAATC | CTCCAGGACA | AGGAAAATGA | CATAGAAGCC | 1600 |
| BOVGSTA | 1551 | AGGAATGCTT | CAAAGGAATC | CTCAAGGACA | AGAAAAATGA | CATAGAAGCC | 1600 |
| MUSGLYTNS | 1551 | GGGAGTGCTT | TAAGGGGATC | CTCCAGGACA | AGAAACATGA | CATAGAAGCC | 1600 |
| PGTCD | 1601 | GAGTGGCATG | ATGAAAGCCA | TCTAAACAAG | TATTTCCTTC | TCAACAAACC | 1650 |
| BOVGSTA | 1601 | CAATGGCATG | ATGAAAGCCA | TCTAAACAAG | TATTTCCTTC | TCAACAAACC | 1650 |
| MUSGLYTNS | 1601 | CAGTGGCATG | ATGAGAGCCA | CCCTCAACAA | TACTTCCTTT | TCAACAAACC | 1650 |
| PGTCD | 1651 | CACTAAAATC | TTATCCCCAG | AATACTGCTG | GGATTATCAT | ATAGGCATGT | 1700 |
| BOVGSTA | 1651 | TACTAAAATC | TTATCCCCGG | AATACTGCTG | GGATTATCAC | ATAGGCCTAC | 1700 |
| MUSGLYTNS | 1651 | CACTAAAATC | CTATCTCCAG | AGTATTGCTG | GGACTATCAG | ATAGGCCTGC | 1700 |
| PGTCD | 1701 | CTGTGGATAT | TAGGATTGTC | AAGATAGCTT | GGCAGAAAAA | AGAGTATAAT | 1750 |
| BOVGSTA | 1701 | CTGCGGATAT | TAAGCTTGTC | AAGATGTCTT | GGCAGACAAA | AGAGTATAAT | 1750 |
| MUSGLYTNS | 1701 | CTTCAGATAT | TAAAAGTGTC | AAGGTAGCTT | GGCAGACAAA | AGAGTATAAT | 1750 |

```
PGTCD      1751 TTGGTTAGAA ATAACAT|TG A|CTTTAAATT GTGCCAGCAG TTTTCTGAAT 1800
BOVGSTA    1751 GTGGTTAGAA ATAATGT|TG A|CTT-----T GTGCCAGTAC ATTTCTGAAT 1800
MUSGLYTNS  1751 TTGGTTAGAA ATAATGT|TG A|CTTCAAATT GTG--------ATGGAAAC 1800
                                   Stop PGTCD      1801 TTGAAAGAGT ATTACTCTGG CTACTTCCTC AGAGAAGTAG ---CACTTAA 1850
BOVGSTA    1801 TTGAGAGAGT ATTATTCTGG CTACTTCCTC AGAAAAGTAA ---CACTTAA 1850
MUSGLYTNS  1801 TTGACAC--T ATTACTCTGG CTAATTCCTC AAACAAGTAG CAACACTTGA 1850

PGTCD      1851 TTTTAACTTT TAAAAAAATA CTAACAAAA- ----TACCAA CACAGTAA-G 1900
BOVGSTA    1851 TTTTAACTTA AAAAAAAATA CTAACAAAA- ----GACCAA CACAGCAA-A 1900
MUSGLYTNS  1851 TTTCAACTTT TAAAAGAA-A CAATCAAAAC CAAAACCCAC TACCATGGCA 1900

PGTCD      1901 TACATATTAT TCTTCCTTGC AACTTTGAGC CTTGTCAAAT GGGAGAATGA 1950
BOVGSTA    1901 TACATATTAT TTCTCCTTGT AACTTTGAGC CTTGTAATAC GGGAGAATGA 1950
MUSGLYTNS  1901 AACAGATGAT TTCTCCT-GA CACCTTGAGC CT-GTAATAT GTGAGAAAGA 1950

PGTCD      1951 CTCTGTGG-- --TAATCAGA TGTAAATTCC CAGTGATTTC .......... 2000
BOVGSTA    1951 ACCTGTGG-- --TAATCAGA TGTAAATTCC CAGTGATTTC TTACCTATTT 2000
MUSGLYTNS  1951 GTCTATGGCA AGTAATCAGG TATAAATTCT CAATGATTTC TTATATATTC 2000

PGTCD      2001 .......... .......... .......... .......... .......... 2050
BOVGSTA    2001 TTGGTTGTGG GGGCGGGGAA TGGATACACC ATCAGTTGAA CC........ 2050
MUSGLYTNS  2001 TGGGTCTTGG GAAAACTTGA TTCTAGAAAT CAAAATTAAT TTGACAAAGG 2050

PGTCD      2051 .......... .......... .......... .......... .......... 2100
BOVGSTA    2051 .......... .......... .......... .......... .......... 2100
MUSGLYTNS  2051 AAAAGCAGAT GCCGGAAACT TCTTCCCAGT CTGTCATACA ATTCACCACT 2100
```

```
PGTCD       2101 ..........  ..........  ..........  ..........  ..........  .......... 2150
BOVGSTA     2101 ..........  ..........  ..........  ..........  ..........  .......... 2150
MUSGLYTNS   2101 GGCCAGGTGC  TGAGAGAAGC  ATTAGGGAAC  AGTGTGGGTT  GTGTCAGAGT             2150

PGTCD       2151 ..........  ..........  ..........  ..........  ..........  .......... 2200
BOVGSTA     2151 ..........  ..........  ..........  ..........  ..........  .......... 2200
MUSGLYTNS   2151 TGGACGGCTC  CATCCCTTTG  GCTTCATTAT  CTTCCCTCCTC ATGGAGATTC             2200

PGTCD       2201 ..........  ..........  ..........  ..........  ..........  .......... 2250
BOVGSTA     2201 ..........  ..........  ..........  ..........  ..........  .......... 2250
MUSGLYTNS   2201 TAAAGCAACC  CAGAGAGGCT  TTGCAGCCAG  AGACCTTTAA  TAAGGATGCC             2250

PGTCD       2251 ..........  ..........  ..........  ..........  ..........  .......... 2300
BOVGSTA     2251 ..........  ..........  ..........  ..........  ..........  .......... 2300
MUSGLYTNS   2251 AATGTGACCA  TCAGTCTGTA  AAAGCTGATG  GCTCCAGGAG  CGCTGGCAGT             2300

PGTCD       2301 ..........  ..........  ..........  ..........  ..........  .......... 2350
BOVGSTA     2301 ..........  ..........  ..........  ..........  ..........  .......... 2350
MUSGLYTNS   2301 CCAGGCCCCA  CTAGGCTATT  GTTTCTGTCC  TGGGCATAAA  GGAGGCAGAG             2350

PGTCD       2351 ..........  ..........  ..........  ..........  ..........  .......... 2400
BOVGSTA     2351 ..........  ..........  ..........  ..........  ..........  .......... 2400
MUSGLYTNS   2351 AGTGCCAATA  GGTACTTTGG  TGGCACATGT  TCAGAGTCCA  GGAAAAATCA             2400

PGTCD       2401 ..........  ..........  ..........  ..........  ..........  .......... 2450
BOVGSTA     2401 ..........  ..........  ..........  ..........  ..........  .......... 2450
MUSGLYTNS   2401 AGGGTGACCA  CTTAGAGGGA  CATAGGACTT  GGGGTTGGTG  ATTGAACTGA             2450
```

FIG. 4G

```
PGTCD      2451 ..............  ..............  ..............  ..............  ..............  2500
BOVGSTA    2451 ..............  ..............  ..............  ..............  ..............  2500
MUSGLYTNS  2451 GTTACAAACA CAGACAGCTT TCTTCAGGAT GACTAACAGC AGGAATTGAA 2500

PGTCD      2501 ..............  ..............  ..............  ..............  ..............  2550
BOVGSTA    2501 ..............  ..............  ..............  ..............  ..............  2550
MUSGLYTNS  2501 TGGAAAGTGT GTTCATTTTG TTTTGCCCAA ATTGTATTCA TGCTGTTAGC 2550

PGTCD      2551 ..............  ..............  ..............  ..............  ..............  2600
BOVGSTA    2551 ..............  ..............  ..............  ..............  ..............  2600
MUSGLYTNS  2551 TTTGTGTGTT GAGCCCTGTG GAGAGGGTGT GACTGTATCA GGGAAGGAGA 2600

PGTCD      2601 ..............  ..............  ..............  ..............  ..............  2650
BOVGSTA    2601 ..............  ..............  ..............  ..............  ..............  2650
MUSGLYTNS  2601 GTACCTCAGC GGACTGAGGA CCAGCACCCT ATTATATCAG AAGACAATCT 2650

PGTCD      2651 ..............  ..............  ..............  ..............  ..............  2700
BOVGSTA    2651 ..............  ..............  ..............  ..............  ..............  2700
MUSGLYTNS  2651 CTCATCATCA GGTCCTACCT ACAACCTGCT CTGAACCTCC GAGTTCCTCA 2700

PGTCD      2701 ..............  ..............  ..............  ..............  ..............  2750
BOVGSTA    2701 ..............  ..............  ..............  ..............  ..............  2750
MUSGLYTNS  2701 GCCCATCGTG TTCCAGTGTG GGGGCCTGTA TGGAGCAGGT GACTGAAGAC 2750

PGTCD      2751 ..............  ..............  ..............  ..............  ..............  2800
BOVGSTA    2751 ..............  ..............  ..............  ..............  ..............  2800
MUSGLYTNS  2751 AAAGCCCCCT GTCACATGAC CTCATTTCCC CTGCTCTAGT ACTATGCAAG 2800
```

FIG. 4H

| | | | | | |
|---|---|---|---|---|---|
| PGTCD | 2801 | .......... | .......... | .......... | 2850 |
| BOVGSTA | 2801 | .......... | .......... | .......... | 2850 |
| MUSGLYTNS | 2801 | TGTGACAGCC | AGCCAGCCAG | ATGTACTGGA | CAACATAGGA | ACCGACTTTA | 2850 |
| PGTCD | 2851 | .......... | .......... | .......... | 2900 |
| BOVGSTA | 2851 | .......... | .......... | .......... | 2900 |
| MUSGLYTNS | 2851 | TGGCAATGGG | AGCCGCAGTC | ACTACAACGG | AGCTGCTGAA | GGTTCTGTTC | 2900 |
| PGTCD | 2901 | .......... | .......... | .......... | 2950 |
| BOVGSTA | 2901 | .......... | .......... | .......... | 2950 |
| MUSGLYTNS | 2901 | CCCGCTCTGA | GAGCCTGCAG | GAGCCCCTGT | ATAGGTGGTT | CTCAACCTAT | 2950 |
| PGTCD | 2951 | .......... | .......... | .......... | 3000 |
| BOVGSTA | 2951 | .......... | .......... | .......... | 3000 |
| MUSGLYTNS | 2951 | GGGTCGCGAC | CCCTTTGGGA | AGTGTTAAAT | GACCCTTTCA | CAGGTGTCCC | 3000 |
| PGTCD | 3001 | .......... | .......... | .......... | 3050 |
| BOVGSTA | 3001 | .......... | .......... | .......... | 3050 |
| MUSGLYTNS | 3001 | CTAAGACGGT | TAAAAAACAT | AGATATTTCC | ACTCTGACTG | GTAACAGTAG | 3050 |
| PGTCD | 3051 | .......... | .......... | .......... | 3100 |
| BOVGSTA | 3051 | .......... | .......... | .......... | 3100 |
| MUSGLYTNS | 3051 | CAGAATTACA | GTTATGAAAT | AGCAAGGGAA | ATAATTCTGG | GGTTCGTGTC | 3100 |

FIG. 4I

```
                              Ex4 ▼Ex5             Ex5 ▼Ex6
PGT[Frame 1]   1 MNVKGRVVLS MLLVSTVMVV FWEYINSPEG SLFWIYQSKN PEVG-SSAQR  50
BGT[Frame 1]   1 MNVKGKVILS MLVVSTVIVV FWEYIHSPEG SLFWINPSRN PEVGGSSIQK  50
MGT[Frame 1]   1 MNVKGKVILL MLIVSTVVVV FWEYVNSPDG SFLWIYHTKI PEVGENRWQK  50

Ex6 ▼Ex7                              Ex7 ▼Ex8
PGT[Frame 1]  51 GWWFPSWFNN GTHSYHEEED AIGNEKEQRK EDNRGELPLV DWFNPEKRPE 100
BGT[Frame 1]  51 GWWLPRWFNN G---YHEEDG DINEEKEQRN ED-ESKLKLS DWFNPFKRPE 100
MGT[Frame 1]  51 DWWFPSWFKN GTHSYQEDNV EGRREK-GRN GDRIEEPQLW DWFNPKNRPD 100

Ex8 ▼Ex9
PGT[Frame 1] 101 VVTITRWKAP VVWEGTYNRA VLDNYNAKQK ITVGLTVFAV GRYIEHYLEE 150
BGT[Frame 1] 101 VVTMTKWKAP VVWEGTYNRA VLDNYYAKQK ITVGLTVFAV GRYIEHYLEE 150
MGT[Frame 1] 101 VLTVTPWKAP IVWEGTYDTA LLEKYYATQK LTVGLTVFAV GKYIEHYLED 150

PGT[Frame 1] 151 FLISANTYFM VGHKVIFYIM VDDISRMPLI ELGPLRSFKV FEIKSEKRWQ 200
BGT[Frame 1] 151 FLTSANKHFM VGHPVIFYIM VDDVSRMPLI ELGPLRSFKV FKIKPEKRWQ 200
MGT[Frame 1] 151 FLESADMYFM VGHRVIFYVM IDDTSRMPVV HLNPLHSLQV FEIRSEKRWQ 200
```

FIG. 5A

```
PGT[Frame 1]201  DISMMRMKTI  GEHILAHIQH  EVDFLFCMDV  DQVFQNNFGV  ETLGQSVAQL  250
BGT[Frame 1]201  DISMMRMKTI  GEHIVAHIQH  EVDFLFCMDV  DQVFQDKFGV  ETLGESVAQL  250
MGT[Frame 1]201  DISMMRMKTI  GEHILAHIQH  EVDFLFCMDV  DQVFQDNFGV  ETLGQLVAQL  250

PGT[Frame 1]251  QAWWYKAHPD  EFTYERRKES  AAYIPFGQGD  FYYHAAIFGG  TPTQVLNITQ  300
BGT[Frame 1]251  QAWWYKADPN  DFTYERRKES  AAYIPFGEGD  FYYHAAIFGG  TPTQVLNITQ  300
MGT[Frame 1]251  QAWWYKASPE  KFTYERRELS  AAYIPFGEGD  FYYHAAIFGG  TPTHILNLTR  300

PGT[Frame 1]301  ECFKGILQDK  ENDIEAEWHD  ESHLNKYFLL  NKPTKILSPE  YCWDYHIGMS  350
BGT[Frame 1]301  ECFKGILKDK  KNDIEAQWHD  ESHLNKYFLL  NKPTKILSPE  YCWDYHIGLP  350
MGT[Frame 1]301  ECFKGILQDK  KHDIEAQWHD  ESHLNKYFLF  NKPTKILSPE  YCWDYQIGLP  350

PGT[Frame 1]351  VDIKIVKIAW  QKKEYNLVRN  NI*.......  ..........  ..........  400
BGT[Frame 1]351  ADIKLVKMSW  QTKEYNVVRN  NV*.......  ..........  ..........  400
MGT[Frame 1]351  SDIKSVKVAW  QTKEYNLVRN  NV*.......  ..........  ..........  400
```

FIG.5B

A   ApaI
B   BamHI
C   ClaI
E   EcoRI
G   BglII
H   HindIII
K   KpnI
N   NotI
P   PstI
S   Sal
Sa  SacI
V   EcoRV
X   XbaI
Xh  XhoI No sites for: Xho, Kpn, SacII, Sma, Cla, EcoRV, Apa, Not, PvuI, Nde pUBS:

.... SacI SacII Not Xba Spe Bam Sma Pst Eco RV Hind Cla Sal Xho Apa Kpn ....

```
         10         20         30         40         50         60
GAGGGCTGCA GGAATTCGAT GATCCCCCAG CTTGAAGTTC CTATTCCGAA GTTCCTATTC 70         80         90        100        110        120
TCTAGAAAGT ATAGGAACTT CAAGCTGGGC TGCAGGAATT CGATTCGAGC AGTGTGGTTT 130        140        150        160        170        180
TGCAAGAGGA AGCAAAAAGC CTCTCCACCC AGGCCTGGAA TGTTTCCACC CAATGTCGAG 190        200        210        220        230        240
CAGTGTGGTT TTGCAAGAGG AAGCAAAAAG CCTCTCCACC CAGGCCTGGA ATGTTTCCAC 250        260        270        280        290        300
CCAATGTCGA GCAAACCCCG CCCAGCGTCT TGTCATTGGC GAATTCGAAC ACGCAGATGC 310        320        330        340        350        360
AGTCGGGGCG GCGCGGTCCC AGGTCCACTT GGCATATTAA GGTGACGCGT GTGGCCTCGA 370        380        390        400        410        420
ACACCGAGCG ACCCTGCAGC CAATATGGGA TCGGCCATTG AACAAGATGG ATTGCACGCA 430        440        450        460        470        480
GGTTCTCCGG CCGCTTGGGT GGAGAGGCTA TTCGGCTATG ACTGGGCACA ACAGACAATC 490        500        510        520        530        540
GGCTGCTCTG ATGCCGCCGT GTTCCGGCTG TCAGCGCAGG GCGCCCGGT TCTTTTTGTC 550        560        570        580        590        600
AAGACCGACC TGTCCGGTGC CCTGAATGAA CTCCAAGACG AGGCAGCGCG GCTATCGTGG 610        620        630        640        650        660
CTGGCCACGA CGGGCGTTCC TTGCGCAGCT GTGCTCGACG TTGTCACTGA AGCGGGAAGG 670        680        690        700        710        720
GACTGGCTGC TATTGGGCGA AGTGCCGGGG CAGGATCTCC TGTCATCTCA CCTTGCTCCT 730        740        750        760        770        780
GCCGAGAAAG TATCCATCAT GGCTGATGCA ATGCGGCGGC TGCATACGCT TGATCCGGCT 790        800        810        820        830        840
ACCTGCCCAT TCGACCACCA AGCGAAACAT CGCATCGAGC GAGCACGTAC TCGGATGGAA 850        860        870        880        890        900
GCCGGTCTTG TCGATCAGGA TGATCTGGAC GAAGAGCATC AGGGGCTCGC GCCAGCCGAA 910        920        930        940        950        960
CTGTTCGCCA GGCTCAAGGC GCGGATGCCC GACGGCGAGG ATCTCGTCGT GACCCATGGC 970        980        990       1000       1010       1020
GATGCCTGCT TGCCGAATAT CATGGTGGAA AATGGCCGCT TTTCTGGATT CATCGACTGT 1030       1040       1050       1060       1070       1080
GGCCGGCTGG GTGTGGCGGA CCGCTATCAG GACATAGCGT TGGCTACCCG TGATATTGCT 1090       1100       1110       1120       1130       1140
GAAGAGCTTG GCGGCGAATG GGCTGACCGC TTCCTCGTGC TTTACGGTAT CGCCGCTCCC
```

FIG. 16A

```
          1150       1160       1170       1180       1190       1200
     GATTCGCAGC GCATCGCCTT CTATCGCCTT CTTGACGAGT TCTTCTGAGG GGATCGGCAA 1210       1220       1230       1240       1250       1260
     TAAAAAGACA GAATAAAACG CACGGGTGTT GGGCGTTTGT TCGGATCATC AAGCTTGAAG 1270       1280       1290       1300       1310       1320
     TTCCTATTCC GAAGTTCCTA TTCTCTAGAA AGTATAGGAA CTTCAAGCTT ATCGATGAGT 1330       1340       1350       1360       1370       1380
     AGATCTTGAT CGATACCGTC ........  ..........  ..........  ..........
```

Linker sequences : 0-28

FRT : 29-104

Polyoma virus enhancer repeats : 105-249

Herpes Simplex Virus Tyrosine Kinase promoter : 250-385

Neomycin phosphotransferase coding region : 385-1188

Herpes Simplex Virus Tyrosine Kinase PolyA signal : 1189-1249

FRT : 1250-1310

Linker sequences : 1311-1340

FIG. 16B 5.5kb galT PRODUCT    5.5kb KO PRODUCT

1. CBAC TEMPLATE; WILD TYPE PRIMERS
2. 7C2 TEMPLATE; WILD TYPE PRIMERS
3. CBAC TEMPLATE; KO PRIMERS
4. 7C2 TEMPLATE; KO PRIMERS i) Ferrochelatase, FC-F/R
M, Marker SPP-1
C, MQW control
K, KIDNEY
H, HEART
L, LIVER
FIG. 24a
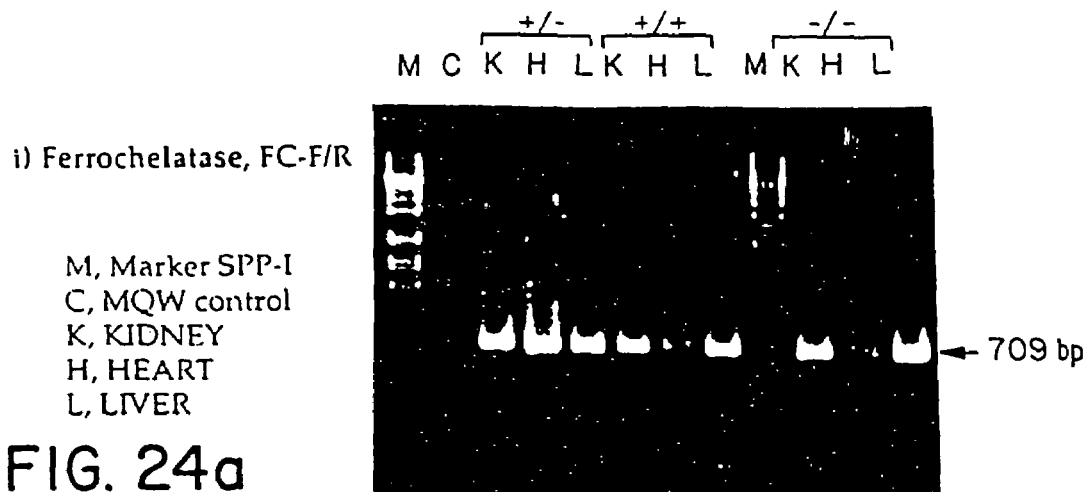
← 709 bp
ii) α-1,3-GT cDNA spike
+ 7F/9R2 primers
FIG. 24b
← 619 bp
iii) α-1,3-GT
7F/9R2 primers
FIG. 24c
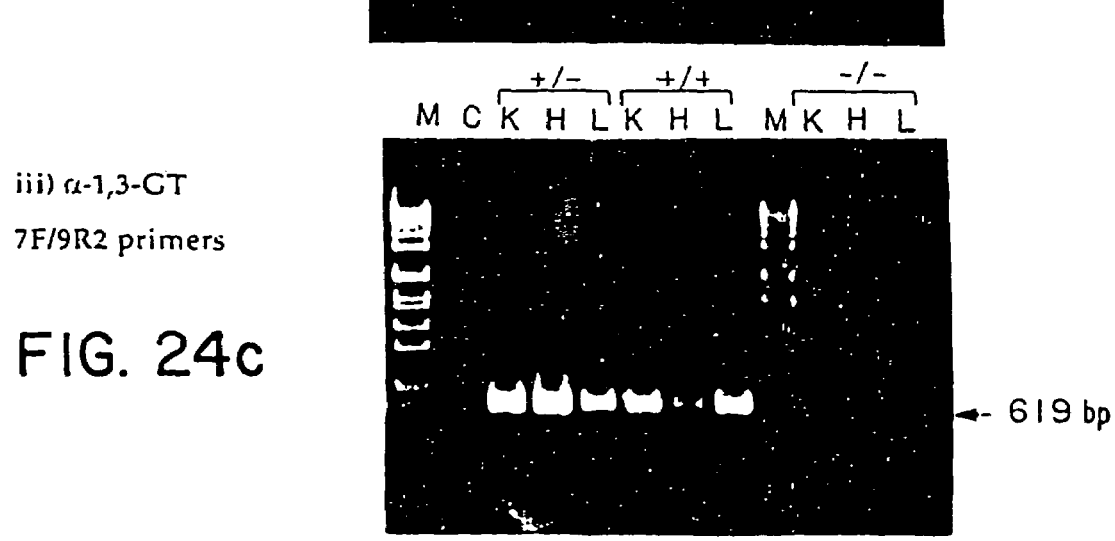
← 619 bp MOUSE 19: WILD TYPE; MOUSE 20: HETEROZYGOTC Gal KO; MOUSE 21: HOMOZYGOUS Gal KO T-LIF SEQUENCE - Murine

CTGACACCTTTCGCTTTCCTCTTGCGTGTCCGCCTGCGACCTTTCCCCACCCC

GGCCTCTTTCCTGGTTGCACCACTTCCTCTCATTCCAAAGGATTGTGCCCTTA

CTGCTGCTGGTTCTGCACTGGAAACACGGGGCAGGGAGCCCTCTTCCCATCAC

CCCTGTAAATGCCACCTGTGCCATACGCCACCCATGCCACGGCAACCTC

```
Met Asn Gln Ile Lys Asn Gln Leu Ala Gln Leu Asn Gly
ATG AAC CAG ATC AAG AAT CAA CTG GCA CAG CTC AAT GGC

Ser Ala Asn Ala Leu Phe Ile Ser Tyr Tyr Thr Ala Gln Gly
AGC GCC AAT GCT CTC TTC ATT TCC TAT TAC ACA GCT CAA GGX

Glu Pro Phe Pro Asn Asn Val Glu Lys Leu Cys Ala Pro Asn
GAG CCG TTT CCC AAC AAC GTG GAA AAG CTA TGT GCG CCT AAC

Met Thr Asp Phe Pro Ser Phe His Gly Asn Gly Thr Glu Lys
ATG ACA GAC TTC CCA TCT TTC CAT GGC AAC GGG ACA GAG AAG

Thr Lys Leu Val Glu Leu Tyr Arg Met Val Ala Tyr Leu Ser
ACC AAG TTG GTG GAG CTG TAT CGG ATG GTC GCA TAC CTG AGC

Ala Ser Leu Thr Asn Ile Thr Arg Asp Gln Lys Val Leu Asn
GCC TCC CTG ACC AAT ATC ACC CGG GAC CAG AAG GTC CTG AAC

Pro Thr Ala Val Ser Leu Gln Val Lys Leu Asn Ala Thr Ile
CCC ACT GCC GTG AGC CTC CAG GTC AAG CTC AAT GCT ACT ATA

Asp Val Met Arg Gly Leu Leu Ser Asn Val Leu Cys Arg Leu
GAC GTC ATG AGG GGC CTC CTC AGC AAT GTG CTT TGC CGT CTG

Cys Asn Lys Tyr Arg Val Gly His Val Asp Val Pro Pro Val
TGC AAC AAG TAC CGT GTG GGC CAC GTG GAT GTG CCA CCT GTC

Pro Asp His Ser Asp Lys Glu Ala Phe Gln Arg Lys Lys Leu
CCC GAC CAC TCT GAC AAA GAA GCC TTC CAA AGG AAA AAG TTG

Gly Cys Gln Leu Leu Gly Thr Tyr Lys Gln Val Ile Ser Val
GGT TGC CAG CTT CTG GGG ACA TAC AAG CAA GTC ATA AGT GTG

Val Val Gln Ala Phe ***
GTG GTC CAG GCC TTC TAG AGAGGAGGTCTTGAATGTACCATGGACTG...
```

FIG. 26

HUMAN T-1TF SEQUENCE

```
GACCTTTTGC CTTTTCTCTC TCCTGGTGCA CCATTTCCTC TCCCTCCCTG        50
AGCCGGAGTT GTGCCCCTGC TGTTGGTTCT GCACTGGAAA CATGGGGCGG       100
GGAGCCCCCT CCCCATCACC CCTGTCAACG CCACCTGTGC CATACGCCAC       150
CCATGTCACA ACAACCTC ATG AAC CAG ATC                          182
                    Met Asn Gln Ile
AGG AGC CAA CTG GCA CAG CTC AAT GGC AGT GCC AAT GCC CTC      227
Arg Ser Gln Leu Ala Gln Leu Asn Gly Ser Ala Asn Ala Leu
 5               10                  15
TTT ATT CTC TAT TAC ACA GCC CAG GGG GAG CCG TTC CCC AAC      272
Phe Ile Leu Tyr Tyr Thr Ala Gln Gly Glu Pro Phe Pro Asn
     20              25                  30
AAC CTG GAC AAG CTA TGT GGC CCC AAC GTG ACG GAC TTC CCG      317
Asn Leu Asp Lys Leu Cys Gly Pro Asn Val Thr Asp Phe Pro
         35              40                  45
CCC TTC CAC GCC AAC GGC ACG GAG AAG GCC AAG CTG GTG GAG      362
Pro Phe His Ala Asn Gly Thr Glu Lys Ala Lys Leu Val Glu
             50              55                  60
CTG TAC CGC ATA GTC GTG TAC CTT GGC ACC TCC CTG GGC AAC      407
Leu Tyr Arg Ile Val Val Tyr Leu Gly Thr Ser Leu Gly Asn
                 65              70
ATC ACC CGG GAC CAG AAG ATC CTC AAC CCC AGT GCC CTC AGC      452
Ile Thr Arg Asp Gln Lys Ile Leu Asn Pro Ser Ala Leu Ser
75              80                  85
CTC CAC AGC AAG CTC AAC GCC ACC GCC GAC ATC CTG CGA GGC      497
Leu His Ser Lys Leu Asn Ala Thr Ala Asp Ile Leu Arg Gly
    90              95                  100
CTC CTT AGC AAC GTG CTG TGC CGC CTG TGC AGC AAG TAC CAC      542
Leu Leu Ser Asn Val Leu Cys Arg Leu Cys Ser Lys Tyr His
        105                 110                 115
GTG GGC CAT GTG GAC GTG ACC TAC GGC CCT GAC ACC TCG GGT      587
Val Gly His Val Asp Val Thr Tyr Gly Pro Asp Thr Ser Gly
            120                 125                 130
AAG GAT GTC TTC CAG AAG AAG AAG CTG GGC TGT CAA CTC CTG      632
Lys Asp Val Phe Gln Lys Lys Lys Leu Gly Cys Gln Leu Leu
                135                 140
GGG AAG TAT AAG CAG ATC ATC GCC GTG TTG GCC CAG GCC TTC      677
Gly Lys Tyr Lys Gln Ile Ile Ala Val Leu Ala Gln Ala Phe
145                 150                 155
TAG CAGGAGGTCT                                               722
***
```

FIG. 27

MATERIALS AND METHODS FOR MANAGEMENT OF HYPERACUTE REJECTION IN HUMAN XENOTRANSPLANTATION

CROSS REFERENCE TO RELATED APPLICATIONS

This application claims benefit of priority, and is a continuation, of U.S. application Ser. No. 08/984,900, filed Dec. 4, 1997, now U.S. Pat. No. 6,849,448, which claims benefit of priority, and is a divisional, of U.S. application Ser. No. 08/378,617, filed Jan. 26, 1995, now U.S. Pat. No. 5,849, 991, issued Dec. 15, 1998, which claims benefit of priority, and is a continuation-in-part, of U.S. application Ser. No. 08/188,607, filed Jan. 27, 1994, now abandoned.

FIELD OF THE INVENTION

This invention relates generally to the field of xenotransplantation. In particular this invention relates to methods and materials for reduction or elimination of the hyperacute rejection response in humans. More particularly, this invention relates to methods for treating human serum to reduce or eliminate hyperacute rejection. This invention also relates to methods and materials for generating non-human organs lacking or having reduced α 1,3 galactosyl transferase activity.

BACKGROUND OF THE INVENTION

It is widely acknowledged that there is an acute, worldwide shortage of human organs for transplantation. This is in spite of legislative changes and education programs to increase public awareness of the problem. In the United States, for example, there is an estimated annual shortfall of approximately 18,000 kidneys/year. Similarly, in Australia in 1992, only 41% of renal patients awaiting transplantation received transplants. In Japan the imbalance between supply and demand is even greater due to religious prohibitions on the use of organs from cadaveric donors.

The benefits of transplantation can be seen by comparing the rehabilitation rates of transplant patients with those of dialysis patients. In Australia and New Zealand, the majority of transplant patients (60%) are capable of full time work or school with a further 10% in part time work, while only 7% are unfit for work. In contrast, 23% of dialysis patients are capable of full time work or school, with 15% involved in part time work and 20% unfit for work. The remainder are "retired." Fifteenth Report of the Australia and New Zealand Dialysis and Transplant Registry (ANZDATA), Queen Elizabeth Hospital, Woodville, S.A., APS Disney, ed. (1992).

The direct financial cost of dialysis in Australia and New Zealand is approximately $A45,000/patient/year. In addition, indirect costs due to unemployment and sickness are higher in dialysis patients and the social costs are considerable. Transplantation engenders an expense of approximately $A30,000/patient in the first year and $A14,000/patient/year thereafter. These statistics indicate that a) transplantation is the optimal therapy for end stage renal failure; b) there is an undersupply of donor kidneys; and c) present strategies aimed at increasing the transplant rate have been less than successful. There are, in addition, serious shortages of other transplantable organs including hearts, livers, lungs and pancreases.

The use of xenografts (transplants between species) is one option for overcoming the short supply of human organs for transplantation. Non-viable, non-antigenic xenografts are commonly used in vascular reconstruction (bovine arteries) and in cardiac surgery (porcine cardiac valves). However, despite their occasional use in the past, immunological barriers have prevented the common use of viable xenografts. Between 1964 and 1991 a total of 27 non-human primate to human organ xenografts was reported; the longest reported patient survival was 9 months. Two liver transplants from baboon to human were recently performed in anticipation that modern immunosuppressive therapies could cope with the severe rejection problems likely to occur in xenotransplantation. To date, the course of one of these patients has been reported, and in this case rejection was not the direct cause of death. Starzl et al., Baboon-to-Human Liver Transplantation. *Lancet* 341: 65–71 (1993). This clinical experience indicates that a) non-human organs can function and support human life; b) rejection episodes can be reversed by conventional anti-rejection therapy; and c) the mechanisms of rejection are similar, in principle, to those in allograft rejection.

It is unlikely that primates will be a satisfactory source of organs for xenotransplantation. Most are endangered species, breed slowly in the wild and poorly in captivity. The baboon is an exception to these generalizations, but other disadvantages limit the usefulness of this species. Baboons have single pregnancies, long gestation times, are difficult and expensive to maintain and may be infected with or carry organisms, particularly viruses, that are pathogenic in humans. For hearts and kidneys where organ size may be a consideration, the smaller primates are unsatisfactory as donors to human adults. Finally, the use of primates is likely to arouse considerable opposition from the public.

These difficulties have led to renewed interest in the use of non-primate species as organ donors for human patients. The pig is a widely acknowledged choice for xenotransplantation into humans. The pig erythrocyte diameter (6.5 μm) and, by implication, its capillary size, are similar to humans, facilitating connection of xenografts to the human circulatory system. The pig breeds well in captivity, has a short gestation time and produces large litters. In addition, pigs can be bred and maintained in low pathogen facilities, can be reared to any size and do not arouse the level of public reaction associated with primates.

The immunological barriers to use of pig organs in human patients include a) an immediate severe ("hyperacute") rejection phenomenon that develops in minutes to hours after transplantation, and b) a proposed acute rejection that develops in days to weeks. Once the hyperacute rejection phenomenon has been overcome, it is expected that normal acute rejection would ensue. This form of rejection is thought to be similar to that experienced with allografts (transplants between individuals of the same species) and should be amenable to normal immunosuppressive therapies.

Both preformed "natural antibodies" (xenoantibodies) and complement regulating factors in human serum are thought to be involved in the process of hyperacute rejection. Hyperacute rejection is thought to be initiated when xenoantibodies bind to epitopes on the endothelium of a donor organ, activating the classical complement pathway.

SUMMARY OF THE INVENTION

A purified and isolated nucleic acid molecule of the present invention comprises the porcine nucleic acid sequence depicted in FIG. 4 (SEQ ID NO: 7), which encodes a porcine polypeptide having α-1,3 galactosyltransferase activity. Variations on this sequence that may be routinely generated by the skilled artisan include those sequences corresponding to FIG. 4 but varying within the scope of the degeneracy of the genetic code. That is, the present invention includes variants of the sequence set out in FIG. 4, readily determined by the skilled artisan, that code for the same amino acid sequence encoded by the sequence set out in FIG. 4. The present invention also includes a purified and isolated nucleic acid molecule that encodes a porcine α-1,3 galactosyltransferase and that hybridizes under standard high stringency conditions with a sequence complementary to the sequence set out in FIG. 4, or with a sequence complementary to a variation of the sequence set out in FIG. 4 within the scope of the degeneracy of the genetic code. The complementary strands to the above-described nucleic acid sequences are readily determined by standard methods, and are also within the scope of the present invention.

Within the parameters set out in the preceding paragraph, the present invention includes variants of the porcine α-1,3 galactosyltransferase coding sequence that preserve the functional characteristics of the native gene product. Such variants include, for example, minor nucleotide variations in the 5' untranslated region or in various coding regions of the disclosed sequence. Minor amino acid variations deriving from changes in the coding regions, that leave a functional α-1,3 galactosyltransferase catalytic site, membrane anchor domain and stem region as described below, are within the scope of the present invention. Such routine variations in nucleic acid and amino acid sequences can be identified by those having ordinary skill in the art based on the sequence and structural information provided herein.

As used herein, "high stringency conditions" are those hybridization conditions generally understood by the skilled artisan to reflect standard-conditions of high stringency as set out in widely recognized protocols for nucleic acid hybridization. See, e.g., Sambrook et al, *Molecular Cloning: A Laboratory Manual* (2nd Edition), Cold Spring Harbor Laboratory Press (1989), pp. 1.101–1.104; 9.47–9.58 and 11.45–11.57. Generally, these conditions reflect at least one wash of the hybridization membrane in 0.05× to 0.5×SSC with 0.1% SDS at 65° C., or washing conditions of equivalent stringency.

The present invention also includes a host cell transformed with any of the above-described purified and isolated nucleic-acid molecules, as well as a porcine α-1,3 galactosyltransferase encoded by such transforming nucleic acid molecules and expressed from the host cell. Methods for transforming appropriate host cells and for expressing polypeptides from such host cells are known in the art and are described, for example, in Sambrook et al., (1984), pp. 12.2–12.44; 16.3–17.44.

The invention further includes a DNA construct useful for inactivating the porcine α-1,3 galactosyltransferase gene by insertion of a desired DNA sequence into an insertion site of the gene. As used herein, the term "α-1,3 galactosyltransferase gene" includes the exons encoding or potentially encoding α-1,3 galactosyltransferase, introns contiguous with such exons, and regulatory elements associated with such exons and introns. The DNA construct includes the desired DNA sequence flanked by first and second homology sequences. These first and second homology sequences are sufficiently homologous, respectively, to first and second genomic sequences flanking the insertion site to allow for homologous recombination of the DNA construct with the porcine α-1,3 galactosyltransferase gene when the DNA construct is introduced into a target cell containing the porcine α-1,3 galactosyltransferase gene. Preferably the insertion site is within exon 4, exon 7, exon 8 or exon 9 of the porcine α-1,3 galactosyltransferase gene. The desired DNA sequence is preferably a selectable marker, including but not limited to the neo$^R$ gene, the hydromycin resistance (hyg$^R$) gene and the thymidine kinase gene. The desired DNA sequence may be bordered at both ends by FRT DNA elements, with stop codons for each of the three reading frames being inserted 3' to the desired DNA sequence. Presence of the FRT elements allows the selectable marker to be deleted from the targeted cell, and the stop codons ensure that the α-1,3 galactosyltransferase gene remains inactivated following deletion of the selectable marker.

The invention further includes a DNA construct useful for inactivating the murine α-1,3 galactosyltransferase gene by insertion of a desired DNA sequence into an insertion site of the gene. The DNA construct includes the desired DNA sequence flanked by first and second homology sequences. These first and second homology sequences are sufficiently homologous, respectively, to first and second genomic sequences flanking the insertion site to allow for homologous recombination of the DNA construct with the murine α-1,3 galactosyltransferase gene when the DNA construct is introduced into a cell containing the murine α-1,3 galactosyltransferase gene. Preferably the insertion site is within exon 4, exon 7, exon 8 or exon 9 of the murine α-1,3 galactosyltransferase gene. The desired DNA sequence is preferably a selectable marker, including but not limited to the neo$^R$ gene, the hyg$^R$ gene and the thymidine kinase gene. The desired DNA sequence may be bordered at both ends by FRT DNA elements, with stop codons for each of the three reading frames being inserted 3' to the desired DNA sequence. Presence of the FRT elements allows the selectable marker to be deleted from the targeted cell, and the stop codons ensure that the α-1,3 galactosyltransferase gene remains inactivated following deletion of the selectable marker.

The invention also includes methods for generating a mammalian totipotent cell having at least one inactivated (non-functional) α-1,3 galactosyltransferase alleles, where the totipotent cell is derived from a mammalian species in which alleles for the α-1,3 galactosyltransferase gene normally are present and functional. A "functional" allele is capable of being transcribed and translated to produce a polypeptide having an activity the same as or substantially similar to the native α-1,3 galactosyltransferase. The methods include providing a plurality of cells characterized as totipotent cells of the aforementioned mammalian species, introducing into the totipotent cells a nucleic acid construct effective for inactivating the α-1,3 galactosyltransferase gene by insertion of a desired DNA sequence into an insertion site of the gene through homologous recombination, and then identifying a totipotent cell having at least one inactivated α-1,3 galactosyltransferase allele.

The totipotent cells can include, without limitation, embryonic stem (ES) cells, primordial germ cells (PGC's) and eggs. The cells can be taken from a variety of mammalian species in which alleles for the α-1,3 galactosyltransferase gene are present and functional, including without limitation murine and porcine species.

The invention further includes methods for generating a mammal lacking a functional α-1,3 galactosyltransferase gene, where the mammal belongs to a species having a functional α-1,3 galactosyltransferase gene. The methods include providing a mammalian totipotent cell having at least one inactivated α-1,3 galactosyltransferase allele, where the totipotent cell is derived from the aforementioned mammalian species having a functional α-1,3 galactosyltransferase gene, manipulating the totipotent cell such that mitotic descendants of the cell constitute all or part of a developing embryo, allowing the embryo to develop to term, recovering a neonate individual derived from the embryo, and raising and breeding the neonate to obtain a mammal homozygous for an inactivated α-1,3 galactosyltransferase allele, i.e., a mammal in which both α-1,3 galactosyltransferase allele are inactivated.

The totipotent cells can include, without limitation, ES cells, PGC's and eggs. The cells can be taken from a variety of mammalian species in which alleles for the α-1,3 galactosyltransferase gene are present and functional, including without limitation murine and porcine species. ES cells and PGC's are manipulated in various ways such that their mitotic descendants are found in a developing embryo. These manipulations can include, without limitation, injection into a blastocyst or morula, co-culture with a zona pellucida-disrupted morula, and fusion with an enucleated zygote. Cells injected into a blastocyst- or morula-stage embryo become incorporated into the inner cell mass of the blastocyst embryo, giving rise to various differentiated cell types of the resulting embryo, including in some cases germ cells. The embryo derived from such manipulations is a chimera composed of normal embryonic cells as well as mitotic descendants of the introduced ES cells or PGC's. Alternatively, chimeric embryos can be obtained by co-culturing at least one ES cell or PGC with a morula embryo in which the zona pellucida is sufficiently disrupted to allow direct contact between the ES cell/PGC and at least one cell of the morula. The zona pellucida-disrupted embryo may be an embryo that is completely free of the zona pellucida. Finally, the genome of an ES cell or PGC can be incorporated into an embryo by fusing the ES cell/PGC with an enucleated zygote. Such a procedure is capable of generating a non-chimeric embryo, i.e., an embryo in which all nuclei are mitotic descendants of the fused ES cell/PGC nucleus. The resulting embryos are implanted in a recipient female, or surrogate mother, and allowed to develop to term.

When eggs, as opposed to ES cells or PGC's, are directly injected with a nucleic acid construct effective for inactivating the α-1,3 galactosyltransferase gene, the eggs can be manipulated to form an embryo by implanting into a recipient female.

The invention also includes a mammal, produced through human intervention, that lacks a functional α-1,3 galactosyltransferase gene. The mammal belongs to a species in which the α-1,3 galactosyltransferase gene is normally present and functional. The mammal can be, without limitation, a mouse or a pig.

The invention further includes a purified and isolated nucleic acid molecule comprising a nucleic acid sequence selected from the group consisting of (1) the nucleic acid sequence depicted in FIG. 26 (SEQ ID NO: 25), (2) a sequence corresponding to the sequence of (1) within the scope of the degeneracy of the genetic code, and (3) a sequence that encodes murine T-LIF and that hybridizes under standard high stringency conditions with a sequence complementary to the sequence of (1) or (2). The complementary strands to the above-described nucleic acid sequences are readily determined by standard methods, and are also within the scope of the present invention.

The present invention also includes a host cell transformed with any of the purified and isolated nucleic acid molecules described in the preceding paragraph, as well as a T-LIF polypeptide encoded by such transforming nucleic acid molecules and expressed from the host cell.

The invention further includes a purified and isolated nucleic acid molecule comprising a nucleic acid sequence selected from the group consisting of (1) the nucleic acid sequence depicted in FIG. 27 (SEQ ID NO: 31), (2) a sequence corresponding to the sequence of (1) within the scope of the degeneracy of the genetic code, and (3) a sequence that encodes human T-LIF and that hybridizes under standard high stringency conditions with a sequence complementary to the sequence of (1) or (2). The complementary strands to the above-described nucleic acid sequences are readily determined by standard methods, and are also within the scope of the present invention.

The present invention also includes a host cell transformed with any of the purified and isolated nucleic acid molecules described in the preceding paragraph, as well as a T-LIF polypeptide encoded by such transforming nucleic acid molecules and expressed from the host cell.

The invention further includes a method for eliminating or reducing hyperacute rejection of non-primate mammalian cells by human serum, comprising adding, to the human serum, a physiologically acceptable amount of galactose or a saccharide in which the terminal carbohydrate is an a galactose linked at position 1, prior to exposure of the human serum to the non-primate cells. The amount of galactose or saccharide added is sufficient to reduce or eliminate the hyperacute rejection response. The saccharide can be, without limitation, melibiose, galactose α1-3 galactose or stachyose. Alternatively, the human serum can be treated so as to be substantially depleted of immunoglobulin, IgM antibodies, anti-GAL IgM and IgG antibodies, or anti-GAL IgM antibodies. The invention further includes affinity-treated human serum substantially free of anti-GAL antibodies or of anti-GAL IgM antibodies.

BRIEF DESCRIPTION OF THE DRAWINGS

FIG. 3 depicts physiograph tracings of perfused rat heart contractions in the presence of human serum with or without selected saccharides.

FIG. 4 is a comparison of the porcine α-1,3 galactosyltransferase cDNA sequence with the corresponding murine and bovine sequences. PGTCD=porcine sequence (SEQ ID NO:7). BOVGSTA=bovine sequence (SEQ ID NO:8). MUSGLYTNG=murine sequence (SEQ ID NO:9).

FIG. 5 is a comparison of the porcine α-1,3 galactosyltransferase amino acid sequence with the corresponding murine and bovine amino acid sequences. PGT=porcine sequence (SEQ ID NO:10). BGT=bovine sequence (SEQ ID NO:11). MGT=murine sequence (SEQ ID NO:12).

FIG. 16 sets out the nucleotide sequence (SEQ ID NO:13) of a neomycin resistance cassette used in the construction of a DNA construct for interrupting the α-1,3-GalT gene in mice

FIG. 24 shows the PCR fragments generated from cDNA obtained from RNA isolated from kidney (K), heart (H) and liver (L) of a wild-type mouse (+/+), a mouse heterozygous for the interrupted α-1,3-GalT allele (+/−) and a mouse homozygous for the interrupted α-1,3-GalT allele (−/−).

FIG. 26 is a representation of the nucleotide sequence (SEQ ID NO:25) and deduced amino acid sequence (SEQ ID NO:26) for murine T-LIF.

FIG. 27 is a representation of the nucleotide sequence (SEQ ID NO:31) and deduced amino acid sequence (SEQ ID NO:32) for human T-LIF.

DETAILED DESCRIPTION

Figure 1:
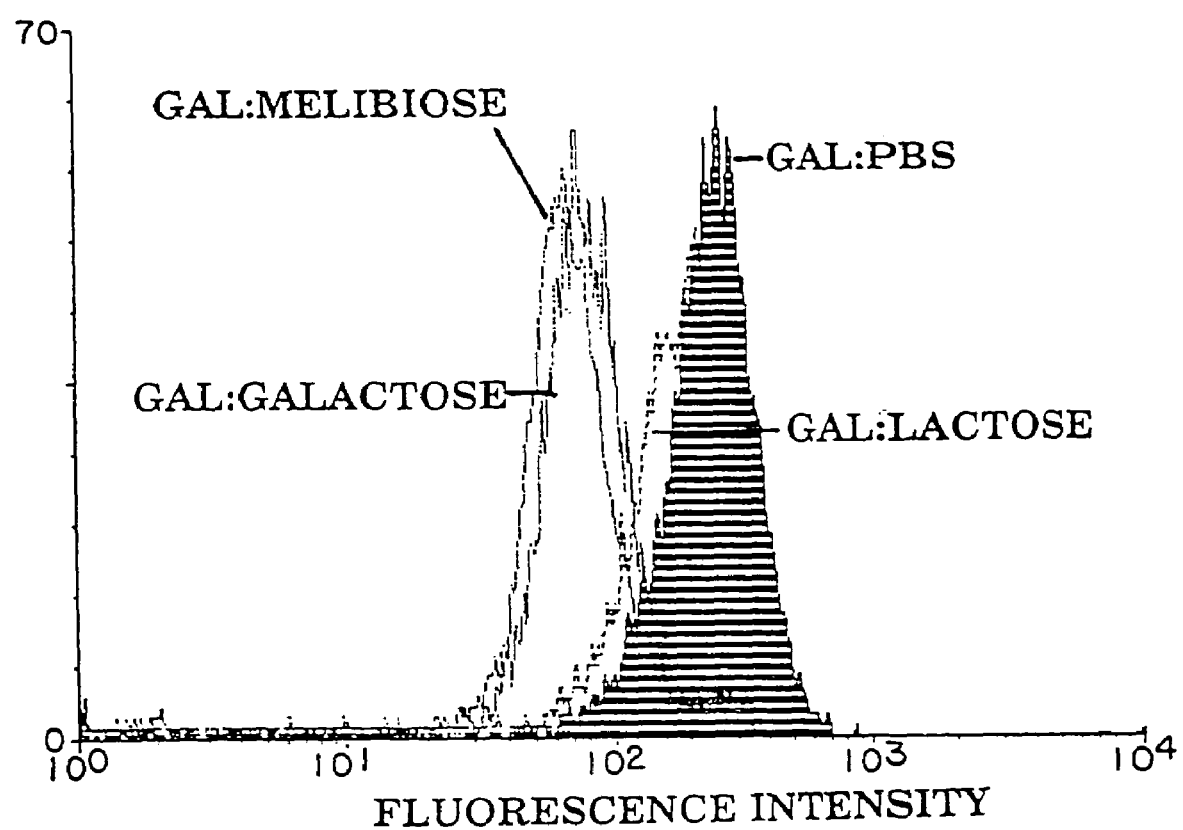
FIG. 1 is a graphical representation of fluorescence intensity following immunofluorescent-staining of porcine aortic endothelial cells with anti-GAL antibody alone or with anti-GAL antibody that was preincubated with selected saccharides.

Evidence presented herein establishes that a substantial portion of human pre-formed, anti-pig xenoantibodies recognize a specific terminal galactose linkage on the surface of pig endothelial cells. As demonstrated in experiments carried out by the present inventors, it is possible to reduce the titers of preformed xenoantibodies by adsorption with immobilized antigens containing the appropriate epitopes. This leads to reduction or elimination of cellular responses associated with the hyperacute rejection response. Conversely, it is demonstrated to be possible to neutralize such antibodies by addition of appropriate carbohydrate antigens to human serum. In demonstrating the usefulness of these approaches, it was necessary to identify the relevant carbohydrate moieties and to demonstrate their efficacy in cultured cell systems and, importantly, in whole organs. As such, one approach to reducing or eliminating the hyperacute rejection response is identified as treatment of the recipient by eliminating or neutralizing the relevant antibody populations.

An alternative approach to xenotransplantation would be elimination of the relevant epitope(s) in the donor organ. This could be accomplished, for example, by reducing or eliminating expression of the gene(s) encoding the metabolic machinery responsible for formation of the epitopes. The epitope defined by the α-1,3 galactose linkage (termed the GAL epitope) is generated by the enzyme UDP-galactose: β-D-galactosyl-1,4-N-acetyl-D-glucosaminide α-1,3 galactosyl-transferase ("α-1,3 galactosyltransferase" or "α-1,3-GalT"). This enzyme transfers galactose to the terminal galactose residue of N-acetyllactosamine-type carbohydrate chains and lactosaminoglycans. The reaction catalyzed by α-1,3-GalT may be summarized as follows:

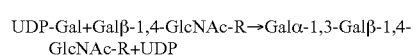

UDP-Gal+Galβ-1,4-GlcNAc-R→Galα-1,3-Galβ-1,4-GlcNAc-R+UDP

The α-1,3-Gal T enzyme is found in most mammals, but is not present in Old World monkeys and humans. For purposes of xenotransplantation, it is significant that humans and Old World monkeys have naturally occurring xenoantibodies directed against the GAL epitope. The use of pig organs lacking the GAL epitope could reduce or eliminate the hyperacute rejection of such organs by human recipients. The utility of such an approach is buttressed by the present inventors' demonstration that the GAL epitope is, in fact, central to the hyperacute rejection phenomenon in cells and whole organs. One approach to obtaining such organs would be to generate pigs in which the gene encoding the α-1,3-GalT enzyme is "knocked out" by homologous recombination.

Role of the GAL Epitope in Hyperacute Rejection

The present inventors have affinity purified antibodies directed against the GAL epitope (anti-GAL antibodies) from human serum. This was accomplished with affinity columns comprising the appropriate epitopes (e.g., galactosyl-galactose or melibiose) attached to a solid phase. Total anti-GAL IgG and IgM were obtained in one set of experiments. In an alternative approach, anti-GAL IgG was obtained by passage of serum over an affinity column with specificity for all proteins except albumin and IgG. The wash-through from this column was then applied to a galactosyl-galactose affinity column and purified anti-GAL IgG was collected as the eluate. The obtained anti-GAL IgG can be further purified by passage over a protein G column, which specifically binds IgG but not other antibody isotypes. Conversely, the wash-through from the above-described columns can be used as sources of total anti-GAL (IgG+IgM)-depleted serum or of anti-GAL IgG-depleted serum in further experiments. Preferably, the anti-GAL antibody preparations are characterized for protein content, molecular weight and purity, and for antibody class and isotype.

To demonstrate the role of the GAL epitope in the hyperacute rejection response, it is necessary, first, to establish that IgG and IgM anti-GAL antibodies react with porcine cells and tissues. The present inventors investigated the binding of human anti-GAL antibodies to porcine cells and tissues using immunofluorescent staining. In this technique, selected human antibody preparations are reacted with intact porcine cells and then reacted with signal antibody comprising non-human anti-human IgG or IgM labeled with fluorescein isothiocyanate (FITC). Stained cells may be detected and quantified with a fluorescence-activated cell sorter (FACS) or other appropriate detection means. Other methods for detecting the presence of a bound antibody on a cell surface, for example through use of enzyme-labeled signal antibody reagents, are known to the skilled artisan.

Total anti-GAL (IgM and IgG), as well as purified anti-GAL IgG, stained cells from a porcine epithelial cell line ($PK_1$) as well as cells from a porcine aortic endothelial cell line (PAE). Neither anti-GAL (total IgM+IgG) antibody-depleted serum nor anti-GAL IgG-depleted serum gave detectable staining. To further investigate the specificity of the response, it is desirable to determine whether or not reactivity of the antibodies with porcine cells can be diminished or eliminated by prior exposure to one or more molecules suspected of comprising the epitope(s) in question. In this regard, the present inventors have established that antibody binding is inhibited by galactose and by disaccharides having terminal galactose residues in the $\alpha 1$ configuration. Staining was not inhibited with sugars having a terminal galactose in a $\beta 1 \rightarrow 4$ configuration. These results demonstrate the specificity of the antibody binding and the ability of appropriate sugars to inhibit such binding.

Reactivity of anti-GAL antibodies with cultured pig cells was confirmed using tissue sections of pig organs. Again, using a fluorescent signal antibody system, staining was seen with total anti-GAL IgM+IgG and with purified anti-GAL IgG but not with the anti-GAL antibody-depleted sera. Staining was particularly-strong with kidney, heart and liver endothelium, with heart endocardium and with bile duct epithelium. The tissue binding was inhibited with melibiose but was not inhibited by other disaccharides not representative of the GAL epitope.

These data clearly indicate that the GAL epitope is expressed at high levels on the endothelial cells of arteries, veins and capillaries of porcine kidney, heart and liver. In a xenograft situation, the endothelial cells of these vessels come into direct contact with the anti-GAL antibodies in human serum. The above results are consistent with evidence that binding of these antibodies (with attendant complement activation) is a key component of the hyperacute rejection response.

To further investigate the specificities of naturally occurring xenoantibodies in human serum directed against porcine antigens, the ability of human serum to cause agglutination of pig red blood cells was investigated. These studies revealed the presence of high levels of such antibodies in human serum. Moreover, sugars such as melibiose, stachyose, galactose and fucose, having terminal residues in the $\alpha 1$-6 configuration, were found to inhibit agglutination in the μM to mM range. Sugars with other configurations were only inhibitory at very high doses, where the observed effects are likely due to simple changes in osmolarity or other non-specific mechanisms.

The above investigations establish a potential role for naturally occurring, human anti-GAL xenoantibodies in the complement-mediated destruction underlying hyperacute rejection. However, it is preferable to directly examine complement-mediated destruction of porcine cells in order to confirm the specificity of the GAL epitope and of anti-GAL antibodies in the process of lysis. To this end, the present inventors have examined the ability of human serum to cause lysis of porcine cells.

To investigate complement-mediated destruction of cells, it is necessary to employ one or more assays that provide quantitative data on cell lysis. Preferably, such assays measure a cell-sequestered component that is released into the medium upon complement-mediated cell lysis. Such experiments should control for involvement of complement in the induced lysis by employing both native complement proteins as well as heat-inactivated complement. The present inventors have used a $^{51}$Cr-release assay and a lactate dehydrocenase (LDH)-release assay to investigate the complement-mediated lysis of porcine epithelial and endothelial cells by human serum.

In the $^{51}$Cr-release assay, porcine cells were pre-labeled with $^{51}$Cr and then incubated in the presence of heat-inactivated human serum plus rabbit complement (PAE's) or human complement in non-heat-inactivated normal human serum ($PK_1$'s). Release of $^{51}$Cr into the medium was measured with a gamma counter following addition of scintillation fluid. In the LDH-release assay, cells were labeled with LDH as per the manufacturer's instructions (Promega, USA). Release of LDH into the medium was measured using an ELISA format, with absorbance read at 492 nm. For both assays, the ability of various sugars to inhibit the complement-induced lysis was also tested.

Similar results were obtained with the two unrelated porcine cell lines, PAE and $PK_1$, using both types of assays. The results clearly demonstrate that naturally occurring xenoantibodies (NXAb's) are responsible for initiating the complement-induced lysis of porcine-cells. The present inventors have also established that IgM and not IgG antibodies are responsible for the lysis in this system. Moreover, heat inactivation of the complement preparations prevented lysis, providing further evidence that lysis of the porcine cells is a complement-dependent phenomenon. The present inventors have also shown that melibiose, but not lactose, protects the porcine cells from lysis. Importantly, the concentrations of sugar found to be effective in these studies covered the physiological range of blood sugar, i.e., about 10 mM.

These results indicate that the anti-GAL NXAb's in normal human serum are primarily responsible for lysis of the porcine cells. As such, the binding of anti-GAL NXAb's to the endothelial cells lining the blood vessels of a porcine xenograft, with attendant activation of the complement cascade, is likely to be a key component of the hyperacute rejection of porcine xenografts. This would also be the case with organs from other discordant species, such as rodents, sheep, cows and goats, all of which have active α-1,3-GalT genes in their genomes.

These conclusions are further supported in a whole-organ study performed by the present inventors. For this study, isolated and perfused rat hearts were used to further demonstrate the involvement of anti-GAL xenoantibodies in hyperacute rejection. Rat hearts were connected to a Langendorf perfusion apparatus, as described in Doring and Dehnert, The Isolated Perfused Heart According to Langendorf, Bionesstechnik-Verlag March GmbH, D7806, West Germany. The connected hearts were then stabilized by perfusion with a physiological buffer system, and perfused with the same buffer containing either melibiose or lactose (10 mM). Human plasma was then added to a final concentration of 13% and the effect of the added sugar on heart rate, strength of contraction and output were measured.

These results demonstrate in a whole-organ system that:

1) Perfusion with unmodified human plasma causes rapid loss of function.

2) Perfusion of a rat heart with human plasma in the presence of melibiose, which competes for binding with the anti-GAL antibodies, prolongs heart survival and output. Lactose, however, which does not compete for binding with the anti-GAL antibodies, does-not prolong heart survival.

3) Perfusion of a rat heart with anti-GAL antibody-depleted plasma prolongs heart survival and output.

4) If purified anti-GAL antibodies are added back to anti-GAL antibody-depleted plasma, the heart rapidly loses function The present inventors' experiments with cultured cells, tissues and whole organs provide important confirmation that anti-GAL antibodies are a critical element in the hyperacute rejection response. Moreover, the disclosed results point to various approaches that can be employed to eliminate or reduce the hyperacute rejection of xenogeneic mammalian organs by humans.

For example, the intravenous administration of the specific disaccharide galactose α 1-3 galactose will block the naturally occurring anti-GAL antibodies of all classes and prevent them binding to their specific epitopes on the surface of the endothelial cells of the xenograft, thus preventing them from initiating or participating in hyperacute rejection. The present inventors' results indicate that the concentration of galactose α 1-3 galactose required to achieve this effect is in a physiologically tolerated range. The experiments also indicate that various other carbohydrates can be substituted for the specific disaccharide. These include the monosaccharide galactose and various other di-, tri- or tetra-saccharides in which there is a terminal α galactose linked to the next sugar via position 1. These other sugars include, but are not limited to, melibiose and stachyose.

Likewise, prior to xenotransplantation, all or a substantial portion of total IgM (that is, IgM of all specificities) can be removed from the serum of the patient by extracorporeal immunoabsorption. Alternatively, anti-GAL antibodies of all classes can be removed by extracorporeal immunoabsorption. Most preferably, the patient's pre-formed natural anti-GAL IgM antibodies can be removed. In this way, many or most of the primary immunological agents of the hyperacute response are eliminated, resulting in reduction or elimination of the response following xenotransplantation.

The α-1,3-GalT Gene as a Target for Suppressing the GAL Epitope

The present inventors have succeeded in cloning the entire coding region of the porcine α-1,3-GalT gene. This is desirable for full exploitation of the gene in genetic engineering of pigs for purposes of human xenotransplantation. Previous attempts to obtain the entire coding region of the porcine gene have, to the knowledge of the inventors, failed to generate the 5' coding regions. See, e.g., Dabkowski et al., Transplant. Proc. 25: 2921 (1993). The present inventors have employed a PCR-based approach to generate the full sequence. In designing the primers and experimental conditions-required to obtain the 5' and 3' regions of the gene, the present inventors overcame significant theoretical and practical obstacles to success.

Primers were selected on the basis of careful analysis of published sequences for the murine, bovine and human α-1,3-GalT genes, the only published sequences available for this purpose. The present inventors' analysis revealed that in the reported sequence of the bovine cDNA, exon 3 (which is in the 5'-untranslated region) is missing. This had not been reported in the literature. Thus, in order to find appropriate regions for deriving useful primer sequences, the mouse and bovine sequences had to be realigned. Even with the appropriate realignment, however, only one island of about 20 base pairs (bp) in the 5' untranslated region displayed the desired homology (19 out of 20 bp) for design of a PCR oligonucleotide. The fact that the 5' untranslated regions of the mouse and bovine genes do not seem substantially related even upon optimal alignment would not be considered unusual by the ordinary skilled artisan. This is because the 5' untranslated regions are often not well conserved between species. As such, the natural inclination would be to perform a less-than-exhaustive analysis and to conclude that design of PCR oligonucleotides based on homology from this region was unlikely to be successful.

In the downstream 3'-untranslated region, the homology is less than obvious again. Various insertions and deletions had to be made in order to obtain proper alignment of the mouse and bovine sequences. Moreover, to obtain a region of appropriate homology for design of PCR oligonucleotides, it was necessary to select a region approximately 200 bp downstream of the stop codon. Finally, to get the 5' and 3' primers to work properly, the present inventors found it necessary to drop the annealing temperature by 9° C. These technical and theoretical hurdles to successful use of a PCR-based approach were overcome by the present inventors and allowed the entire coding sequence to be determined.

Analysis of the nucleotide sequence indicates that a counterpart to murine exon 3 in the 5' untranslated region is not found in the porcine gene. The porcine sequence is similar to the bovine sequence in this regard. Analysis of the amino acid sequence demonstrates that the structure of the porcine α-1,3-GalT is similar to that of other glycosyltransferases, and in particular is closely related to bovine and murine α-1,3-GalTs. In each of these enzymes a short cytoplasmic amino-terminal domain of about 6 residues precedes a hydrophobic membrane-anchoring domain (extending from residues 7 to 22). The stem region, which serves as a flexible tether, and the catalytic domain, which catalyses the synthesis of α-1,3-GAL linkages, are located in the lumen of the Golgi and extend from amino acid 23 to the carboxyl terminus at amino acid 371. The precise boundary between the stem and catalytic domains is not well-defined. Based on the suggested characteristics of the stem region, it appears to be the least conserved region and is rich in glycine and proline residues. Paulson and Colley, J. Biol. Chem. 264: 17615 (1989); Joziasse et al., J. Biol. Chem. 267: 5534 (1992). The stem/catalytic boundary may occur around amino acid 60.

To generate constructs for inactivating genes by homologous recombination, the gene is preferably interrupted within an appropriate coding exon by insertion of an additional DNA fragment. Upon analysis of the full-length porcine nucleic acid sequence, the present inventors have identified exons 4, 7, 8 and 9 as preferred locations for disruption of the gene by homologous recombination. However, identification of these exons as preferred sites should not be construed as limiting the scope of the present invention, as interruptions in exons 5 and 6 may be useful in particular cell types or in situations where less-than-complete inhibition of α-1,3-GalT gene expression is desired. Moreover, regulatory elements associated with the coding sequence may also present useful targets for inactivation.

In a preferred embodiment, a Sal1 site located within exon 9 of the mouse α-1,3-GalT gene at codons 221–222 is chosen as the site for disruption of the murine coding sequence. For disruption of the porcine sequence, it is noted that the amino acids encoded by the corresponding porcine nucleotides are conserved, although the Sal1 site is not. In a preferred embodiment for inactivation of the porcine gene, a Sal1 site is engineered into the corresponding location of the pig sequence for convenient construction of a knockout sequence. Sal1 cuts only rarely in genomic DNA. Since multiple restriction sites can be a problem in manipulating large fragments of DNA, the presence of a Sal1 site in the exon is very useful since it is not likely that other Sal1 sites will be present at other locations in the knockout constructs.

A gene coding for a selectable marker is generally used to interrupt the targeted exon site by homologous recombination. Preferably, the selectable marker is flanked by sequences homologous to the sequences flanking the desired insertion site. Thomas and Capecchi, Cell 51: 503–12 (1987); Capecchi, Trends in Genetics 5: 70–76 (1989). It is not necessary for the flanking sequences to be immediately adjacent to the desired insertion site. The gene imparting resistance to the antibiotic G418 (a neomycin derivative) frequently is used, although other antibiotic resistance markers (e.g., hygromycin) also may be employed. Other selection systems include negative-selection markers such as the thymidine kinase (Tk) gene from herpes simplex. Any selectable marker suitable for inclusion in a knockout vector is within the scope of the present invention.

However, it is possible that in some circumstances it will not be desirable to have an expressed antibiotic resistance gene incorporated into the cells of a transplanted organ. Therefore, in a preferred embodiment, one or more genetic elements are included in the knockout construct that permit the antibiotic resistance gene to be excised once the construct has undergone homologous recombination with the α-1,3-GalT gene.

The FLP/FRT recombinase system from yeast represents one such set of genetic elements. O'Gorman et al., Science 251, 1351–1355 (1991). FLP recombinase is a protein of approximately 45 kD molecular weight. It is encoded by the FLP gene of the 2 micron plasmid of the yeast *Saccharomyces cerevisiae*. The protein acts by binding to the FLP Recombinase Target site, or FRT; the core region of the FRT is a DNA sequence of approximately 34 bp. FLP can mediate several kinds of recombination reactions including excision, insertion and inversion, depending on the relative orientations of flanking FRT sites. If a region of DNA is flanked by direct repeats of the FRT, FLP will act to excise the intervening DNA, leaving only a single FRT. FLP has been shown to function in a wide range of systems, including in the cultured mammalian cell lines CV-1 and F9, O'Gorman et al., Science 251: 1351 (1991), and in mouse ES cells, Jung et al., Science 259: 984 (1993).

Targeted cells carrying a genomic copy of an antibiotic resistance gene flanked by direct repeats of the FRT are supplied with FLP recombinase by 1) introduction into cells of partially purified FLP protein by electroporation, or 2) transfection with expression plasmids containing the FLP gene. In this way, the antibiotic resistance gene is deleted by action of the FLP recombinase, and cells are generated that contain the inactivated α-1,3-GalT gene and are free of the exogenous antibiotic resistance gene.

Due to the relative infrequency of homologous recombination in targeted cells, most such cells will carry only one inactivated allele of the target gene. That is, the great majority of cells taken through a single round of transformation with an appropriate knockout construct will be heterozygotes. As used herein, the term "transformed" is defined as introduction of exogenous DNA into the target cell by any means known to the skilled artisan. These methods of introduction can include, without limitation, transfection, microinjection, infection (with, for example, retroviral-based vectors), electroporation and microballistics. The term "transformed," unless otherwise indicated, is not intended herein to indicate alterations in cell behavior and growth patterns accompanying immortalization, density-independent growth, malignant transformation or similar acquired states in culture.

Although heterozygous cells can be used in the methods of the present invention, various manipulations can be employed to generate homozygous cells in culture. For example, homozygous cells can be generated by performing a second homologous recombination procedure on cells heterozygous for the inactivated allele. If the knockout construct used in the initial transformation carried the $neo^R$ gene, a second construct may be employed in a second round of transformation in which the $neo^R$ gene is replaced with a gene conferring resistance to a separate antibiotics (e.g., hygromycin). Cells resistant to both G418 and hygromycin can be screened by Southern blots in order to detect any "double knockouts" (i.e., homozygotes). Both antibiotic resistance genes can be removed subsequently in a single procedure using FLP recombinase. By maintaining selection with G418, this approach ensures that the second construct does not simply replace the previously knocked-out allele, leaving the cells heterozygous.

Alternatively, the $neo^R$ gene can be deleted from an original heterozygous cell using FLP recombinase and a second knockout procedure conducted using the original $neo^R$ gene-containing construct. Double knockouts could be detected by Southern analysis. The newly introduced $neo^R$ gene then could be deleted by FLP recombinase. This alternative approach does not allow one to direct the knockout construct specifically to the non-inactivated allele. Nevertheless, screening of appropriate numbers of targeted cells can lead to identification of cells homozygous for the inactivated locus.

Cellular Vehicles for Incorporation of Knockout Constructs

To create animals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by a microinjection. Following pronuclear fusion, the developing embryo may carry the introduced gene in all its somatic and germ cells since the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are hereinafter termed "pluripotent" cells. Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking a functional α-1,3-GalT gene. That is, cultured ES cells can be transformed with a knockout construct and cells selected in which the α-1,3-GalT gene is inactivated through insertion of the construct within, for example, an appropriate exon. In fact, ES cell lines have been derived for both mice and pigs. See, e.g., Robertson, Embryo-Derived Stem Cell Lines. In: Teratocarcinomas and Embryonic Stem Cells: A Practical Approach (E. J. Robertson, ed.), IRL Press, Oxford (1987); PCT Publication No. WO/90/03432; PCT Publication No. 94/26884. Generally these cells lines must be propagated in a medium containing a differentiation-inhibiting factor (DIF) to prevent spontaneous differentiation and loss of mitotic capability. Leukemia Inhibitory Factor (LIF) is particularly useful as a DIF. Other DIF's useful for prevention of ES cell differentiation include, without limitation, Oncostatin M (Gearing and Bruce, The New Biologist 4: 61–65 (1992); personal communication from A. Smith), interleukin 6 (IL-6) with soluble IL-6 receptor (sIL-6R) (Taga et al., Cell 58: 573–81 (1989); personal communication from A. Smith), and ciliary neurotropic factor (CNTF) (Conover et al., Development 19: 559–65 (1993). Other known cytokines may also function as appropriate DIF's, alone or in combination with other DIF's.

As a useful advance in maintenance of ES cells in an undifferentiated state, the present inventors have identified a novel variant of LIF. In contrast to the previously identified forms of LIF which are extracellular, this new form of LIF (hereinafter T-LIF) is intracellularly localized. The transcript was cloned from murine ES cells using the RACE technique, Frohman et al., Proc. Natl. Acad. Sci. USA 85: 8998–9002 (1988), and subjected to sequence analysis. Analysis of the obtained nucleic acid sequence and deduced amino acid sequence indicates that T-LIF is a truncated form of the LIF sequence previously reported in the literature. Expression of the T-LIF nucleic acid in an appropriate host cell yields a 17 kD protein that is unglycosylated. This protein is useful for inhibiting differentiation of murine ES cells in culture. The protein is expected to have a similar activity with porcine cells, since murine D-LIF is effective at inhibiting both murine and porcine ES cell differentiation. The present inventors have also determined the sequence of the human form of T-LIF.

To generate a knockout animal, ES cells having at least one inactivated α-1,3-GalT allele are identified and incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, all of whose cells (including germ cells) carry the inactivated α-1,3-GalT allele. If the original ES cell was heterozygous for the inactivated α-1,3-GalT allele, several of these animals must be bred with each other in order to generate animals homozygous for the inactivated allele.

Although direct microinjection of DNA into eggs does not generate the large numbers of recombination events obtained through transfecting large numbers of cultured cells, nevertheless direct injection of eggs can be a useful approach since this avoids the special manipulations (see above) required to turn a cultured cell into an animal. This is because fertilized eggs are, of course, quintessentially "totipotent"—i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA. For example, for injection of porcine eggs, it is useful to prepare the constructs from DNA isolated from the boar whose sperm are employed to fertilize the eggs used for injection.

Embryos derived from microinjected eggs can be screened for homologous recombination events in several ways. For example, if the GalT gene is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and the resulting piglets analyzed by polymerase chain reaction (PCR) or reverse transcription PCR (RT/PCR) for evidence of homologous recombination.

Characterization of Knockout Animals

Animals having either one (heterozygous) or two (homozygous) inactivated GalT genes are characterized to confirm the expected alterations in gene expression and phenotypic effect. For example, GalT mRNA should be absent from homozygous knockout animals. This can be confirmed, for example, with reverse transcription PCR (RT-PCR) using appropriate GalT-specific primers. In addition, various tests can be performed to evaluate expression of the GAL epitope in homozygous knockout animals. For example, anti-GAL antibodies and $IB_4$ Lectin (which has an exclusive affinity for terminal α-D-galactosyl residues) can be used in various assay or immunohistological formats to test for the presence of the GAL epitope in an array of tissues. As another indication of GAL epitope status, lysis of cells by human serum can be tested through use of a $^{51}$chromium release assay.

EXAMPLE 1

Affinity Purification of Human Anti-GAL Antibodies

Anti-GAL antibodies were purified from normal heat inactivated AB serum (from CS1 Parkville, Victoria, Australia) using the following sets of procedures.

A. Preparation of Total Anti-GAL (IgG+IgM) Antibodies

The following procedures are performed at 4° C.

1. Desalt 15–30 ml serum (in 3 ml batches) by passage through a pre-equilibrated (20 ml application buffer: 20 mM $K_2HPO_4$, 30 mM NaCl, pH 8) Econo Pac 10DG (Bio-Rad, Richmond, USA) column. Alternatively, for large scale preparations, desalt by dialysis exhaustively against application buffer.
2. Wash column with 4 ml aliquots of application buffer. Collect and pool column eluates.
3. Apply pooled desalted serum to a pre-equilibrated (20 ml application buffer) Synsorb 115 (galactosyl-galactose; Chembiomed, Alberta, Canada) or D(+) Melibiose-Agarose (Sigma) affinity column (5 ml–50 ml depending on the yield required).
4. Collect run-through (partially anti-GAL-depleted) and reapply to column. Repeat process 3 times to ensure complete removal of anti-GAL antibodies. The wash-through from the 3rd passage through the Synsorb column is collected and the volume adjusted to the original volume of the serum with phosphate-buffered saline (PBS) pH 7+0.05% azide. This is used as a source of anti-GAL antibody-depleted serum.
5. Wash column with PBS pH 8 until the eluate is protein free (O.D. 280 nm=0).
6. Elute anti-GAL antibodies with 3.5M KSCN, pH 7.5. Collect 4 ml fractions, determine the O.D. 280 and pool peak fractions (usually 1–6).
7. Concentrate anti-GAL antibodies using CF25 ultrafiltration cones (Amicon, Danvers, USA). Add 7 ml of the pooled fractions containing anti-GAL antibodies to spin cone and centrifuge (2,000 RPM, 10 min, 4° C.). Refill cone and recentrifuge until volume is reduced to 3–5 ml.
8. To dilute the KSCN, adjust vol. to 7 ml with PBS and centrifuge (2,000 RPM, 10 min, 4° C.). Repeat process a further 10 times.
9. Remove sample containing anti-GAL antibodies from cone using plastic pipette; rinse cone with PBS pH7+ 0.05% azide.

B. Preparation of IgG Anti-GAL Antibodies

The following procedures are performed at 4° C.
1. Desalt 15–30 ml serum. (in 3 ml batches) by passage through a pre-equilibrated (20 ml application buffer) Econo Pac 10DG (Bio-Rad, Richmond, USA) column. Alternatively for large scale preparations desalt by dialysis exhaustively against application buffer.
2. Wash column with 4 ml aliquots of application buffer. Collect and pool column eluates.
3. Apply desalted serum to a pre-equilibrated (30 ml application buffer) Affi-Blue column (Bio-Rad, Richmond, USA) (Affi-Blue binds all proteins except albumin and IgG).
4. Wash column with 20 ml application buffer to elute IgG enriched fraction.
5. Apply IgG enriched fraction to a pre-equilibrated (20 ml application buffer, pH 8.0) Synsorb 115 (galactosyl-galactose; Chembiomed, Alberta., Canada) affinity column (5 ml).
6. Collect run-through and reapply to column. Repeat process 3 times to ensure complete removal of anti-GAL antibodies. The wash-through from the 3rd passage through the Synsorb column is collected and the volume adjusted to the original volume of the serum with PBS pH 7+0.05% azide. This is used as a source of control anti-GAL-depleted IgG.

In some cases anti-GAL IgG was further purified using a protein G column, which efficiently binds IgG but not other antibody isotypes. IgG was then eluted from the protein G column using glycine pH 2.4.

All anti-GAL antibody preparations were analyzed for the following:
a. Protein content was determined using the Bradford calorimetric method (Bradford, M. M 1976, Anal. Biochem. 72:248–254), using purified human IgG as the standard.
b. Molecular weight and purity were determined using polyacrylamide gel electrophoresis according to method described by Laemli, Nature (London) 227: 680 (1970), and protein was detected in the gels by silver staining using standard kit reagents (Amersham, UK).
c. Antibody class and isotype were determined by radial immunodiffusion using standard techniques as set out in Rose et al. (eds.), *Manual of Clinical Laboratory Immunology*, American Society for Microbiology, Washington, D.C. IgG anti-GAL preparations were found to contain all subclasses, with IgG2 predominating.

EXAMPLE 2

Reactivity of IgG and IgM Anti-GAL Antibodies and Depleted Serum with Porcine Cells and Tissues I. Cells Reactivity of IgG and IgM anti-GAL antibodies was assessed using either porcine aortic endothelial cells (prepared by the inventors as described below) or porcine epithelial cell line LLC $PK_1$ ($PK_1$), obtained from the American Type Culture Collection (ATCC), Accession No. CRL1392.

A. Isolation and Culture of Porcine Aortic Endothelial Cells (PAE's)

Pigs were blood typed (using human typing reagents) to identify "O-type" pigs, i.e, pigs unreactive with antibodies to A or B human red blood cell antigens. Aortas were excised from "O-type" pigs, then transported from the abattoir to the laboratory on ice. PAE's were isolated by collagenase treatment as described by Gimbrone et al., J. Cell Biol. 60: 673–84 (1974). PAE's were cultured in RPMI medium containing 10% fetal calf serum (FCS), supplemented with 150 g/ml endothelial cell supplement (Sigma) and 50 g/ml heparin (Sigma). The cells were identified as endothelial cells by their typical cobblestone morphology and by their immunoreactivity with Factor VIII antibodies, as identified using immunofluorescence. In all the assays described below, the PAE's were used between the 8th and 12th passages.

B. Tissue Culture: Maintenance of PK-1 and PAE Cell Lines

All tissue culture was performed in a laminar flow hood, using appropriate tissue culture sterile technique. All tissue culture reagents, unless otherwise indicated, were purchased from CSL, Melbourne, Australia. Media were constituted as follows:

PK-1 Culture Medium:

| | |
|---|---|
| DMEM (Cytosystems, Castle Hill, Australia) | 500 ml |
| FCS (CSL, Melbourne, Australia) | 37.5 ml |
| Glutamine (200 mM) (Cytosystems) | 5 ml |
| Hepes (1 M) (CSL) | 7.5 ml |
| Penicillin (CSL) | 0.5 ml ($10^5$ U/ml final) |
| Streptomycin (CSL) | 0.5 ml ($10^5$ μg/ml final) |

-continued

| PAE - Culture Medium: | |
|---|---|
| RPMI (CSL) | 90 ml |
| FCS (CSL) | 10 ml |
| Endothelial cell supplement (3 mg/ml) (Sigma) | 1.5 ml |
| Heparin (10 mg/ml) (CSL) | 0.5 ml |

Endothelial cell supplement was purchased from Sigma Chem. Co. (St. Louis, Mo., USA) as a lyophilized powder, resuspended in sterile HBBS, and 3 ml aliquots stored at 4° C.

| Heparin (Sigma, Missouri, USA) (10 mg/ml) | dissolved in PBS |
|---|---|
| (0.22 vm) | filter sterilized |
| Hanks Buffer Cytosystems | purchased from |

The following general procedures were used in propagating the cell lines.
1) Pour off old medium
2) Rinse cells twice with sterile PBS
3) Add 3 ml of TED (0.05 M trypsin, 0.53 M EDTA, Gibco, NY, USA)
4) Incubate 10 min. in $CO_2$ incubator at 37° C.
5) Add 7 ml RPMI with 10% FCS
6) Resuspend cells and transfer to a sterile 10 ml tube
7) Centrifuge for 5 min at 1200 rpm, discard supernatant
8) Resuspend cells in RPMI with 10%. Newborn Bovine Serum (NBS) and repeat centrifugation
9) Resuspend cells in 1 ml DMEM (PK-1's) or RPMI (PAE's) (with additives, as described above).
10) Add 10 ml medium and the appropriate volume of cell suspension to achieve the desired dilution for each 75 $cm^2$ tissue culture flask, and return to humidified $CO_2$ incubator.

C. Antibody Staining and FACS Analysis
1) Add 2 ml TED to a 75 $cm^2$ culture flask containing PK-1 or PAE'S, and incubate at room temperature for 10 min.
2) Add RPMI plus 10% FCS (5 ml) to neutralize trypsin.
3) Pellet cells by centrifugation (700 g, 5 min,
4) Wash cells by resuspension and centrifugation in Hanks Buffer (×2).
5) Pellet cells by centrifugation (700 g, 5 min, 4° C.).
6) Resuspend cell pellet in Hanks buffer containing purified anti-GAL antibodies, GAL-depleted serum or GAL-depleted IgG and incubate at 4° C. for 60 min. All antibodies were used undiluted, or diluted 1:2 or 1:4 in Hanks buffer.
7) Add 1 ml of Hanks Buffer, pellet cells by centrifugation and aspirate off supernatant.
8) Resuspend pellet in FITC-labelled sheep-anti-human IgG Fab2 or IgM Fab2 (Silenus, Hawthorn, Australia) diluted 1:80 in Hanks buffer.
9) Incubate for 30 min. at 4° C.
10) Wash three times with Hanks buffer; resuspend pellet from final wash in 0.5 ml Hanks buffer.
11) Analyze stained samples using a FACScan II (Becton Dickinson) according to the manufacturer's instructions.

The specificity of the anti-GAL antibody binding to porcine cells was determined by examining the ability of sugars of various structures to inhibit antibody binding. In these competition studies the anti-GAL antibodies were pre-incubated with sugar (0.1 M) at 37° C. for 30 min before adding to the cells.

D. Results

Using immunofluorescence it was found that total anti-GAL (IgM & IgG) and purified anti-GAL IgG stained both PK-1 and PAE's cells. On the other hand, neither the total anti-GAL antibody-depleted serum nor the anti-GAL IgG-depleted serum gave-detectable staining over background. The staining with anti-GAL IgM and/or IgG was inhibited with purified galactose and with disaccharides having terminal galactose residues in the α1-configuration such as melibiose (6-O-α-D-galactopyranosyl-D-glucose) and stachyose (α-D-Gal-[1 →6]-α-D-Glc-[1→2]-β-D-Fru). Staining was not inhibited with sugars such as lactose (4-O-β-D galatopyranosyl-α-D-glucose), which has a terminal galactose residue, but in a β1->4 configuration. The results of one such experiment are represented in FIG. 1. PAE's were stained with anti-GAL antibody alone (GAL: PBS) or with anti-GAL antibody that had been pre-incubated with either melibiose (GAL:MELIBIOSE), galactose (GAL: GALACTOSE) or lactose (GAL:LACTOSE). Anti-GAL antibody staining was approximately 10 fold less in the samples:containing melibiose and galactose, but was not affected significantly by lactose.

II. Tissues

A. Methods

Pig kidney was fixed in formalin and dehydrated before embedding in Paraplast. Pig heart and liver were fixed in paraformaldehyde-lysine-periodate fixative and snap frozen in O.C.T. embedding compound (10.24% w/w polyvinyl alcohol, 4.26% w/w polyethylene glycol, 85.50% w/w non-reactive ingredients; Tissue Tek®, Miles, Inc., Elkhart, Ind., USA). Four μm-thick sections of pig heart and liver and 2 μm-thick sections of kidney were incubated with purified anti-GAL antibodies (undiluted, 1:2 and 1:4) for 60 min. and then incubated with a fluorescein isothiocyanate (FITC)-conjugated sheep anti-human immunoglobulin F(ab') fragment. (Silenus Laboratories, Hawthorn, Australia) (1:100) for 30 min. or a peroxidase-conjugated rabbit anti-human IgG (Dakopatts, Glostrup, Denmark) (1:50) for 60 min. Control sections were analyzed for autofluorescence, with the secondary antibody alone, or with the anti-GAL-depleted IgG or normal pig serum as the primary antibody. No staining was detected. The specificity of the anti-GAL antibodies was tested by pre-incubating sections of pig renal cortex with a variety of sugars, including melibiose, lactose, sucrose and glucose at 0.1 M.

B. Results

As with the analyses performed on the pig cells using immunofluorescence, total anti-GAL IgM+IgG, purified anti-GAL IgG, but not the anti-GAL IgM and/or IgG-depleted sera, stained all pig tissues examined. The individual staining parameters varied from organ to organ as set out below:

| Immunostaining of Pig Tissues with Anti-GAL Antibodies: | | |
|---|---|---|
| Tissue | Anti-GAL Reactivity | Staining Intensity |
| Kidney | Proximal and distal convoluted tubules | Variable |
| | Endothelium: Intertubular sinusoids | Variable |
| | Endothelium: Arteries and veins | Strong |
| | Glomerular capillaries | Variable |

-continued

| Tissue | Anti-GAL Reactivity | Staining Intensity |
|---|---|---|
| Heart | Endothelium: Arteries, veins, capillaries | Strong |
| | Endocardium | Strong |
| | Myocardium | Perinuclear |
| Liver | Small Bile Ducts (lining cells) | Strong |
| | Endothelium: Arteries, veins | Strong |
| | Intertubular sinusoids | Negative |

Immunostaining of Pig Tissues with Anti-GAL Antibodies:

The specificity of the binding of anti-GAL antibodies was tested on sections of pig renal cortex by inhibition with 0.1 M melibiose, lactose, sucrose and glucose. Reactivity of the anti-GAL antibodies with proximal tubule brush borders was reduced to near background by preincubation of antibody with melibiose, but was not inhibited by the other saccharides.

EXAMPLE 3

Hemagglutination of Pig RBC by Human Serum: Sugar Inhibition Studies

The methods used to investigate the hemagglutination of pig red blood cells (RBC's) by human serum was adapted from the methods described by Galili, J. Exp. Med. 160: 1579–81 (1984) and Severson, Immunol. 96: 785–789 (1966).

I. Methods
  A. Media/Solution Preparation
    1. Human Serum Albumin (HSA) (CSL, Melbourne, Australia) (5 mg/ml) was dissolved in PBS, filter sterilized, and stored at 4° C.
    2. Preparation of sugars:
       1 M stock solutions of sugar were prepared by dissolving the amount indicated in 100 ml of PBS. Sodium azide was added (0.02%) and solutions stored at 4° C.

| | |
|---|---|
| α-Lactose (4-O-β-D.galactopyranosyl-α-D-glucose | 36.0 g |
| D(+)galactose | 18.0 g |
| Stachyose (α-D-gal-[1->6]-α-D-Glc-[1->2]-β-D-Fru) | 66.6 g |
| Melibiose (6-O-α-D-galactopyranosyl-D-glucose) | 34.2 g |
| Sucrose (α-D-Glucopyranosyl β-D-fructofuranoside) | 34.2 g |
| D-(+)-Glucose | 18.0 g |
| α-D-(+)-Fucose (6-Deoxy-D-galactopyranose) | 16.4 g |

All sugars were purchased from Sigma (St. Louis, Mo., USA). Sugar solutions were diluted in PBS to the appropriate concentration as required.
  B. Preparation of Pig RBC'S
    1. Heparinised pig blood (Animal Resources, Clayton, Australia) is centrifuged at 800 RPM for 10 min to pellet the RBC.
    2. The RBC pellet is washed by resuspension in PBS (10 ml) and recentrifugation (repeated 3 times). After the final wash, the RBC pellet is resuspended in 10 ml PBS.
    3. A 0.5% solution of RBC's is prepared by adding 50 ul RBC solution (from step 2, above) to 10 ml PBS containing 0.5 g/100 ml of HSA.
  C. Preparation of 96-well Microtitre Plates (Titretek. USA)
    1. Add 25 ul of PBS to each well.
    2. Add 25 ul of pooled human AB serum (CSL, Melbourne, Australia) to column 1 and serially dilute by removing 25 ul from column 1 and adding to column 2, then repeating by sequentially removing and adding 25 ul from and to each well across the plate, finally discarding 25 µl from column 11 and adding no serum to column 12.
    3. Add 25 ul of sugar solution to each row in decreasing concentrations down rows. No sugar solution is added to the final row.
    4. Incubate at 4° C. overnight and then at 37° C. for 30 min.
    5. Add 50 ul of 0.5% pig RBC to each well; vortex and incubate at room temperature for 2 hours. Determine agglutination visually.

II. Results
Human serum caused the agglutination of pig RBC's at a titre of between $1/32$–$1/64$, which is consistent with the presence of high levels of naturally occurring xenoantibody (NXAb) in human serum. To examine the specificity of the NXAb response, sugar inhibition studies were performed. Sugars such as melibiose, stachyose, galactose and fucose which have terminal galactose residues in the α1-6 configuration were found to inhibit agglutination in the µM to mM range. Sugars with other structures, such as lactose and sucrose, were only inhibitory when very high concentrations were used. At these high concentrations, the observed effects are most probably non-specific, due, for example, to changes in osmolarity. Results are summarized below:

Pig RBC Hemagglutination by Human Serum: Sugar Inhibition

| Sugar | Linkage | Inhibitory Concentration |
|---|---|---|
| Melibiose | Gal α1-6Glc | $5 \times 10^{-4}$M |
| Stachyose | Gal α1-6Gal | $2 \times 10^{-3}$M |
| Galactose | | $2 \times 10^{-3}$M |
| Fucose | 6-Deoxy-α-L-Gal | $1 \times 10^{-3}$M |
| Lactose | Galβ1-4-Glc | $>10^{-1}$M |
| Sucrose | α-D-Glc-β-D-Fruc | $>10^{-1}$M |

EXAMPLE 4

Inhibition of Human Serum-Induced Lysis of Porcine Cells by Sugars

The ability of human serum to cause the lysis of porcine cells was examined using both pig epithelial ($PK_1$) and aortic endothelial (PAE's) cells, the isolation and culture of which is described in Example 2. Cell lysis was determined using either the $^{51}$Chromium release assay as described by Cerottini and Brunner, Nature New Biol. 237:272, 1972 or the Cytotox LDH release assay according to the manufacturer's instructions (Promega, USA).

I. Methods
  A. $^{51}$CR Release Assay
    1. Preparation of Cells:
       a) Trypsinize a confluent flask of cells. On average, approximately $3 \times 10^6$ PAE's and approximately $3 \times 10^7$ $PK_1$ cells are obtained per 10 ml flask. About $1 \times 10^5$ cells are required for each well in the 5CR Release Assay.
       b) Wash cells 0.4 times in 10 ml RPMI (no FCS); spin 1200 rpm for 5 min.
       c) Resuspend cells in 100 µl RPMI (with 10% heat-inactivated FCS; see below).

2. Labelling Cells with $^{51}CR$:
   a) Combine in a 10 ml tube: Cells in 195 μl RPMI/10% FCS (heat inactivated); 5 μl 51CR (120 μCi).
   b) Incubate at 37° C. for 2 hr.
   c) Add 2 ml RPMI/10% FCS (heat inactivated).
   d) Centrifuge cells through a layer of FCS (heat inactivated) to remove excess label.
   e) Gently overlay the labelled cells onto a 4 ml cushion of FCS using a Pasteur pipette.
   f) Centrifuge at 700 g for 5 min. at 4° C.
   g) Remove supernatant taking care not to disturb the cell pellet.
   h) Resuspend pellet in RPMI/10% FCS (heat inactivated) at about $3 \times 10^7$ cells/ml.
3. Assay Conditions:
   a) For PAE'S, rabbit complement was used as the complement source, since the $^{51}$CR-release assay was not sufficiently sensitive to detect lysis when human complement, a less "active" source, was used. In contrast, with the LDH assay, which is significantly more sensitive, normal human serum (NHS) was used as the source of complement.
   b) To each test well of a 96-well V bottom plate, add:
   100 μl labelled cells
   10–50 μl NHS (heat inactivated) (5–25% of final)
   Complement:
      PAE'S: 50 μl absorbed rabbit complement (25% final)
      $PK_1$: 10–40 μl NHS (5–25% of final)
   50 μl antibody (total anti-GAL (IgG+IgM), anti-GAL IgG, anti-GAL antibody-depleted serum, or anti-GAL antibody-depleted IgG)
   c) Adjust volume to 200 μl with RPMI/10% FCS (heat inactivated) if required
   d) Incubate plates at 37° C. for 3 hr.
   e) Centrifuge plates at 1000 rpm for 5 min to pellet cells
   f) Remove 100 μl of supernatant from each well and transfer to a gamma counter tube
   g) Add 3 ml scintillation fluid and measure $^{51}CR$ release using a gamma counter (Packard Instrument Company, Illinois, USA)
   (To determine maximum release, add 100 μl 8% Triton X-100 made up in RPMI/10% FCS (heat inactivated) to 100 μl labelled cells)
   (Note: Each reaction is set up in quadruplicate)
4. Calculation of % Lysis:

% Lysis=Experimental cpm−Spontaneous Release cpm×100

Max. Release cpm−Spontaneous Release cpm

5. Sugar Inhibition of Complement-Induced Cell Cytotoxicity:
In a 96-well test plate, mix the following:
50 μl labelled cells
50 μl complement (PAE's: pig spleen cell absorbed complement; $PK_1$'s: NHS)
xμl sugar (final concentration of sugar: $10^{-1}$ to $10^{-3}$ M)
yμl NHS (heat inactivated)—final concentration 5–20%)
make volume to 200 μl with RPMI

| Plate Layout: | | | | |
| --- | --- | --- | --- | --- |
| | Plate 1 | | Plate 2 | |
| | 5% | 10% | 15% | 20% |
| Rows: | 1–4 | 5–8 | 1–4 | 5–8 |
| Columns: | 1. Spontaneous Release | | | |
| | 2. Maximum Release | | | |
| | 3. Melibiose | | | |
| | 4. Lactose | | | |

B. LDH Release Assay
1. General Procedures:
   a) Prepare cells as for $^{51}$CR Release assay, and labeled with LDH as per the manufacturer's instructions (Cytotox non-radioactive LDH release assay, Promega, USA)
   b) To each well of a 96-well plate add (each reaction set up in quadruplicate):
   25 μl labeled cells
   5–20 μl NHS
   x μl sugar (final concentration of sugar: $10^{-1}$ to $10^{-3}$ M)
   RPMI/10% FCS (heat inactivated), to total volume of 100 μl
   c) Incubate plates at 37° C. for 3 hr.
   d) Centrifuge plates at 1500 rpm for 5 min.
   e) Remove 50 μl supernatant from each well (taking care not to remove any cells) and transfer to ELISA plate containing 50 μl substrate mix (prepared according to manufacturer's instructions
   f) Cover tray and incubate in the dark at room temperature for 30 min.
   g) Add 50 μl stop solution to each well using multichannel pipette
   h) Read absorbance at 492 nm.
2. Controls:
   a) Spontaneous release (no antibody or complement)
   25 μl labeled cells
   75 μl RPMI/10% FCS (heat inactivated)
   b) Maximum release
   25 μl labeled cells
   50 μl 16% Triton X-100
   25 μl RPMI/10% FCS (heat inactivated)
3. Calculation of % Lysis:

% Lysis=Experimental release−(Spontaneous release cpm+sugar cpm)×100

Maximum release−(Spontaneous release cpm+sugar cpm)

4. Experimental Design:

| | Plate 1 | | |
| --- | --- | --- | --- |
| Columns: | 1. spontaneous release | Rows: | 1–4: cells + no sugar |
| | 2. maximum release | | 5–8: no cells + no sugar |
| | 3. 5% serum | | |
| | 4. 10% serum | | |
| | 5. 25% serum | | |
| | 6. RF10 alone | | |
| Plate 2 | melibiose | | |
| Plate 3 | galactose | | |
| Plate 4 | lactose | | |
| Plate 5 | sucrose | | |

-continued

Plate 1

Plates 6–9 same as plates 2–5 but no cells added

Sugar Conc.

| Columns: | | | Rows: | | |
|---|---|---|---|---|---|
| 1–2 | $1 \times 10^{-1}$M | | | 1–2 | 0% serum |
| 3–4 | $5 \times 10^{-2}$M | | | 3–4 | 5% serum |
| 5–6 | $1 \times 10^{-2}$M | | | 5–6 | 10% serum |
| 7–8 | $5 \times 10^{-3}$M | | | 7–8 | 25% serum |
| 9–10 | $2 \times 10^{-3}$M | | | | |
| 11–12 | $1 \times 10^{-3}$M | | | | |

5. Preparation of Pig Spleen-Absorbed Rabbit Complement:
   a) Cut pig spleen (obtained from local abattoir) into small pieces and prepare a single-cell suspension by passage through a fine metal sieve
   b) Pellet cells by centrifugation at 700 g, 7 min. at 4° C.
   c) Resuspend cell pellet in RPMI/10% FCS and repeat centrifugation
   d) Resuspend in RPMI/10% FCS/10% dimethylsulfoxide (DMSO)
   e) Count cells and store frozen aliquots ($3 \times 10^9$ cells/aliquot)
      use one aliquot for each absorption
   f) For absorption, thaw and centrifuge at 600 g, 5 min. at 4° C. and remove the supernatant containing the DMSO
   g) Wash two times with RPMI/10% FCS (10 ml)
   h) Resuspend the cell pellet in rabbit complement; mix (rotary wheel) 2 hr. at 4° C.
   i) Centrifuge 600 g, 5 min. at 4° C. and remove the supernatant containing the rabbit complement; store at 4° C.

II. Results

Figure 2:
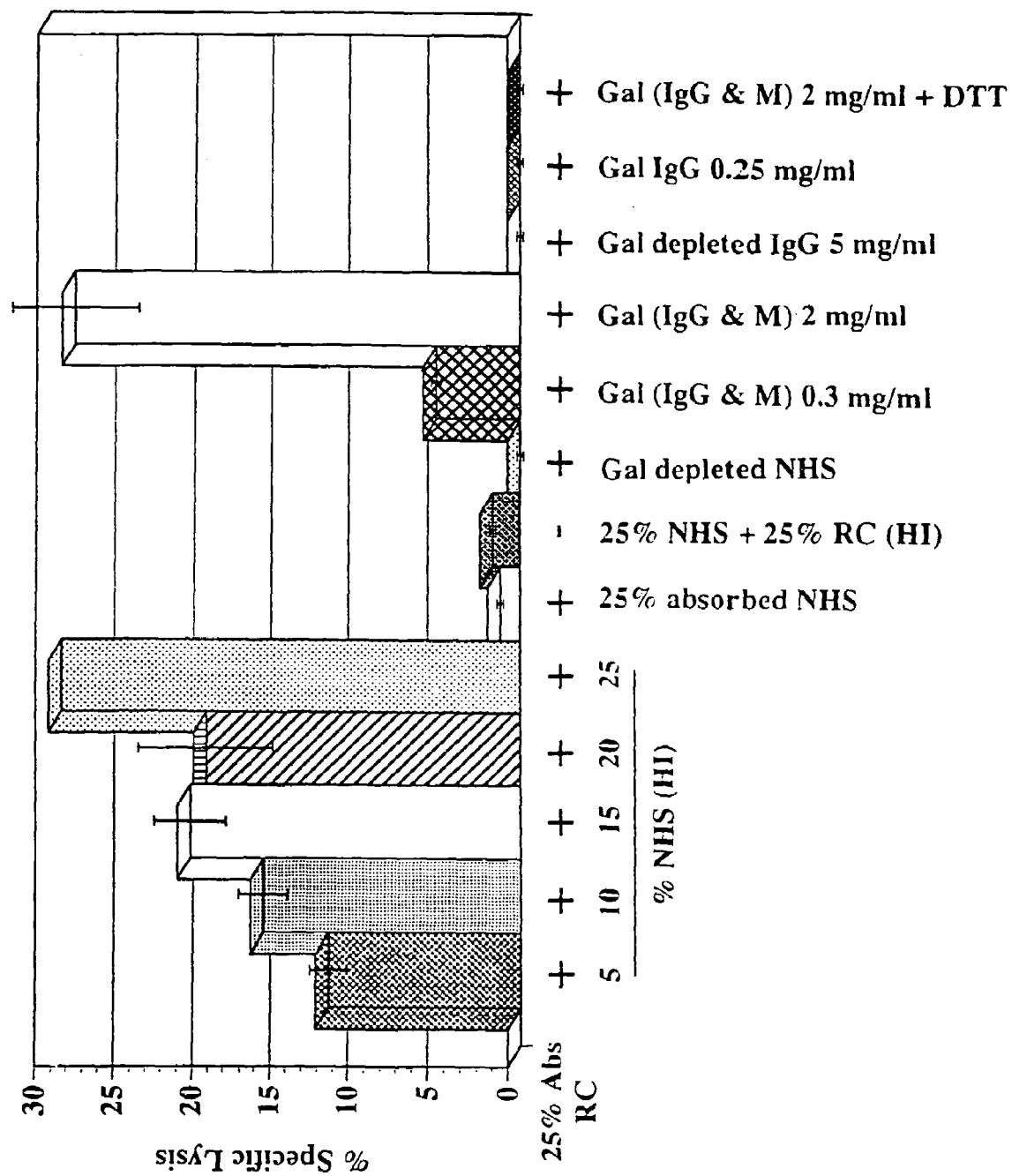
FIG. 2 shows the results of an experiment in which lysis of porcine aortic endothelial cells by human serum and by purified anti-GAL antibodies was determined using a $^{51}CR$ release assay.

Comparable results were obtained with both cell types (PAE's and $PK_1$'s) using both lysis assays. The results of a typical lysis experiment are represented in FIG. 2, in which the lysis of PAE's by human serum and by purified anti-GAL antibodies was determined using the $^{51}$CR release assay. Comparable results were also obtained with $PK_1$ cells using the $^{51}$CR release assay and with both cell lines using the LDH release assay. The results of these assays can be summarized as follows:

1. Xenoantibodies (NXAb) in human serum in the presence of complement are capable of lysing porcine cells. Lysis increases with increasing concentrations of serum.
   2. Pre-absorption of NHS with pig spleen cells (which removes the NXAb): No lysis.
   3. Use of heat-inactivated complement: No lysis.
   4. Use of NHS depleted of anti-GAL antibodies: No lysis.
   5. Use of purified total anti-GAL antibodies (IgG+IgM): Lysis.
   6. Use of purified anti-GAL IgG: No lysis.
   7. Use of purified total anti-GAL antibodies (IgG+IgM) and dithiothreitol (DTT): No lysis. (DTT is a reducing agent that disrupts the multimeric structure of IgM antibodies without affecting IgG.)

Together these results demonstrate that the anti-GAL antibodies are responsible for the observed lysis. Purified anti-GAL IgG and DTT-treated total (IgG+IgM) anti-GAL antibodies failed to elicit lysis, indicating that IgM, but not IgG, antibodies are causative agents in this system. Preliminary attempts to verify this observation using purified IgM prepared either in crude form by euglobulin fractionation or by α-IgM affinity chromatography were unsuccessful. The inventors believe this reflects inactivation of the IgM during preparation, rather than a true reflection of the capacity of anti-GAL IgM to cause lysis of porcine cells heat inactivation of the complement prevented lysis, indicating that lysis of porcine cells is a complement-dependent phenomenon.

The effect of adding the disaccharide sugars melibiose (Gal α1→6 Gal) and lactose (Gal β1→4 Glu) on the lysis of PAE's by human serum was assessed using the Cytotox non-radioactive LDH release assay. PAE's were incubated in the presence of 50% human serum as the source of xenoantibody and complement, together with various concentrations of each sugar (1 mM to 100 mM). Under these conditions, melibiose, which has the Gal α1→6 Gal configuration, but not lactose, which has the terminal Gal moiety by in a β1→4 configuration, protected the pig cells from lysis.

EXAMPLE 5

Inhibition of Human Serum-Induced Damage to Rat Hearts by Sugars

The Langendorf isolated perfused ex vivo heart model was used to further demonstrate the involvement of anti-GAL xenoantibodies in hyperacute rejection.

I. Methods
   A. Preparation and Storage of Human Plasma
      1. Centrifuge fresh human blood at 3000 rpm, 10 min., 4° C. to remove red blood cells (RBC's)
      2. Remove the plasma
      3. Centrifuge the plasma at 10,000 rpm, 10 min. 4° C. to remove any remaining cells; decant the plasma
      4. Add 2.5 ml of 0.1M EDTA pH 7.30 for every 50 ml of plasma
      5. Store 50 ml aliquots at −70° C.
      6. For heat-inactivated plasma, heat at 56° C. for 60 min., then centrifuge at 2,500 rpm for 10 min.
   B. Assessment of Complement Activity
      Before being used in the ex vivo model, both heat inactivated and control plasma was tested for complement activity. Classical complement activity was determined by hemolysis using sensitized sheep RBC's as described by Harrison and Lachman, In: Weir et al. (eds.), *Handbook of Experimental Immunology and Immunochemistry*, 4th Ed., Blackwell scientific Publications (1986). Alternative complement pathway activity was determined using the rabbit hemolytic assay as described by Serrais et al., J. Immunol. Meth. 140: 93–100 (1991). The assay was performed in buffer containing EGTA and $MgCl_2$. The EGTA chelates the $Ca^{++}$ thus inhibiting the classical pathway. The $Mg^{++}$ is required for activation and assembly of CdbBb, the alternative pathway C3 convertase.
   C. Preparation of Plasma for Heart Perfusions
   Plasma prepared from different blood packs is thawed at 37° C., pooled and filtered (100 μm steel mesh, 8.0 μm and 4.5 μm Millipore filters, sequentially). $Cacl_2$ is added at 0.58 mg/ml plasma, and the plasma kept on ice until ready for perfusion.
   D. Ex Vivo Isolated Perfused Rodent Heart Model
      1. Anesthetize rats with Nembutal (1 μl sodium pentobarbitone (60 mg/ml)/g body weight) and mice with ether.

2. Surgically expose the heart and inject heparin (Porcine Mucous, 10,000 U/ml) into the femoral vein (rats: 0.3 ml injected).
3. Remove heart and place in ice-cold Krebs-Henseleit buffer containing heparin (0.2 ml/50 ml buffer.
   Krebs-Henseleit buffer:
   119 mM NaCl
   25 mM $NaHCO_3$
   4.6 mM KCl
   1.2 mM $MgSO_4.7H_2O$
   1.3 mM $CaCl_2.2H_2O$
   1.2 mM $KH_2PO_4$
   11 mM glucose
   0.25% (v/v) BSA
   Adjust to pH 7.4; store at 4° C.
4. Connect aorta to the canula of the Langendorf perfusion apparatus and tie firmly. The apparatus was assembled by the present inventors according to experimental requirements of the Langendorf heart model as described in Doring & Dehnerrt, The Isolated Perfused Heart According to Langendorf, Bionesstechnik-Verlag March GmbH, D7806, West Germany.
5. Perfuse with Krebs-Henseleit buffer (made fresh each day), which is gassed continuously with carbogen (95% $O_2$, 5% $CO_2$) at a pressure of 100 mmHg, at 37° C.
6. Attach a hook, connected to a transducer (Physiograph MK-111-S, Narco Bio-Systems) to the apex of the heart.
7. Perfuse heart for 20 min. with Krebs-Henseleit buffer to enable heart to stabilize (reservoir volume: 270 ml).
8. Add plasma (pre-warmed to 37° C.) as follows:
   at 20 min.—add 10 ml plasma (=5% plasma)
   at 25 min.—add 10 ml plasma (=9% plasma)
   at 30 min.—add 10 ml plasma (=13% plasma)
9. Monitor heart for a further 30 min. and record heart flow and contraction rate.

E. Sugar Perfusion
1. Stabilize heart in Krebs Henseleit buffer for 30 min. as described above.
2. Add 2.5 ml of 1.08 M stock sugar solution to reservoir; total volume=270 ml; final sugar concentration=10 mM.
3. Allow heart to restabilize for 10 min, then add plasma (control or heat inactivated) as per the schedule described above.
4. Record heart beat and flow rate.

F. Large-Scale Preparation of Anti-GAL Antibody-Depleted Plasma
(all manipulations are performed at 4° C.)
1. Start with 200 ml freshly prepared human plasma; 100 ml is subject to depletion; 100 ml is used as an untreated control from the sam patient drawn on the same day; store at 4° C.
2. Filter the plasma sequentially through a 100 µm, 8 µm metal sieves and finally through a 0.45 µm Millipore filter; dilute to 1000 ml with PBS, pH 8.0.
3. Concentrate to 200 ml using an Amicon spiral wound cartridge (removes salt).
4. Equilibrate melibiose sepharose column (40 ml) with PBS, pH 8.0 (10 column volumes).
5. Passage the plasma through the melibiose sepharose column; collect the run-through and store at −70° C. (=partially depleted plasma).
6. Wash column with PBS, pH 8.0 (10 column volumes) until the O.D. (280 nm) of the eluate is approximately zero.
7. Combine the partially depleted plasma and the eluate from the wash; concentrate to 200 ml (Amicon spiral concentrator).
8. Elute the anti-GAL antibody fraction with 4 M guanidinium HCl pH 6.4 (2 column volumes).
9. Regenerate the column with PBS (10 column volumes).
10. Repeat the entire process an additional two times, i.e., repassage plasma through the melibiose column, wash, elute the anti-GAL antibody fraction and regenerate column.
11. For the anti-GAL antibody-depleted fraction:
    combine the eluate from the melibiose sepharose column with run-through from the final wash
    adjust the volume to 5 liters with Krebs Henseleit buffer and add EDTA to 10 mM; adjust pH to 7.0
    concentrate back to original volume (Amicon spiral concentrator); aliquot (35 ml) and store at −70° C.
12. For the anti-Gal antibody fraction:
    combine the eluted anti-GAL antibody fractions, dilute to 5 liters with Krebs Henseleit buffer and add EDTA to 10 mM
    concentrate back to 10 ml (Amicon spiral concentrator); aliquot (1 ml) and store at −70° C.
13. The anti-GAL antibody-depleted fraction and the purified anti-GAl antibody fraction are tested for
    a) Anti-GAL reactivity: Use as primary reagents to stain porcine cells ($PK_1$'s). Detect staining as described in Example 2, above. Analyze stained samples using a FACScan II (Becton Dickinson), according to the manufacturer's instructions.
    b) Protein content: Determine using the calorimetric method of Bradford, Anal. Biochem. 72: 248–54 (1976), with purified human IgG as the standard.
    c) Electrolyte concentration: On the day of the perfusion, the anti-GAL antibody depleted plasma is also tested to determine the calcium, magnesium and potassium levels using an electrolyte autoanalyser (Olympus); the levels of each are adjusted to normal as required.

II. Results
Rat hearts were connected to the Langendorf apparatus and then stabilized by perfusion with Krebs Henseleit buffer for 10 min., and then a further 10 min. with the same buffer containing either melibiose or lactose (10 mM). Human plasma was then added in stages as described above to a final concentration of 13% and the effect of the added sugar on cardiac function was assessed. The parameters measured were heart rate, amplitude (strength) of contraction and output (FIG. 3).

In the presence of human serum alone (lower trace), the heart essentially stopped beating within minutes. The same result was obtained if lactose was added. In the presence of melibiose (upper trace) or anti-GAL antibody-depleted plasma, however, the heart was able to maintain a strong beat. When the purified anti-GAL antibody was added back to the anti-GAL antibody-depleted plasma, the heart again stopped beating within minutes.

EXAMPLE 6

Characterization of the Porcine α-1,3-GalT Gene cDNA's encoding porcine α-1,3-GalT were generated by Polymerase Chain Reaction (PCR) technology. Total RNA of pig liver was isolated by homogenizing liver slices in. 7 M guanidinium thiocyanate, as described by Chomczynski & Sacchi, Anal. Biochem 162, 156–159 (1987); Sambrook et al., *Molecular Cloning: A Laboratory Manual* (2nd Edition), Cold Spring Harbor Laboratory Press (1989). Sixteen μg of the RNA, together with 1 g oligo dT primer, were heat denatured for 5 minutes at 65° C. prior to being transcribed into cDNA using avian myeloblastosis virus (AMV) reverse transcriptase in a 100 μl reaction carried out at 37° C. for 90 minutes. Three μl of the cDNA synthesis reaction was used in the subsequent PCR amplifications. General procedures used for generation of cDNA are provided in Sambrook et al (1989), supra.

Primers for PCR were synthesized using phosphoramidite technology, on an Applied Biosystems DNA synthesizer. The sequence of the PCR primers was based on identifying conserved regions within the published sequences for murine and bovine α-1,3-GalT genes. Joziazze et al., J. Biol. Chem 264: 14290–97 (1989); Joziazze et al., Biol. Chem 267: 5534–5541 (1992). All primers were synthesized with EcoR1 linkers at the 5' end for ease of cloning. In the following listing of the primers used in the present study, nucleotide positions varying between bovine and murine sequences are single-underlined; nucleotide positions varying between bovine and human sequences are double-underlined:

Exon 2 primer (forward): 5'-GTGAATTCAGCCCTGC-CTCCTTCTGCAG-3' (SEQ ID NO: 1)
   Designation: GTE2F—28-mer
     1 difference b/w bovine & murine
     no sequence available for human exon 2

Exon 4 primer (forward): 5'-GTGAATTCAG-GAGAAAATAATGAATGTC-3' (SEQ ID NO: 2)
   Designation: GTE4F—28-mer
     no differences b/w bovine, murine & human Exon 9 primer (reverse): 5'-GTGAATTCGGGA TCTGCCTTGTACCACC-3' (SEQ ID NO: 3)
   Designation: GTE9R—28-mer
     3 differences b/w bovine & murine
     1 difference b/w bovine & human 3'-UTR primer (reverse): 5' GTGAATTCGAAATCACTG GGAATTTACA-3' (SEQ ID NO: 4)
   Designation: GT3UR—28-mer
     no differences b/w bovine & murine
     no differences b/w bovine & human Exon 9 primer (forward): 5'-AGGAATTCAGCATGATG CGCATGAAGAC-3' (SEQ ID NO: 5)
   Designation: GTE9F—28-mer
     no differences b/w bovine & murine
     3 differences b/w bovine & human PolyA primer (reverse): 5'-TTGAATTCTTTTTTTTTTTTV*N**-3' (SEQ ID NO: 6)*V=A or C or G; **N=A or C or G or T (primer includes all nucleotide variants for V and N)
   Designation: APATR—23-mer The PCR conditions used to generate porcine α-1,3-GalT cDNA fragments were as follows:

1) For GTE2F+GTE9R and GTE4F+GTE9R: heat to 94° C. (60 seconds); then proceed with 35 reiterations (cycles) of the following three steps: (1) 94° C., 40 seconds, (2) 57° C., 50 seconds, and (3) 72° C., 80 seconds.

2) For GTE9F+GT3UR: heat to 94° C. (120 seconds); then proceed with 35 cycles of: (1) 94° C., 40 seconds, (2) 48° C., 45 seconds, and (3) 72° C., 60 seconds.

The PCR fragments were subcloned into EcoR1-restricted pBluescript II KS+ (Stratagene, Cat. # 2 12206) and the DNA sequence was determined using the chain termination method. The DNA sequence was assembled and analyzed using DNASIS-Mac v2.01 (Hitachi)

The nucleotide sequence of porcine α-1,3-GalT (SEQ ID NO: 7) and the derived amino acid sequence (SEQ ID NO: 10) of the enzyme are shown in FIGS. 4 and 5. A single large open reading frame extends from the initiating methionine at nucleotide 91 to a stop codon located at nucleotide 1204. The sequence surrounding the putative initiating methionine conforms to the consensus eukaryotic initiation sequence. Kozak, Cell 44, 283–92 (1986).

The porcine cDNA sequence is compared to the corresponding murine (SEQ ID NO: 9) and bovine (SEQ ID NO: 8) sequences in FIG. 4. The locations of introns within the murine gene are also shown. Joziazze et al., J. Biol. Chem 267: 5534 (1992). This alignment demonstrates that exon 3, located within the 5' untranslated region of the mouse gene, is not found in either the porcine or bovine cDNAs. The overall sequence identities between the coding sequences are as follows:
   a) pig compared to mouse:—75.02% (exon 3 not considered)
   b) pig compared to bovine:—85.15%

The amino acid sequences of the porcine (SEQ ID NO: 10), murine (SEQ ID NO: 12) and bovine (SEQ ID NO: 11) α-1,3-GalT enzymes are depicted in FIG. 5. The locations of introns are also shown, based on their positions within the mouse gene (Joziasse et al., 1992). This alignment illustrates that the overall amino acid homologies are:
   a) pig compared to mouse: 71.98%
   b) pig compared to bovine: 82.87%
   c) bovine compared to mouse: 73.72%

EXAMPLE 7

Identification of Potential Sites to Interrupt the α-1-3-GalT Gene

The present inventors' choice of a site for interrupting the α-1,3-GalT gene has been influenced by several characteristics of the gene and its expression. In particular, several mRNAs for α-1,3-GalT have been detected in the mouse. Joziazze et al., J. Biol. Chem. 267: 5534 (1992). These mRNAs are products of alternative splicing events in which exons 5 and/or 6 may be deleted. Hence, these exons are not appropriate interruption sites in the mouse, since a transcript encoding a functional α-1,3-GalT enzyme presumably could be formed when exons 5 or 6 are spliced out. Moreover, the present inventors have isolated two different classes of α-1,3-GalT cDNA clones from the pig—one that includes exon 5 and one with exon 5 deleted. It is possible that mRNA's with and without exon 6 are also formed by alternative splicing in the pig. Thus, for initial experiments the present inventors have not chosen-these exons as sites for interruption.

Insertion of an interrupting-DNA fragment into exon 4 (which encodes the cytoplasmic $NH_2$-terminal domain and the membrane-anchoring domain; see FIG. 5) would disturb production of a transcript encoding an active α-1,3-GalT. Hence this exon is an appropriate site to disrupt the α-1,3-GalT gene. Similarly, exons 7 and 8, which encode the $NH_2$-terminal region of the catalytic domain, are suitable disruption sites. Insertion of a interrupting DNA fragment within these exons would prevent the synthesis of an active catalytic domain.

A preferred site for interrupting the mouse gene is located at a Sal1 site found within exon 9 of the mouse α-1,3-GalT gene, at codons 221+222 (see FIG. 5). This site is positioned 150 amino acids from the COOH-terminus, within the catalytic domain. The mouse gene within the present inventors' constructs for homologous recombination is interrupted at this Sal1 site. The amino acids encoded by nucleotides at this Sal1 site are conserved in the pig and bovine sequences, although the Sal1 site itself is not. Construction of a Sal1 site at this position in the pig gene (e.g., by in vitro mutagenesis) provides a useful construct to inactivate the gene.

EXAMPLE 8

Choice of a DNA Fragment to Interrupt the α-1,3-GalT Gene

The present inventors have used both the neomycin resistance (neo$^R$) gene and the hygromycin resistance gene (hyg$^R$) to interrupt the α-1,3-GalT gene. In one set of "knockout" constructs the neo$^R$ and hyg$^R$ genes are linked to the murine phosphoglycerate kinase (PGK) promoter (Adra et al., Gene 60: 65–74 (1987) and are both bordered by polylinker sequences that include restriction sites for EcoRV and ClaI.

In another construct, expression of the neo$^R$ gene is directed by an altered polyoma virus promoter (PMC1; Thomas and Cappechi, cell 51: 503–12 (1987)). In this construct the present inventors have addressed the problem of including an antibiotic resistance gene within the genome of transplant organs. That is, in some circumstances it may not be desirable to have genes conferring resistance to antibiotics present in the organ to be transplanted. The FLP/FRT recombinase system of yeast has been used to eliminate the neo$^R$ gene from the sequence that interrupts the α-1,3-GalT gene.

In a construct of the present invention, the neo$^R$ gene is bordered at both the 5' and 3' ends by FRT DNA elements. In addition, stop codons for each of three reading frames have been inserted 3' to the neo$^R$ gene, and these stop codons, together with a single FRT sequence, will remain within the α-1,3-GalT gene after the neo$^R$ gene has been excised by FLP. Targeted cells carrying a genomic copy of the neo gene flanked by direct repeats of the FRT could be supplied with FLP recombinase in two ways:

1). Introduction into cells of partially purified FLP protein:

FLP protein (0.1–10 μg) is introduced ("transfected") into approximately 10$^7$ cells using standard electroporation conditions. The cells are plated out into gelatinized tissue culture dishes in appropriate medium, at a sufficient dilution to result in individual colonies. Approximately 200 of these colonies are then picked for further analysis.

2) Transfection with plasmids containing the FLP gene:

A plasmid containing the FLP gene under control of a promoter able to drive FLP expression, e.g., the human interferon-inducible 6–16 promoter, is constructed according to standard methods. Porter et al., EMBO J. 7: 85 (1988). Approximately 10 μg of FLP expression plasmid is transfected into approximately 10$^7$ cells using standard electroporation conditions. With a plasmid containing the human 6–16 promoter, interferon is added at approximately 500 units/ml, in order to induce expression of FLP. The cells are then treated as in (1) above.

The procedure to knock out the α-1.,3-GalT gene in ES cells using an FRT-containing construct is:

a) electroporate the complete construct into ES cells b) select neo$^R$ cells, and identify those ES cells having an interrupted α-1,3-GalT gene c) delete the neo$^R$ gene using FLP recombinase, as described above; cells are tested for the excision event as follows:

First, samples of each selected cell line are tested for the absence of the neo$^R$ gene by treatment with the chemical G418. The cells will die in the presence of approximately 200 μg/ml G418 unless the neo$^R$ gene is still present in the genome. Cell lines that are G418 sensitive are then tested further to confirm that excision of neo$^R$ has occurred. This is done by Southern analysis or PCR analysis, both described in Sambrook et al. (1989). For Southern analysis, genomic DNA is isolated from the cells, digested with an appropriate restriction enzyme, subjected to agarose gel electrophoresis, and the digested DNA transferred to a membrane. The DNA is hybridized with a labeled probe, the label is detected (e.g., with X-ray film or color development), and the pattern of bands indicates whether or not an excision event had occurred in the cell line. For PCR analysis, genomic DNA is isolated from the cells and subjected to PCR reaction with suitable oligonucleotide primers.

d) following confirmation of neo$^R$ excision, the manipulated ES cells or PGC's are used to generate chimeric animals.

EXAMPLE 9

Preparation of DNA Constructs to Interrupt the α-1,3-GalT Gene in Mice

Figure 6:
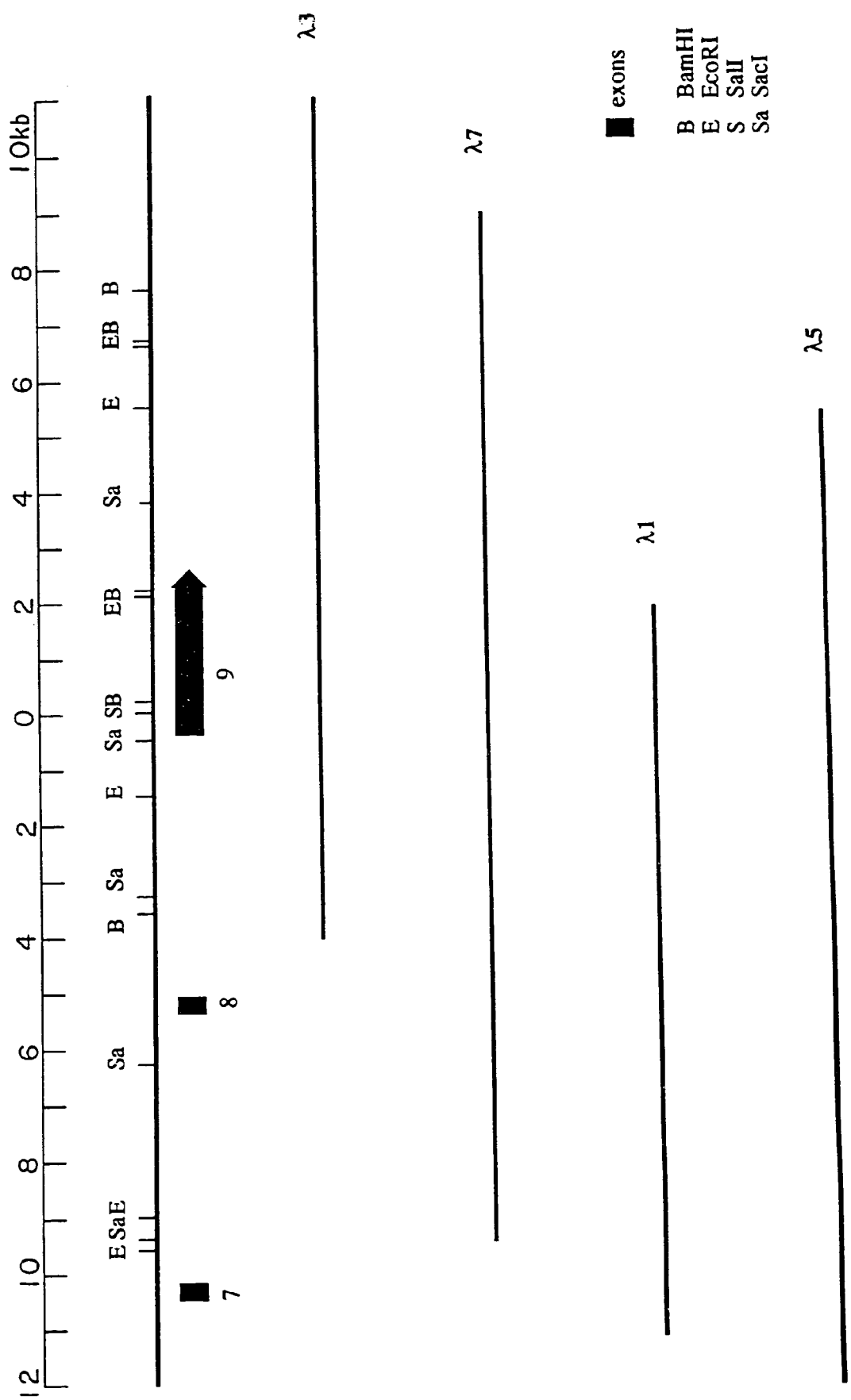
FIG. 6 depicts the Sal1 restriction sites in four overlapping phage clones spanning a portion of the murine α-1,3 galactosyltransferase genomic region.
Figure 7:
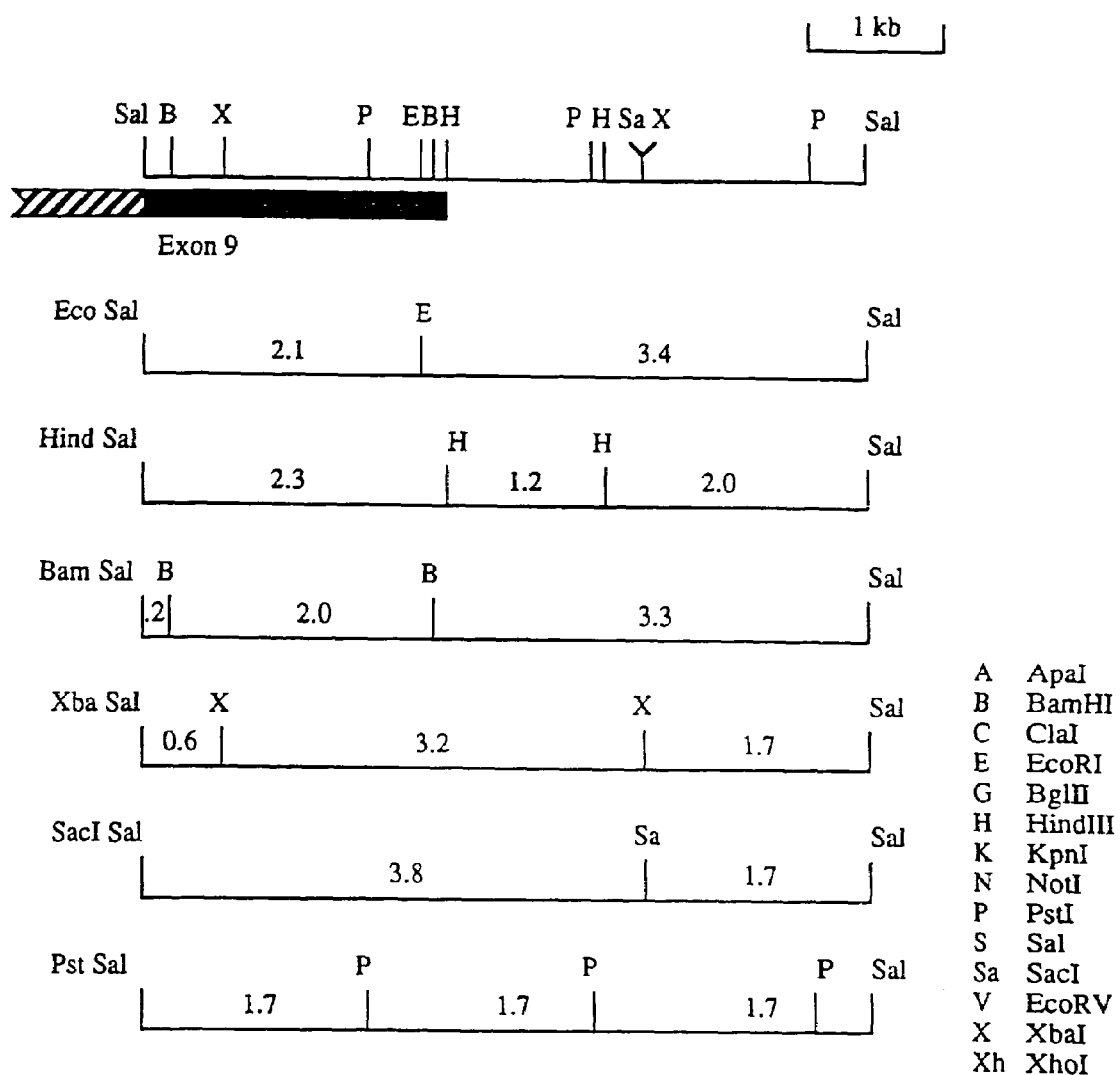
FIG. 7 is a detailed restriction map of murine α-1,3 galactosyltransferase subclone pαGT-S5.5.
Figure 8:
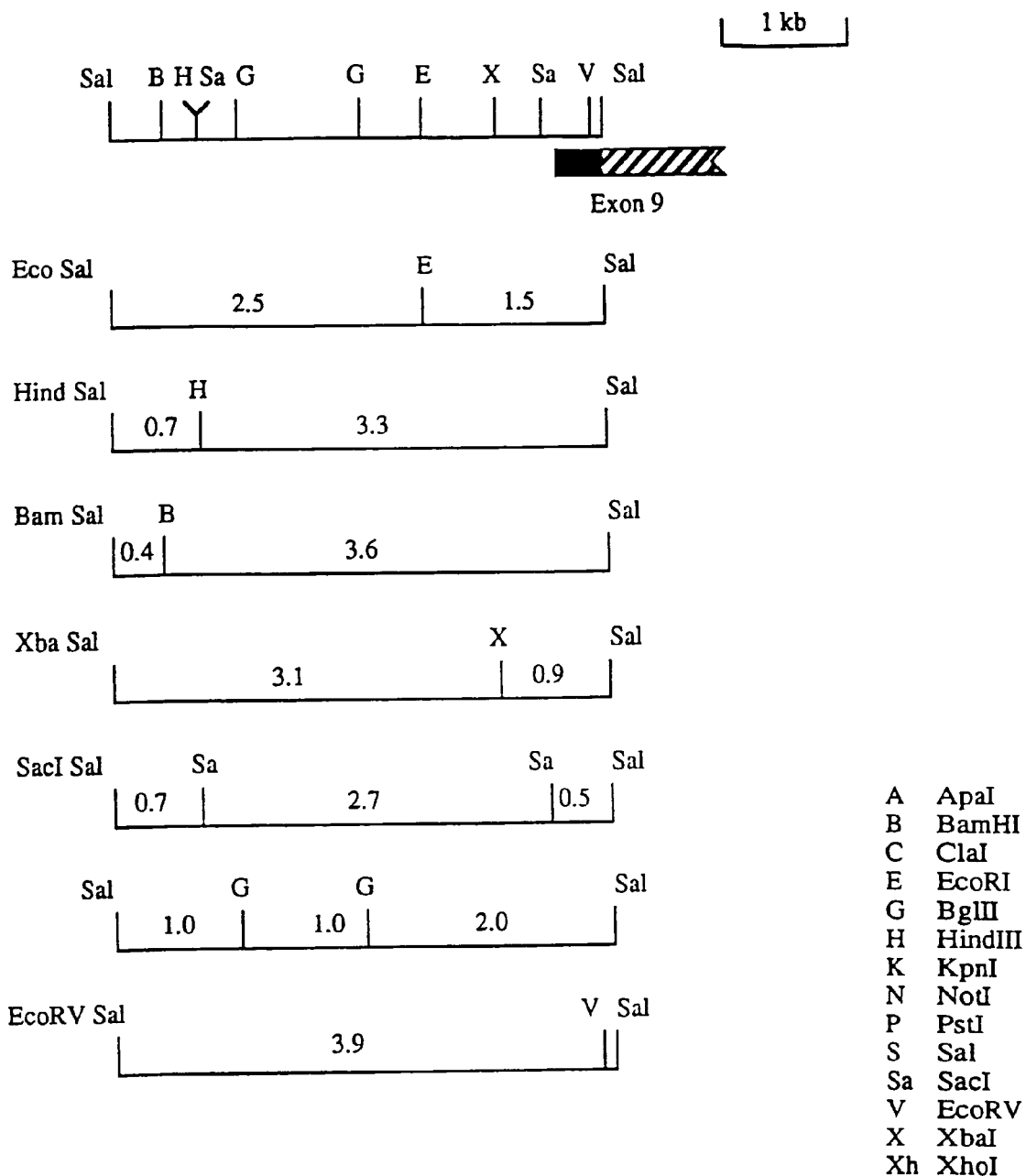
FIG. 8 is a detailed restriction map of murine α-1,3 galactosyltransferase subclone pαGT-S4.0.
Figure 9A:
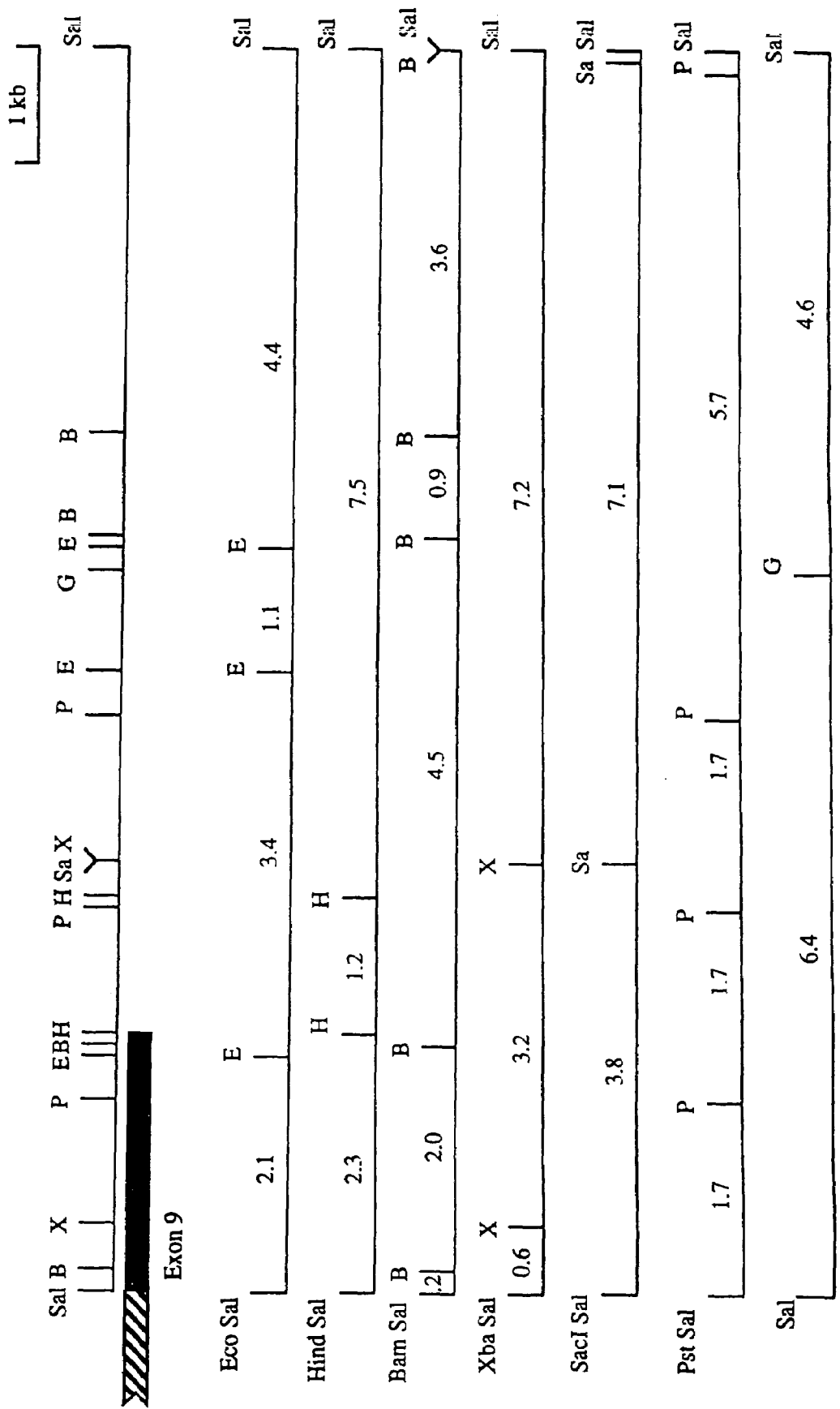
FIG. 9 is a detailed restriction map of murine α-1,3 galactosyltransferase subclone pαGT-S11.
Figure 9B:
Figure 10A:
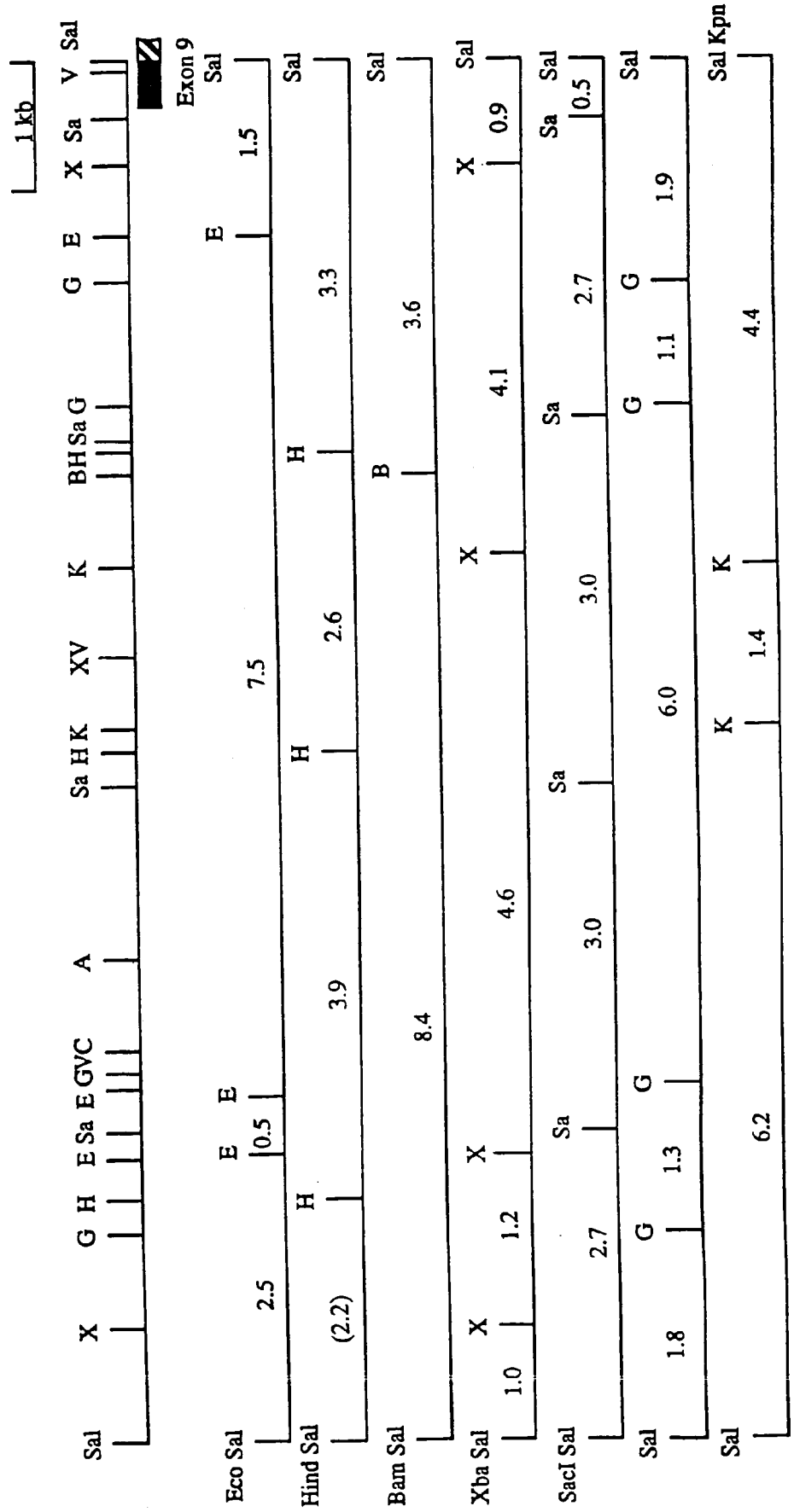
FIG. 10 is a detailed restriction map of murine α-1,3 galactosyltransferase subclone pαGT-S13.
Figure 10B:
Figure 11:
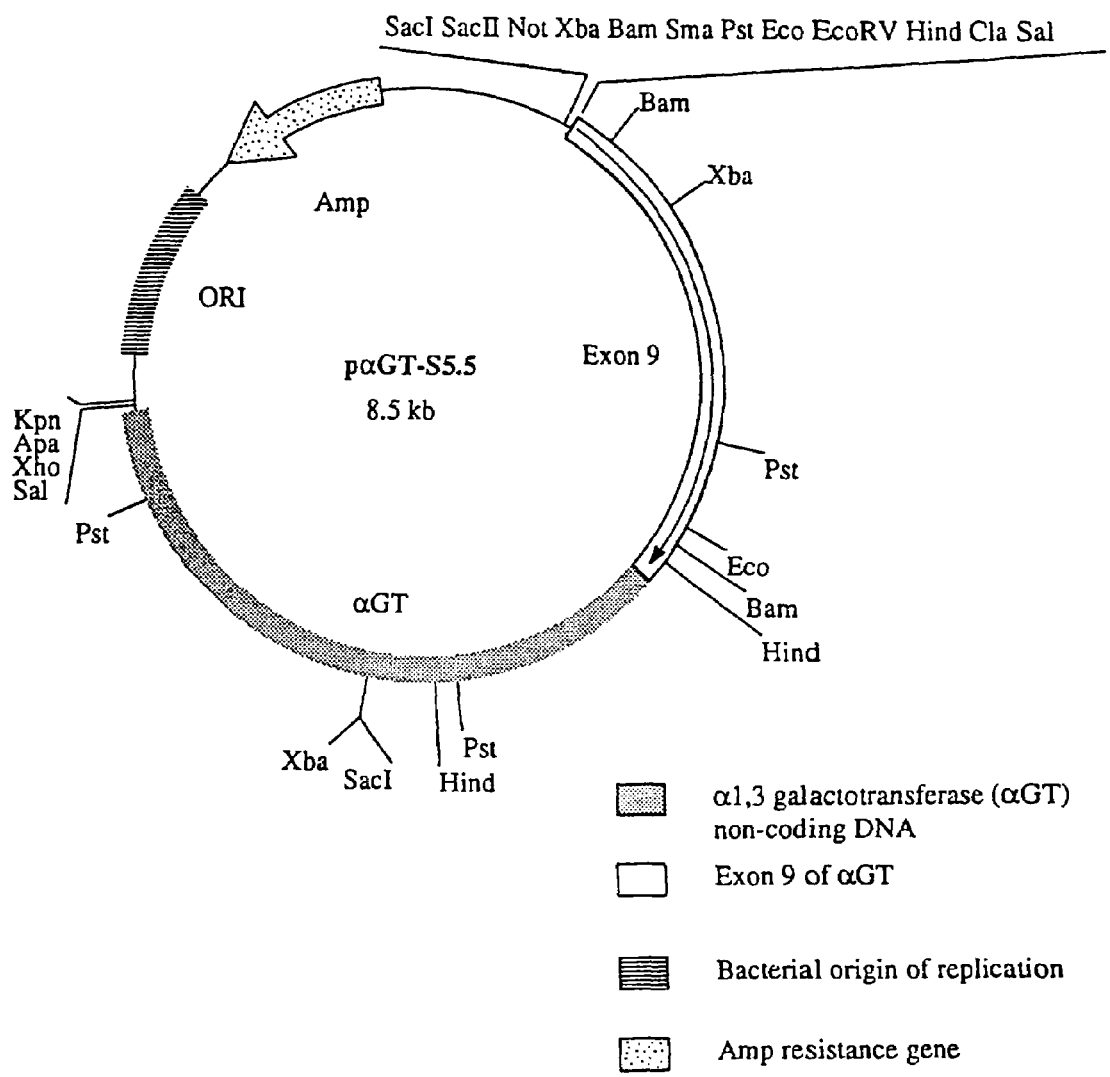
FIG. 11 is an additional detailed restriction map of murine α-1,3 galactosyltransferase subclone pαGT-S5.5.
Figure 12:
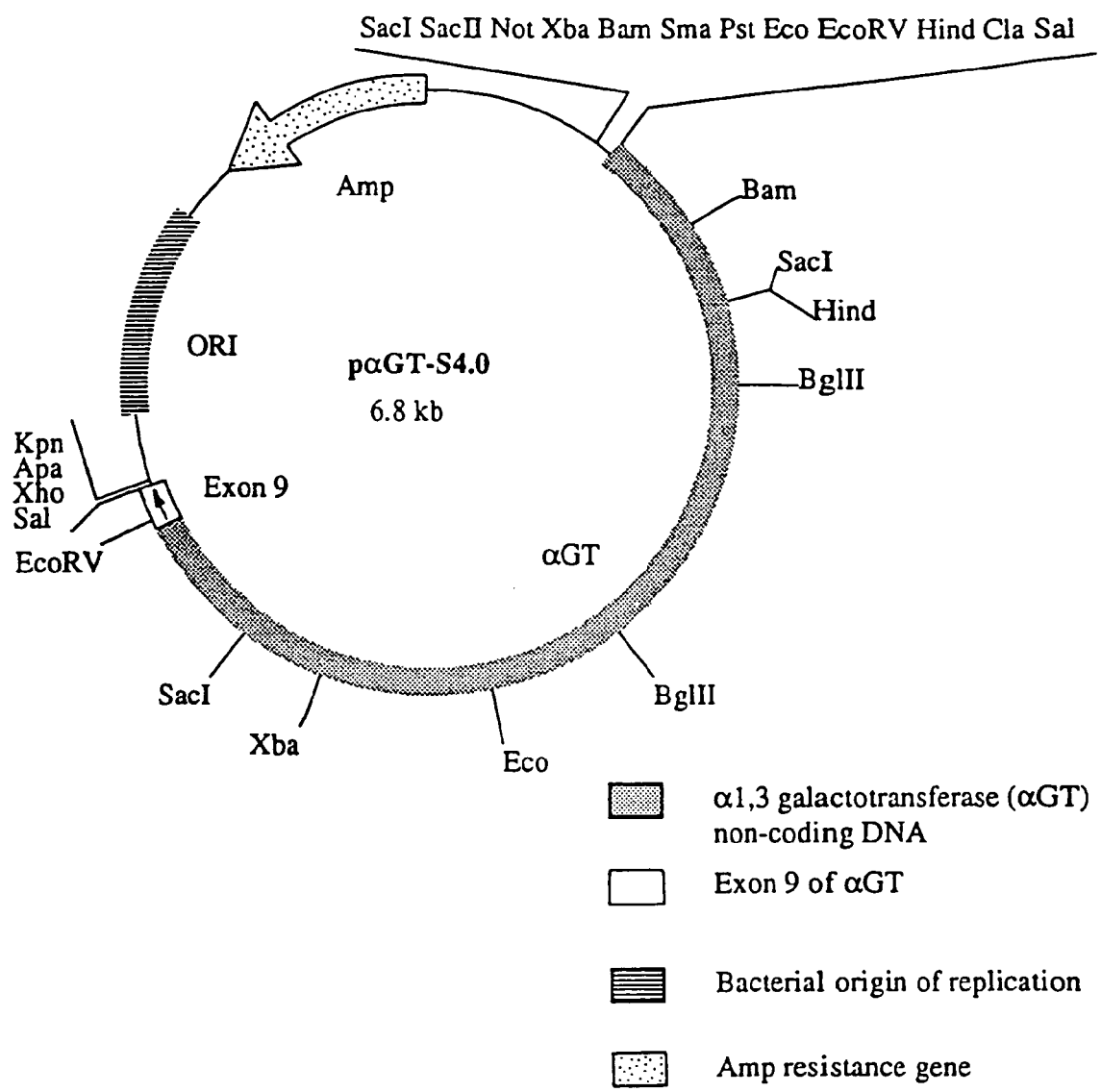
FIG. 12 is an additional detailed restriction map of murine α-1,3 galactosyltransferase subclone pαGT-S4.0.

Gene targeting (homologous recombination) is more efficient if the cloned cDNA fragments used for targeting are isolated from the cell line which is used for the gene knockout (i.e., the DNA is "isogeneic"). Accordingly, DNA was isolated from the E14 ES cell line (Hooper et al., Nature 326: 292–95 (1987)) and used to construct a mouse genomic library. The DNA was digested partially with the restriction enzyme Sau 3A, and fragments 12 kb–20 kb in size were isolated by glycerol gradient fractionation. The size-fractionated DNA was ligated into the Bam H1 site of λEMBL3 (Sambrook et al. 1989, supra), and packaged in vitro to form lambda phage particles. The lambda library was plated by infection of E. coli strain PMC103 host cells (Doherty et al., Gene 124: 29–35 (1993)) at a density of 4×10$^4$ phage per plate. A bovine cDNA clone, about 900 bp in length and containing a portion of the α-1,3-GalT gene corresponding to exons 7–9, was used to probe a total of 5.6×10$^5$ independent recombinant phage. Four overlapping clones containing α-1,3-GalT gene sequences were isolated and purified. The Sal1 restriction sites within these clones were mapped (FIG. 6), and the 4.0 kb, 5.5 kb, 11 kb and 12 kb Sal1 fragments from two of the clones (λ3 and λ5) were subcloned into pBlueScript KS+ (Stratagene) or pUBS (pUC19 carrying the pBlueScript KS+ polylinker) to facilitate further detailed mapping of restriction sites.

These four subclones (designated pαGT-S4.0, pαGT-S5.5, pαGT-S11 and pαGT-S13) were mapped for restriction sites with restriction enzymes BamHI, EcoRI, HindIII, XbaI, XhoI, KpnI SacI, SacII, EcoRV, PstI, SmaI, NotI and BglII. pαGT-S4.0 and pαGT-S5.5 were also checked for PvuI, PvuII, NdeI and SphI restriction sites. Detailed restriction maps of the 4 subclones were drawn from these data (FIGS. 7–12).

Figure 13:
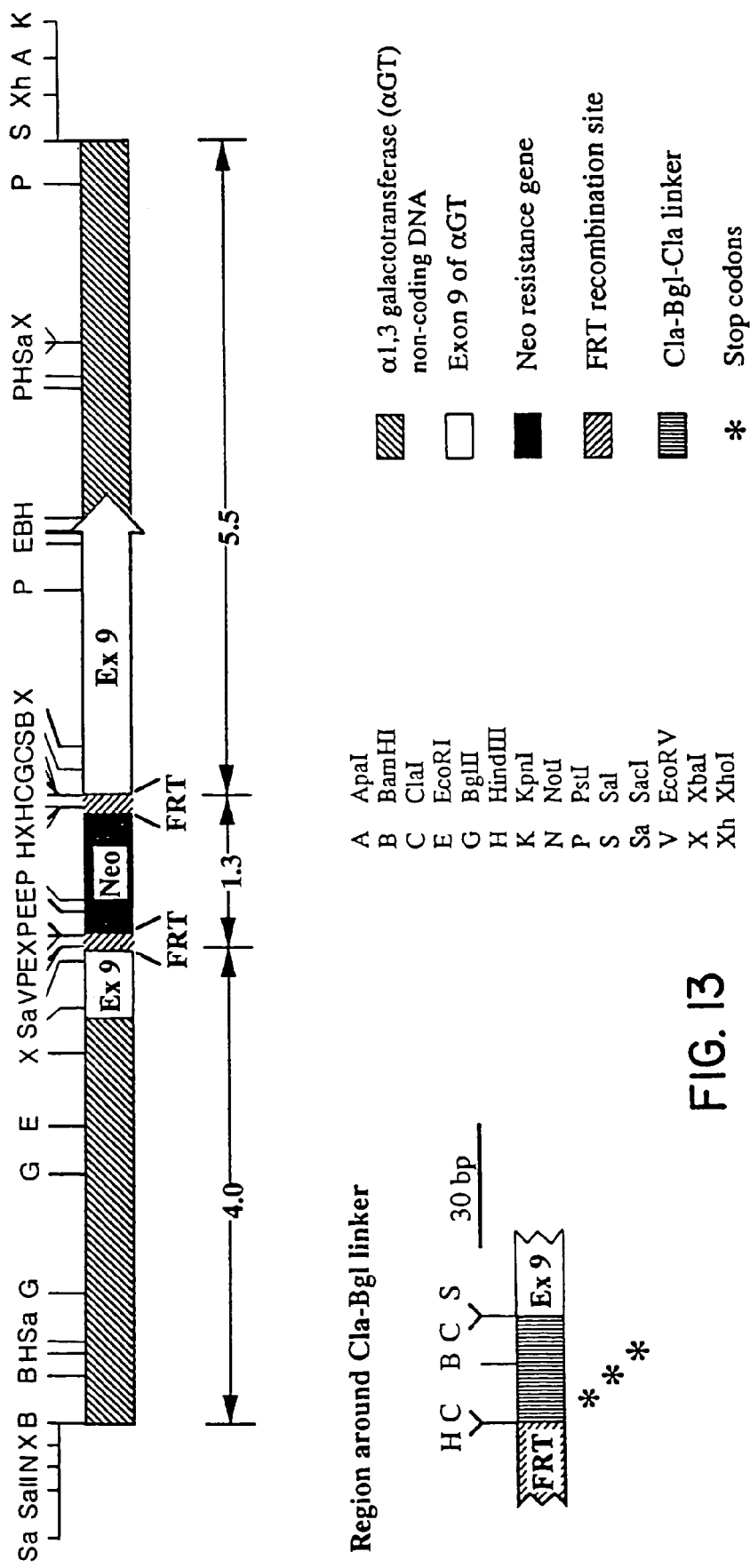
FIG. 13 is a diagram of a knockout construct carrying the 4.0 and 5.5 kb Sal1 fragments from pαGT-S5.5 and pαGT-S4.0, which flank the Exon 9 Sal1 site.
Figure 14:
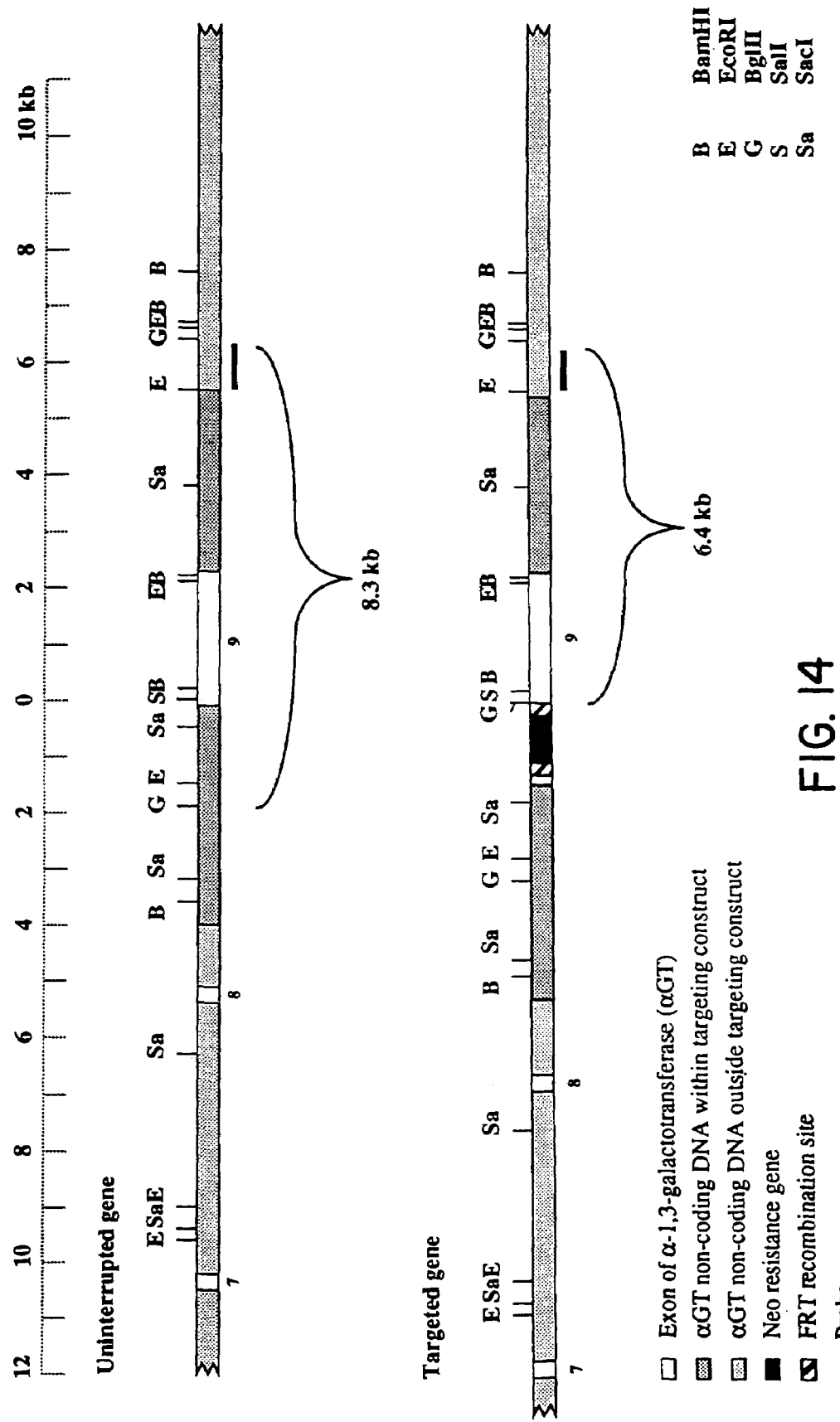
FIG. 14 depicts the 8.3 kb and 6.4 kb BglII fragments that are diagnostic for the uninterrupted α-1,3 galactosyltransferase gene and the targeted (inactivated) α-1,3 galactosyltransferase gene, respectively, using the probes identified in the text.

On the basis of these maps a knockout strategy was conceived. Basically the strategy is to insert a resistance gene (either neo$^R$ or hyg$^R$) into the Sal1 site which lies within Exon 9. The knockout construct carries the 4.0 and 5.5 kb Sal1 fragments from pαGT-S4.0 and pαGT-S5.5 which flank the Exon 9 Sal1 site (FIG. 13). Screening for homologous recombination events then can be carried out using a DNA fragment representing the genomic region but lying outside the DNA included in the knockout construct, i.e., outside the 9.5 kb covered by pαGT-S4.0 and pαGT-S5.5. A 0.7 kb EcoRI/XmnI fragment from pαGT-S11 is used to screen Southern blots of BglII digested ES cell DNA for homologous recombinant events. An 8.3 kb band should appear on these Southerns when the uninterrupted α1,3-GalT gene is probed with this EcoR1/XmnI fragment (FIG. 14). Insertion of the neo$^R$ gene after a homologous recombination event will give rise to a 6.4 kb band, due to the presence of a BglII site just flanking the Exon 9 SalI site within the knockout construct. Thus the presence of the 6.4 kb band is diagnostic for a homologous recombination event.

Figure 15A:
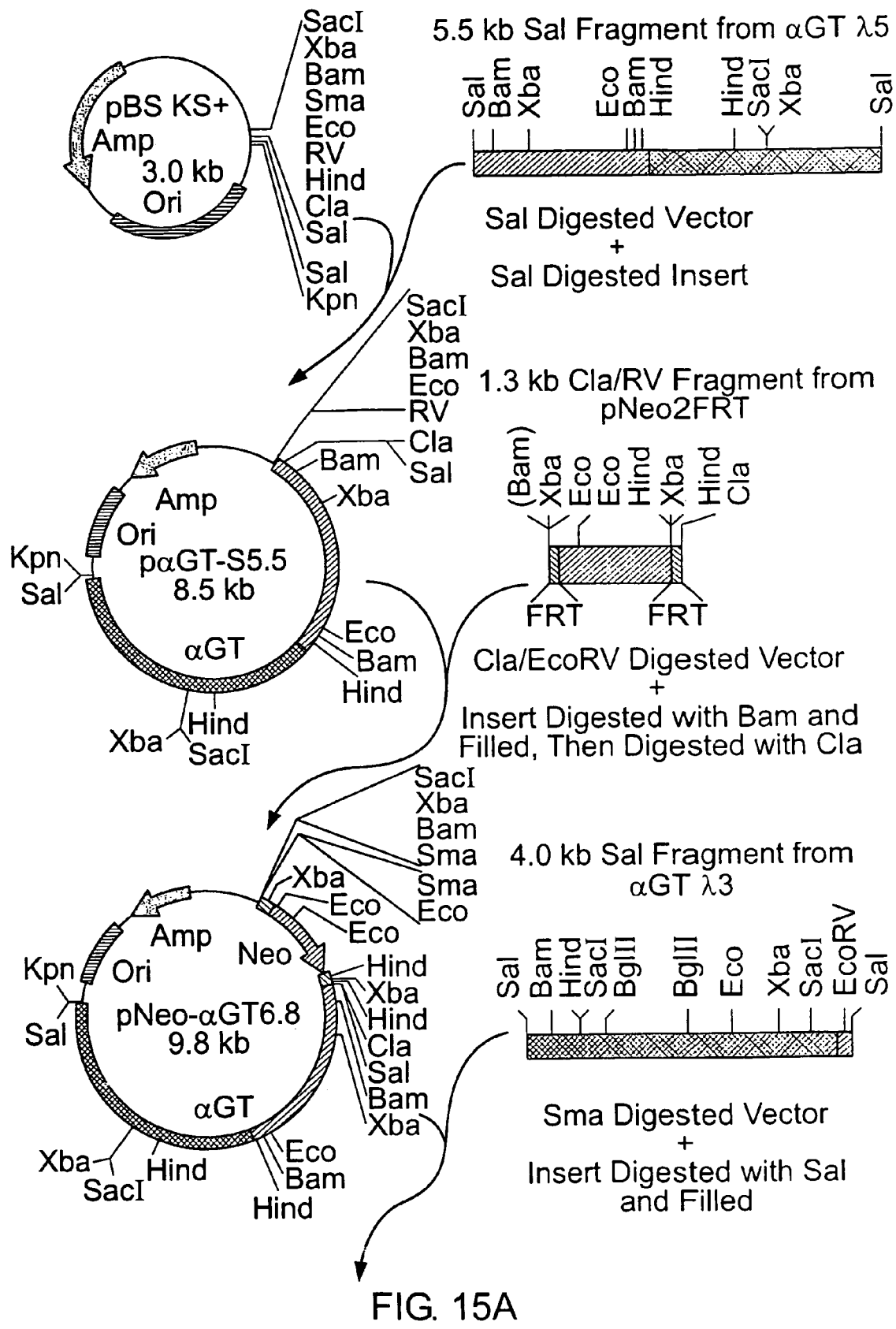
FIG. 15 is a schematic representation of the generation of a knockout construct using the vector pαGT-S5.5 as the starting vector.
Figure 15B:
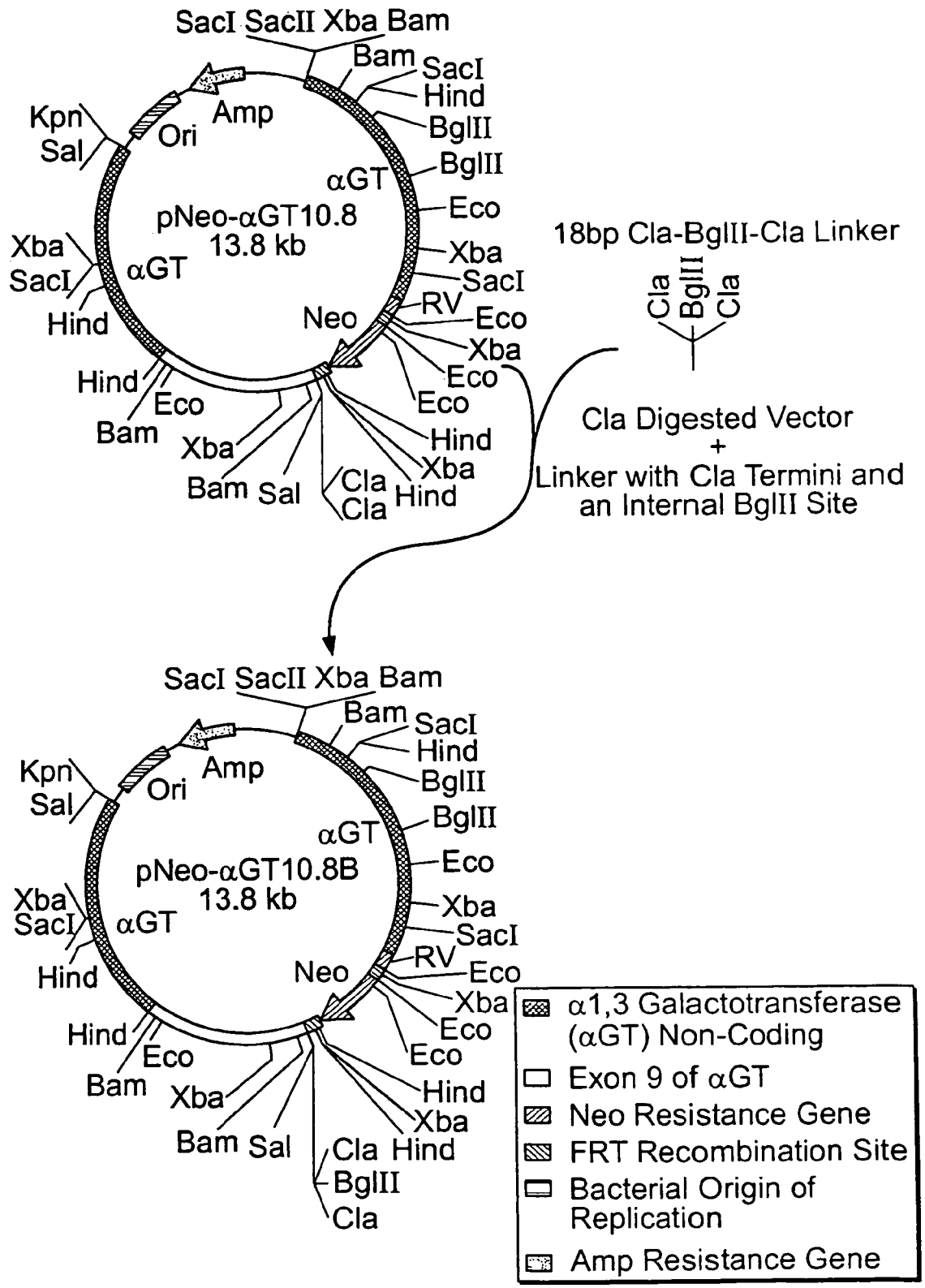
Figure 17:
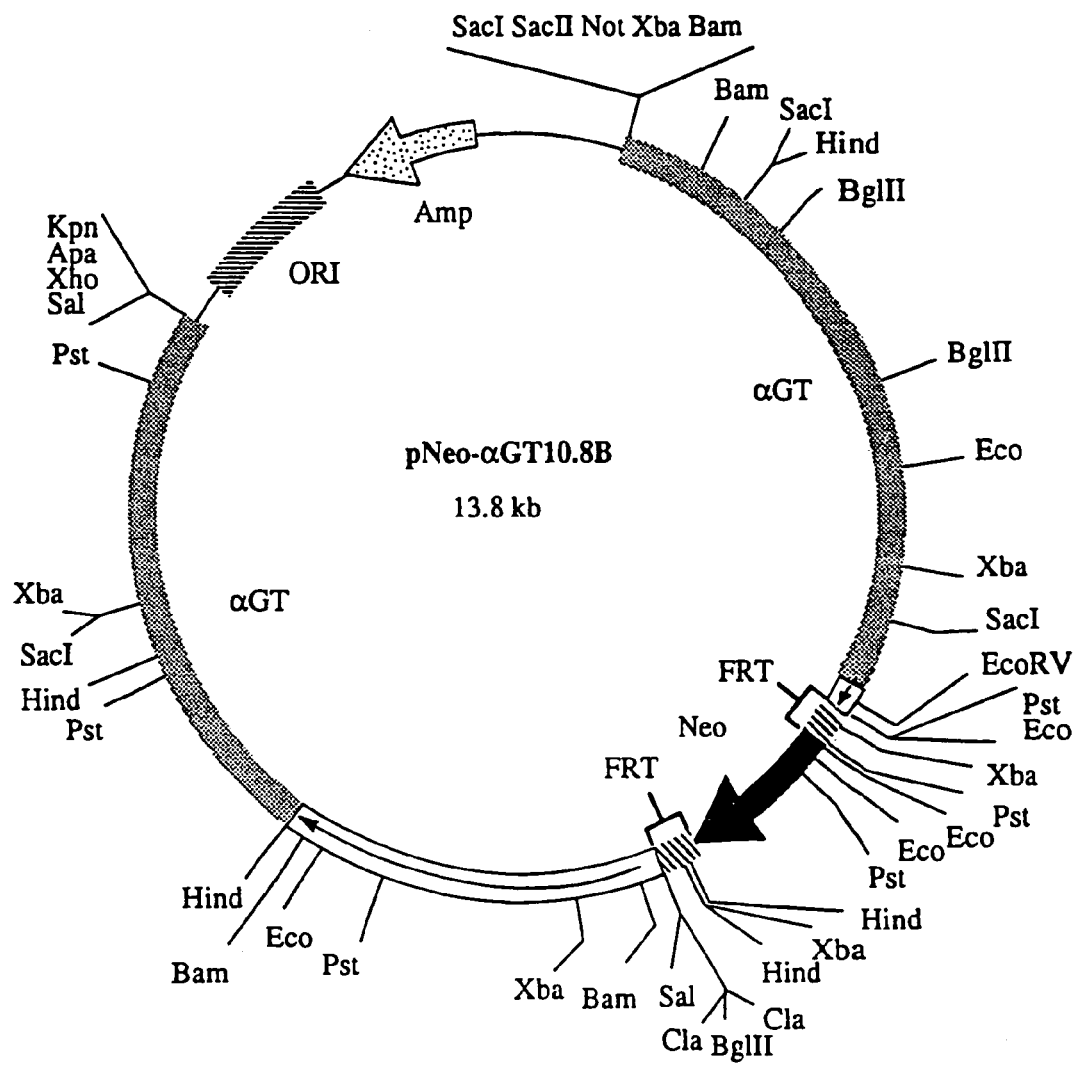
FIG. 17 is a diagram of one example of a final knockout construct that has been sequenced to confirm the identity, copy number and orientation of the various inserts.

To carry out this strategy, the present inventors prepared a series of knockout constructs. The generation of one such construct is outlined in detail in FIG. 15. The vector pαGT-S5.5, which carries the 5.5 kb fragment immediately 3' to the Exon 9 SalI site, was chosen as the starting vector pαGT-S5.5 was digested with EcoRV and ClaI, generating a vector with a blunt end and a ClaI compatible end. A 1.3 kb fragment carrying the PMC1 promoter-driven neo$^R$ gene flanked by FRT sites was excised from plasmid pNeo2FRT (previously constructed by the present inventors) by digesting with BamHI, filling in the restriction site and then digesting with ClaI to generate a fragment with one blunt end and one ClaI compatible end. The nucleotide sequence of this 1.3 kb fragment is provided in FIG. 16 (SEQ ID NO: 13). This fragment was then ligated into the ClaI/EcoRV digested pαGT-S5.5, the ligation mix transformed and colonies screened for recombinants. One colony was recovered that contained the Neo$^R$ fragment inserted into the EcoRV/ClaI of pαGT-S5.5, based on the restriction pattern after digestion with diagnostic restriction enzymes ClaI, EcoRV, XbaI and EcoRI. This construct was designated PNeoαGT6.8.

pNeoαGT6.8 was digested with SmaI, generating a vector with blunt ends. The 4.0 kb Sal1 fragment was excised from pαGT-S4.0 and the ends filled. This fragment was then ligated into the SmaI digested pαGT-S5.5, the ligation mix transformed and colonies screened for recombinants. Four colonies were recovered which contained the 4.0 kb SalI fragment inserted into the SmaI sites of pNeoαGT6.8 with the 5' portion of Exon 9 lying near the 3' portion of the exon in the nearby SalI 5.5 kb fragment. The identity and orientation of the insert was confirmed by the restriction pattern after digestion with diagnostic restriction enzymes XbaI, EcoRI, HindIII, BamHI, EcoRV and others. This construct was designated pNeoαGT10.8.

pNeoαGT10.8 was digested with ClaI, generating a vector with ClaI compatible ends. Two complementary oligomers were synthesized that, when annealed, generated a linker containing translation termination codons in all three reading frames and a BglII site. The linker has ClaI compatible ends. The linker was ligated into the ClaI digested pNeoαGT10.8, the ligation mix transformed and colonies screened for recombinants. Many colonies were recovered that contained the linker inserted into the ClaI sites within pNeoαGT10.8 based on the restriction pattern after digestion with diagnostic restriction enzymes BglII, Cla and BglII/NotI. This construct has been sequenced to confirm the identity, copy number and orientation of the insert. This construct is called pNeoαGT10.8B (FIG. 17).

EXAMPLE 10

ES Cells—General Materials and Methods Working Conditions

Procedures for the isolation and culturing of all cell lines (embryonic stem, primordial germ and fetal fibroblast cell lines) require aseptic conditions to prevent growth of contaminating organisms:

1. All laboratory bench tops and equipment are wiped down with 70% ethanol prior to use.
2. All surgical instruments are autoclaved prior to use.
3. Water for media preparation and cleaning of glassware is of high quality (e.g., Milli-Q water, prepared by passage through a Milli-Q ultrapure water system (Millipore).
4. Glassware is either dry-heat sterilized or autoclaved following extensive cleaning in Milli-Q water before use.
5. All tissue culture work is carried out under laminar flow conditions (Hepa filtered horizontal laminar flow workstation).
6. All media are filter sterilized (22 μm disposable filter) prior to use.
7. Antibiotics are used to minimize the risk of bacterial contamination (Penicillin, Streptomycin and Gentamicin for bacteria; Nystatin for fungi).

| Media/Solution Preparation | |
|---|---|
| DULBECCOS MODIFIED EAGLE MEDIUM (DMEM) | |
| 10.0 g | DMEM powder-Gibco (the low-glucose or high-glucose formulation, with or without pyruvate, may be used; L-glutamine is included) |
| 1.0 liter | Milli-Q-Water |
| 3.7 g | NaHCO$_3$ |
| Stir slowly until dissolved | |
| Adjust pH~7.2 | |
| Filter sterilize (following filter sterilization pH to rises to 7.4) | |
| Keep at 4° C. | |
| STO CELL MEDIUM | |
| 83.0 ml | DMEM |
| 15.0 ml | 15% fetal bovine serum (FBS); batch tested before use |
| 1.0 ml | Pen/Strep 1:100 |
| 1.0 ml | Glutamine 1:100 (if needed) (see note below) |
| Filter sterilize and keep at 4° C. | |
| Note: | |
| Replenish complete medium (DMEM medium) (STO or ES) with glutamine. | |
| *This step is only required if medium is older than 1 week–10 days, as the glutamine breaks down after this time. | |
| ES CELL MEDIUM WITH OR WITHOUT LIF | |
| up to ml 100.0 | DMEM |
| 15.0 ml | 15% FBS (batch tested before use; see below) |
| 1.0 ml (from 0.01M stock) | β-mercaptoethanol (0.1 mM final concentration) |
| 1.0 ml | Pen Strep. 1:100 |
| 0–1.0 ml | Glutamine 1:100 (if needed) |
| 1.0 ml | Nystatin 1:100 |
| 0–2.5 ml | Recombinant murine LIF (from 4 × 10$^4$ U/ml; 1000 U/ml stock); activity-tested using LIF Assay (see below) |
| 0.4 ml | Gentamicin |
| 1.0 ml | Nucleotides |
| 1.0 ml | Non-essential amino acids |
| PENICILLIN/STREPTOMYCIN ANTIBIOTIC SOLUTION (1:100) - | |
| Commonwealth Serum Laboratories, Australia; Catalogue No. 05081901 | |
| Penicillin G | 5000 U/ml |
| Streptomycin Sulphate | 5000 μg/ml. |
| MITOMYCIN-C SOLUTION | |
| 2.0 mg | Mitomycin-C (Sigma Chemical Co. ("Sigma"); Catalogue No. M0503) |
| 200.0 ml | STO Cell Medium |

Filter sterilize, divide into 20 × 10 ml aliquot's and store at −20° C.

Media/Solution Preparation

PHOSPHATE BUFFERED SALINE (PBS)

| For 100 ml Milli-Q Water: | ($Ca^{++}$ and $Mg^{++}$ - containing) | ($Ca^{++}$ and $Mg^{++}$ - free) |
|---|---|---|
| NaCl | 0.89 | 0.80 |
| KCl | 0.02 | 0.02 |
| $KH_2PO_4$ | 0.02 | 0.02 |
| $Na_2HPO_4 12H_2O$ | 0.289 | 1.115 |
| $CaCl_2$—$2H_2O$ | 0.014 | — |
| $MgCl_2$—$6H_2O$ | 0.01 | — |
| Na pyruvate | 0.0036 | — |
| D-glucose | 0.1 g | — |

Adjust to pH 7.4 and filter sterilize
($Ca^{++}$ and $Mg^{++}$ - free PBS is purchased from ICN Cell Biology and Tissue Culture, Cat. No. 18-604-54)

TRYPSIN/VERSENE (TV) WORKING SOLUTION (TV × 1)

In PBS ($Ca^{++}$ and $Mg^{++}$ - free):
0.25% (w/v) trypsin (lyophilized)
0.04% (w/v) EDTA or EGTA
or:

To 1 liter of milli-Q water add the following:

| | |
|---|---|
| Trypsin powder (Porcine, Difco) | 2.5 g |
| EDTA or EGTA | 0.4 g |
| NaCl | 7.0 g |
| $Na_2HPO_4 12H_2O$ | 0.3 g |
| $KH_2PO_4$ | 0.24 g |
| KCl | 0.37 g |
| D-Glucose | 1.0 g |
| Tris | 3.0 g |
| Phenol red | 1.0 ml |

Adjust to pH 7.6, filter sterilize, aliquot and store frozen.
EGTA: Ethylene-glycol-bis(β-amino-ethyl ether) N,N,N',N''-tetra-acetic acid [Ethylene-bis (oxy-ethylenenitrilo)]tetraacetic acid
EDTA: Ethylenediaminetetraacetic Acid Use either EDTA or EGTA. EGTA is preferred as it is less damaging to the ES/PGC cells.

Gelatin Working Solution 0.1% gelatin in Milli-Q Water

Dissolve gelatin by heating to 60° C.

Filter sterilize when still warm.

To gelatinize tissue culture plates:
1. Cover dish with solution, leave 30 minutes
2. Aspirate gelatin and let dish air-dry.

Nucleoside Stock Solution.

| | |
|---|---|
| Milli-Q Water | 100 ml |
| Adenosine (Sigma) | 80 mg |
| Guanosine (Sigma) | 85 mg |
| Cytidine (Sigma) | 73 mg |
| Uridine (Sigma) | 73 mg |
| Thymidine (Sigma) | 24 mg |

1. Dissolve by warming to 37° C.
2. Filter sterilize and aliquot while warm.
3. Store at 4° C. or −20° C.
4. Thawing of nucleotides for use in ES cell media
    (a) nucleotides come out of solution upon thawing;
    (b) Warm to 37° C. to resolubilize before use.

Non-essential Amino Acids (1:100)
    Commonwealth Serum Laboratories; Catalogue No. 09751301
    100× concentrate for minimum essential medium (Eagle):
    (1.0 ml is added to 100 ml ES Cell Medium)
    mg/10 ml milli-Q $H_2O$

| | |
|---|---|
| Glycine | 7.5 |
| L-Alanine | 8.9 |
| L-Asparagine.$H_2O$ | 15.0 |
| L-Aspartic Acid | 13.3 |
| L-Glutamic Acid | 14.7 |
| L-Proline | 11.5 |
| L-Serine | 10.5 |

Whitten's Culture Medium

| | |
|---|---|
| KCl | 0.0356 |
| $KH_2PO_4$ | 0.0162 |
| $MgSO_4.7H_2O$ | 0.0294 |
| NaCl | 0.4 |
| $NaHCO_3$ | 0.2106 |
| Glucose | 0.1 |
| Na Pyruvate | 0.0036 |
| Ca Lactate $5H_2O$ | 0.0527 |
| Na Lactate | 0.2416 ml |
| Milli-Q-$H_2O$ | 100 ml |

The solution is adjusted to a final milliosmolarity of 250–280 by addition of $H_2O$ or NaCl.
Filter sterilize and store at 4° C. for two weeks.

Working Solution:

| | |
|---|---|
| 10 ml | Whitten's medium |
| 1.5 g | BSA fraction V (Miles Pentex, Diagnostic division, Kankakee, Il., USA; Code No. 81-001-4) |

Filter Sterilize and equilibrate in 5%$O_2$:5% $CO_2$:90% $N_2$ at 39.5° C., 95% humidity.

FBS Batch Trials

Batches of FBS vary in the ability to support growth of ES cells, and in the ability to maintain the undifferentiated state of such cells. The following procedure is used to identify suitable batches of FBS. Use ES cells from between 2 & 20 passages:

Day 1.
    Split ES colonies and plate into dishes without feeder cells but with LIF. Incubate for 3 days.

Day 4 Trypsinise to detach colonies and cells. Count cells and dispense into gelatinized 6 cm dishes containing ES Cell Medium and LIF (no serum added) as follows:

| Dish Number | No. Cells | Batch FBS A | Batch FBS B | Control Serum (Batch Tested) |
|---|---|---|---|---|
| | | Non-Inactivated Serum | | |
| 1 | 2 | 250 | 5 ml | — | — |
| 3 | 4 | 250 | — | 5 ml | — |

-continued

| Dish Number | No. Cells | Batch FBS A | Batch FBS B | Control Serum (Batch Tested) |
|---|---|---|---|---|
| 5 | 6 | 250 | — | 5 ml |
| 7 | 8 | 2000 | 5 ml | — | — |
| 9 | 10 | 2000 | — | 5 ml | — |
| 11 | 12 | 2000 | — | — | 5 ml |
| | | Inactivated Serum, as control (56° C. for 15 min.) | | |
| 13 | 14 | 250 | 5 ml | — | — |
| 15 | 16 | 250 | — | 5 ml | — |
| 17 | 18 | 250 | — | — | 5 ml |
| 19 | 20 | 2000 | 5 ml | — | — |
| 21 | 22 | 2000 | — | 5 ml | — |
| 23 | 24 | 2000 | — | — | 5 ml |

There are duplicate plates for each treatment.
Incubate low density dishes for 5 days
Incubate high density dishes for 3 days
Day 7 Fix high density cells and stain with hematoxylin.
Day 9 Fix low density cells and stain for alkaline phosphatase.

LIF Assay

This procedure is used to assay the potency of Leukaemic Inhibitory Factor (LIF).
Day 1 Split one 10 cm dish of confluent STO cells into five dishes. Incubate for 2–3 days in STO medium.
Day 3/4 When cells are confluent, replace medium with DMEM+10% FBS. Incubate for 3 days.
Day 6/7 Collect conditioned medium (CM) and store at 4° C.

*Prepare low density ES cell cultures as described above.

| Dish | No. Cells | C.M. | Medium LIF | 1000 U/ml | Medium w/o LIF | Presumed LIF Content |
|---|---|---|---|---|---|---|
| 1, 2, 3 | 250 | 0.1 ml | 4.9 ml | — | — | 200 U/ml |
| 4, 5, 6 | 250 | 0.25 ml | 4.75 ml | — | — | 500 U/ml |
| 7, 8, 9 | 250 | 0.5 ml | 4.5 ml | — | — | 1000 U/ml |
| 10, 11, 12 | 250 | 1.0 ml | 4.0 ml | — | — | 2000 U/ml |
| 13, 14, 15 | 250 | — | — | 5 ml | — | |
| 16, 17, 18 | 250 | — | — | — | 5 ml | |

There are triplicate plates for each treatment.
Fix and stain for alkaline phosphatase.

Preparation of Fibroblast Feeder Cell Layers

Embryonic pluripotential cells are cultured in vitro on a layer of fetal fibroblast cells. The fibroblast cells provide a wide range of factors necessary for the growth of pluripotential embryonic cells (e.g. growth factors, cytokines, factors that are essential for maintenance of ES cell pluripotency).

Isolation of Porcine Fetal Fibroblasts:
1. Remove developing porcine fetuses (preferably between days 16–30 of development) from uterus by aseptic dissection.
2. Remove skin layer from fetus.
3. Dissect out soft tissue avoiding developing viscera. The white (fibroblast containing) tissue is found just under the skin layer.
4. Wash dissected tissue in PBS ($Ca^{++}$ and $Mg^{++}$ free). Centrifuge at 1000 rpm for 5 min.
5. Remove supernatant.
6. Incubate tissue in Trypsin/Versene Working Solution for 20 min.
7. Dissociate cells by vigorously pipetting. Centrifuge at 1000 rpm for 5 min.
8. Remove supernatant.
9. Resuspend cells in STO Cell Medium. Allow large cell-clumps to settle.
10. Plate out cells within supernatant (i.e., large cell clumps are not included) onto gelatinized tissue culture plates. Incubate cells in an atmosphere of 5% $CO_2$, 95% air (37.5° C., 95% humidity) until a confluent layer of fibroblast cells appears (~4–5 days).
11. Passage of cells may be continued to increase cell numbers, or cells may be frozen or inactivated for further use.

Culture of Fetal Fibroblast Feeder Layers From Frozen Stocks:

Several different types of mouse feeder (STO cells) and porcine and bovine fetal fibroblasts can be used to form feeder layers. These include:
(1) Bradley/Baylor mouse STO feeder cells that have been modified to express human LIF (gift from Allan Bradley, Institute for Molecular Genetics, Baylor College of Medicine, Texas Medical Center, Houston, Tex., USA)
(2) Robertson/Columbia mouse STO feeder cells that have been modified to express murine LIF (gift from Elizabeth Robertson, Columbia University, New York, USA)
(3) Several porcine fetal fibroblast lines
(4) Several bovine fetal fibroblast lines
(the fibroblast lines of (3) and (4) were derived by the present inventors using the procedures described above)
The procedure for producing feeder layers is as follows:
1. Rinse one 10 cm tissue culture (tissue cure) dish with gelatin/Milli-Q water solution for 30 min. Aspirate gelatin solution and let dish air-dry.
3. Add 10 ml of STO cell medium to 15 ml centrifuge tube.
4. Remove feeder layer cells frozen in freezing media from liquid $N_2$ container.
5. Thaw cells by warming vial in hands or in 37° C. water bath.
6. Transfer STO cells to medium in centrifuge tube.
7. Spin at 1000 rpm for 5 min.
8. Resuspend cells in 10 ml medium and transfer to gelatin-treated tissue culture dish.
9. Incubate at 37° C. for 3 days.

Splitting of Feeder Layer STO Cell/Fetal Fibroblasts:

This procedure is used to expand the number of cells from a single confluent plate/dish; cells are detached from the confluent plate and transferred to fresh plates at sub-confluent densities.
1. Gelatinize five 10 cm tissue culture dishes.
2. Examine incubated STO cells under microscope and check for confluence.
3. If STO feeder monolayer is confluent (cells cover bottom of dish, or nearly so), wash gently with PBS ($Ca^{++}$ and $Mg^{++}$-free) for 1 min.
4. Aspirate PBS and add 1 ml Trypsin/Versene Working Solution for 1 min (or until cells start to detach). Check under microscope.
5. Detach cells by vigorously pipetting, add 1.0 ml STO Cell medium (i.e., a ratio of 1:1 STO Cell medium:Trypsin/Versene Working Solution) to neutralize trypsin, and transfer to a centrifuge tube containing 10–15 ml STO Cell medium. Wash cells remaining on dish with some of STO cell medium from the tube. Centrifuge at 1000 rpm for 5 min., aspirate supernatant, resuspend pellet in 1 ml STO Cell medium. Resuspend cells to make single cell suspension. Make up to 50 ml with STO Cell medium.
6. Dispense 10 ml into each of the five tissue culture dishes and incubate until confluent (~3 days).

Inactivation of Feeder Layers:

The present inventors use two alternative methods for inactivating feeder layers, which stops the cells from dividing:

(1) Mitomycin Treatment:
1. Check dishes for confluence of STO cells/fetal fibroblasts.
2. Thaw mitomycin-C solution and use undiluted.
3. Aspirate STO cell medium from feeder cell plate.
4. Add 10 ml aliquot of mitomycin-C to plate and incubate at 37° C. for 1–3 hours.
5. Aspirate mitomycin-C, wash cells in 1×PBS (without $Ca^{++}$ or $Mg^{++}$) for 1 min.
6. Aspirate PBS and add 1 ml trypsin solution for 1 min.
7. Detach cells by vigorously pipetting and transfer to STO cell medium in centrifuge tube.
8. Centrifuge at 1000 rpm for 5 min.
9. Resuspend cell pellet in 1 ml ES Cell Medium.
10. Plate out in dishes in preparation for addition of ES cells.

(2) Gamma Irradiation:
1. Check dishes for confluence of STO cells/fetal fibroblast.
2. Trypsinise cells into single cell suspension.
3. Irradiate cells (3000 rads) in STO cell medium.
4. Centrifuge at 100 rpm for 5 min.
5. Resuspend pellet in 1 ml ES Cell Medium.
6. Transfer cells to gelatinized tissue culture dishes with ES Cell Medium and place in incubator at 37° C. until the cells adhere to the dish. NOTE: If cells are not confluent, count using hemocytometer and seed at $5 \times 10^4$ cells in 1 ml medium per well of Nunc 4-well plate. One 10 cm dish of inactivated cells can be split into:

Ten 4-well plates (Nunc tissue culture plates), or Eight 3.5 cm tissue culture dishes, or Three 6 cm tissue culture dishes, or Two 20 cm tissue culture dishes.

Demonstration of Totipotency

A. Blastocyst Injection

The ability of embryonic cell lines to form germline chimeric animals is a conclusive test for their totipotency. This can be accomplished by blastocyst injection experiments, using techniques for various mammalian species substantially the same as those established for the mouse. See Example 14, below. See also, e.g., Bradley, Production and Analysis of Chimeric Mice, In: *Teratocarcinomas and Embryonic Stem Cells: A Practical Approach* (E. J. Robertson, ed.), IRL Press, Oxford, pp. 113–52 (1987). However, for porcine manipulations the holding pipette must be somewhat larger as porcine embryos are larger than mouse embryos.

B. Co-Culture of ES Cells/PGC's and Morula Embryos

Embryos at the morula stage of development are surgically collected from superovulated animals. For porcine embryos, for example, the zona pellucida is then disrupted using Acid Tyrodes solution and ES cells/PGC's are cultured in the presence of the zona pellucida-disrupted morulae. ES/PGC cells adhere to the exposed morula cells and, following overnight culture in Whitten's medium, the embryos are transferred to synchronized recipients. Preferably, the zona pellucida-disrupted morula is completely free of the zona pellucida. However, this need not be the case as long as the ES cells/PGC's can gain direct access to at least some of the morula cells.

C. Morula Injection

ES cells and PGC's can be injected into a morula embryo prior to formation of the blastocyst cavity. The technique is similar to blastocyst injection. ES cells or PGC's are drawn into an injection pipette, which is inserted beneath the zona pellucida. Then, the cells are expelled so that they are in contact with the cells of the morula embryo. The injected morula is then cultured overnight in Whitten's medium (porcine) or other appropriate medium to allow blastocyst formation.

D. Nuclear Transfer and Embryo Cloning

ES cells and PGC's can be fused to enucleated zygotes that have been derived by in vitro maturation, in vitro culture, in vitro fertilization or collected surgically. Following successful fusion the embryos can be transferred to synchronized recipients. In vitro or in vivo-collected porcine oocytes, for example, are manipulated in Whitten's medium supplemented with 1.5% BSA Fraction V and 7 µg/ml cytochalasin B (Sigma). A bevelled micropipette is used to remove the metaphase plate from the oocyte. A single ES cell or PGC (after trypsin treatment to form a single-cell suspension) is inserted through the zona using a bevelled micropipette, such that the cell comes in contact with the oocyte plasma membrane. Fusion is achieved in a 28 V/cm AC field for 5 sec. followed by an 80 V/cm DC pulse of 100 µsec. duration. Subsequent to observed fusion, embryos are incubated at 39° C. in 5% $CO_2$, 5% $O_2$, 90% $N_2$ in microdrops of Whitten's medium supplemented with 1.5%-BSA, until transfer to a synchronized recipient.

EXAMPLE 11

Murine ES Cell Culture

ES cells are able to differentiate spontaneously into many different cell types, and culture conditions which prevent this differentiation are critical for the continuous passage of these cells in an undifferentiated form, capable of contribution to chimeric mice.

I. Culture Conditions

ES cells are grown in polystyrene cell culture dishes treated with 0.1% gelatin (made up in PBS or Milli-Q water) for 10 minutes. A feeder layer of mitotically inactivated fibroblasts provides a source of cytokines. The fibroblasts are either primary mouse embryo fibroblasts (PMEFs), or STO fibroblasts, an immortal line. The medium used is DMEM supplemented with glucose, amino acids and nucleosides. Robertson, Embryo-Derived Stem Cell Lines. In: Teratocarcinomas and Embryonic Stem Cells: A Practical Approach (E. J. Robertson, ed.), IRL Press, Oxford (1987). To this medium is added LIF (final concentration of $10^3$ U/ml Esgro, AMRAD). FBS is added to 15%. The batch of FBS is chosen on the basis of its ability to support ES cell growth with low levels of differentiation (i.e, only rare individual cells undergo differentiation. The ES cells are grown in an atmosphere of 5–10% $CO_2$, at 37° C.

II. Routine Passage

ES cells must be passaged frequently to prevent the colonies from growing too large and differentiating. This is achieved by splitting the cells at a ratio of 1:10 to 1:40, every two to four days.

EXAMPLE 12

Genetic Manipulation of Cells

The general procedures set out in this Example provide guidelines that are readily adaptable to individual experimental situations that might employ, for example, different cell lines or equipment supplied by different manufacturers. This Example also provides specific procedures used and results obtained in generating a set of mouse ES cell lines in which the α 1-3-galactosyltransferase gene was disrupted by homologous recombination. The general procedures provided in this Example are adapted for mouse ES cells. However, the procedures are substantially similar for porcine-ES cells.

I. Introduction of DNA into ES Cells by Electroporation
  A. Coat required number of plates with 0.1% gelatin (in PBS or Milli-Q water). (Usually 2×6 well plates and 8 well plate)
  B. Thaw $10^7$ embryonic fibroblasts into DMEES (equivalent to ES Cell Medium); inactivate by irradiating at 3000 Rad.
  C. Count irradiated cells, spin down and resuspend in DMEES to $10^6$ cells/ml.
  D. Aspirate gelatin from plates and plate cells at: $7×10^5$ cells/well (6 well plate) in 2.5 ml medium; $7×10^4$ cells/well (24 well plate) in 1 ml medium. Incubate at 37° C., 5–10% $CO_2$ for 3–4 hr.
  E. Wash ES cells in 5 ml (250 ml flask) PBS-EGTA- and let sit at room temperature for 4 min.
  F. Remove PBS, add 5 ml trypsin (CSL) and leave at room temperature for 2–4 min. Wash down cells, add 10 ml DMEES and count. Approximately $5×10^6$ to $2×10^7$ ES cells are needed for experiments.
  G. Centrifuge cells and resuspend in 10 ml PBS. Centrifuge again and resuspend in 540 µl PBS. Dilute 50 µl into 10 ml DMEES and culture to determine plating efficiency.
  H. Add 5–10 µg DNA to cells in 10 ul PBS (total volume, 500 ml) and transfer to sterile electroporation cuvette (e.g. Biorad).
  I. Electroporate at 0.22 kV, 500 µFD (time constant should be ~8.4). This is achieved using a Biorad Gene Pulser unit (Biorad Catalogue No. 1652078) with capacitance extender (Biorad Catalogue No. 1652087), or similar device.
  J. Resuspend in 10 ml DMEES with constant pipetting to break up clumps of DNA from lysed cells.
  K. Centrifuge cells and resuspend in 5 ml DMEES.
  L. Take 50 µl, add 50 µl trypan blue solution and count for viability.
  M. Culture by dilution plating to determine plating efficiency.

II. Selection Conditions
  ES cells that do not express a neomycin resistance gene are selectively killed by treatment with G418 at 200–500 µg per ml of medium. Antibiotic-containing medium is changed daily. A population of cells that has not been electroporated also is treated in order to see how genuinely sensitive cells respond to the G418 treatment. After 6 to 10 days, cells resistant to the antibiotic will be evident as healthy colonies. These cells will have been transformed by the targeting construct and can be screened for homologous recombination (i.e., screened for gene targeting versus random integration).
  Resistant colonies are picked from the selection dish with a mouth pipette and dispersed into a single cell suspension. Half of these cells are frozen away while the other half is expanded and used to determine whether or not homologous recombination has occurred. If the colonies are small, it is sometimes preferable to expand the whole colony in a 24 well dish, and then to freeze half while further expanding the other half for genetic analysis.

III. Picking ES Cell Colonies for Genetic Analysis After Selection
  A. Method 1: Freezing Half Colonies
    1. The day before colony picking:
      a) Coat required number of plates with 0.1% gelatin (in PBS). Two plates per 24 colonies to be picked: one plate is for freezing and one plate is for clone expansion. Start with 20×24 well plates.
      b) Count irradiated fibroblasts, spin down and resuspend in DMEES.
      c) Aspirate gelatin from 10 plates and plate ~$10^5$ (can use as few as $5×10^4$) cells/well in 1 ml DMEES. Incubate at 37° C., 10% $CO_2$ overnight (or a minimum of 1 h).
      d) Aspirate the gelatin from the other 10 plates.
    2. On the day of colony picking:
      a) Change medium on ES cells before and regularly during picking (to remove floating cells).
      b) Pull plugged pasteur pipettes. Use a fresh pipette after each 24 colonies. The desired tip is about half a colony in diameter, with the constriction over 1–2 cm. The tip should be perpendicular and neat. Note: after drawing the pipette, rub the glass at the desired break point with freshly drawn glass, then bend.)
      C) Label multi-tip reservoirs for:
        1 PBS-EGTA
        2 Trypsin-Versene
        3 DMEES
        4 2× Freezing mix(20% DMSO in FCS)
      d) Using multipipettor, dispense 50 µl PBS-EGTA into 24 wells of 96 well plate.
      e) At microscope: Connect finely drawn pasteur pipette to mouth pipette tube. Dislodge colony from plate and transfer (in minimum volume) to one well of a 96 well plate. Expel contents of pipette; the bubbles serve as a location guide. Pick 24 colonies or as many as possible in <10–15 min (preferably a multiple of 6).
      f) Back in hood: Add 100 µl trypsin to each well using multipipettor) and leave at RT for 2 min.
      g) Pipette up and down 10–15× to disperse cells, then add 100 µl DMEES. (This should be done within 4–6 min after trypsin addition).
      i) Divide cell suspension between freezing and expansion plates using 12 channel pipette with every second tip fitted. Transfer 125 µl to gelatinized 24 well plate (to freeze); the remaining ~125 µl is transferred to a 24 well plate with feeder layer (for DNA). The plates are labelled and carefully aligned to ensure that one clone goes into the same well of each tray.
      j) Add 125 µl 2× freeze mix to each well on freezing plate, mix well by swirling.
      k) Seal in ziplock bag or plastic wrap and place in −70° C. freezer in an equilibrated styrofoam box. Interleave the plates with styrofoam sheet.
      l) Incubate expansion plates until there are sufficient cells for genotype analysis.

A. Method 2: Freezing After Expansion to 24 Wells.
    1. The day before colony picking:
      a) Coat required number of plates with 0.1% gelatin (in PBS). Start with 10×24 well plates.
      b) Count irradiated fibroblasts, spin down and resuspend in DMEES.

c) Aspirate gelatin from the plates and plate ~10⁵ cells/well in 1 ml DMEES. Incubate at 37° C., 10% $CO_2$ overnight (or a minimum of 1 h).
2. On the day of colony picking:
   a) Pick colonies as described for half colonies (method 1, above) but instead of dividing the cell suspension between freezing and expansion plates, the entire cell suspension goes into the expansion plate.
   b) After 3–4 days (with daily medium changes) the cells will have grown sufficiently to be frozen. Working one plate at a time (with practice two can be handled), aspirate medium from each well. Flood with PBS/EGTA for 4 minutes. Meanwhile, set up pipette tips to fit alternate channels of a twelve channel multipipettor. Aspirate PBS.
   c) Add 100 μl trypsin (using multipipettor and alternate channels) and leave at room temp. for 2 min.
   d) Pipette up and down 10–15× to disperse cells of first row, change tips, then add 100 μl DMEES. Repeat for each row. (This should be done within 6 min of trypsin addition).
   e) Using 12 channel pipette with every second tip fitted, transfer 125 μl to gelatinized 24 well plate (to freeze). The remaining cells will be expanded for DNA. It is crucial that the plates are labelled and carefully aligned to ensure that the freezing tray matches the expansion tray.
   f) Add 125 μl 2× freeze mix to each well on freezing plate; mix well by swirling.
   g) Seal in ziplock bag or plastic wrap and place in −70° C. freezer in an equilibrated styrofoam box. Interleave plates with styrofoam sheets.
   h) Add 1 ml of DMEES to the expansion tray. (There will be sufficient feeder cells to give good plating efficiency). Incubate for 3–4 days until there are sufficient cells for genotype analysis.

IV. Thawing of ES Cell Clones Frozen in 24-well Plates

Cells that have been identified to have the desired genetic alteration are recovered from a duplicate plate frozen at −70° C. The plate is taken to the laminar flow hood and removed from the plastic bag. Each well is filled with warm medium, and feeder cells are Added to the well(s) of interest. The plate is placed in a 37° C. incubator for 60 min., then the medium is replaced colonies will appear after two or three days. These colonies are expanded for establishment of new frozen stocks, and tested for 1) karyotype analysis; 2) confirmation of the desired genetic alteration; 3) mycoplasma infection; and 4) ability to form chimeras.

EXAMPLE 13

Production Of Mouse ES Cell Knockouts Using the pNEOαGT10.8B Construct

I. Transformation

A total of 1×10⁷ E14 ES cells was electroporated with 5 μl of 1 μg/μl pNeoαGT10.8B DNA (linearized by XhoI digestion) (see Example 9 and FIG. 17). Electroporation was carried out in 600 μl in a wide cuvette at 25 μF, 350V for 0.5 msec. Cells were recovered in 6 ml. ES complete medium and plated into 6×100 mm petri dishes, each containing a feeder layer of Neo$^R$ STO cells.

Cells were cultured in ES complete medium for 3 days and then medium containing 200–350 g/ml G418 was substituted. This medium was changed every second day. After 9 days, individual Neo$^R$ colonies were sufficiently large to be identified and recovered. Colonies were picked in 201 PBS and 201 of trypsin solution were added. Forty μl of 60% BRL conditioned medium in ES complete medium were then added. Aliquots of 40 μl were transferred to single wells of each of two 24-well plates. One plate contained a feeder layer of STO cells in 100 μl ES complete medium. 140 μl of 2×DMSO freezing mix was added to this plate, which was stored at −80° C. Each of the wells of the second 24-well plate contained 1 ml of 60% BRL conditioned medium in ES complete medium. This plate was incubated at 37° C. until the colonies were confluent.

II. Confirmation of Homologous Recombination

Medium was aspirated off confluent colonies and 400 μl lysis buffer (10 mM Tris pH 7.8, 100 mM NaCl, 1 mM EDTA, 1% SDS, and 500 g/ml Proteinase K) added. The cells were lysed at 37° C. overnight, extracted with 400 μl 1:1 phenol/chloroform and transferred to Eppendorf tubes containing 1 ml 95% ethanol and 0.2M NaAc. DNA was pelleted by centrifuging at 13,000 rpm in an Eppendorf centrifuge, the pellet washed twice with 80% ethanol and redissolved in 30 μl water.

Southern analysis (see, e.g., Sambrook et al., supra) was used to identify ES cell clones where homologous recombination had occurred at the 3' end of the construct. Aliquots of 15 μl of DNA were digested with 20 units of the restriction enzyme BglII according to the manufacturer's recommendations. After incubation at 37° C. overnight, the DNA was electrophoresed through a 0.8% agarose gel (in a Tris acetate, EDTA buffer) at 1–2V/cm overnight, using 750 ng of HindIII-digested lambda DNA as markers. The DNA was transferred to a Zetaprobe nylon membrane using a Hybaid vacublotter at a vacuum of 80 cm Hg for 1 hour.

The membrane was prehybridised in a Hybaid hybridization bottle in 10 ml of the following hybridization mix for 3 hours at 65° C.:

0.25 M $Na_2HPO_4$ pH 7.2
7% SDS
1 mM EDTA
100 μg/ml salmon sperm DNA
10% PEG

Radioactively labeled probe DNA was prepared using a BRESATEC gigaprime oligo labeling kit (Cat. No. GPK-1) according to the manufacturer's recommendations. Approximately 50 ng of a 0.7 kb EcoRI/XmnI DNA fragment from beyond the 3' terminus of the construct pNeoαGT10.8B (see Example 9 and FIG. 17) were labeled with ³²P-dATP to a specific activity of 5×10⁸ cpm/μg. The denatured probe was added to the prehybridising membrane in the Hybaid bottle and incubated overnight at 65° C.

The membrane was removed from the Hybaid bottle, rinsed with 0.5×SSC, 0.1% SDS prewarmed to 65° C., and then washed 2–3 times with 0.1×SSC, 6.1% SDS at 65° C. for 30 min each wash. Excess moisture was then blotted from the membrane, the membrane wrapped in plastic wrap and exposed to a phospho-imager screen for 16 hours up to 3 days. The image was visualized on an Imagequant phospho-imager.

Figure 18:
FIG. 18 is a Southern blot of genomic DNA from various murine ES cell lines transformed with the knockout construct of FIG. 16, probed to reveal the diagnostic fragments depicted in FIG. 14.

Results are shown in FIG. 18, which is a Southern blot of DNA from 15 ES cell lines probed with the diagnostic 0.7 kb EcoRI/XmnI DNA fragment described above and in Example 9. The 6.4 kb band, diagnostic for a homologous recombination event in the α 1-3 galactosyltransferase gene (α 1-3 Gal T) (see Example 9), is seen in 6 of the 15 ES cell lines examined. All of the 6 knockout cell lines appeared to be heterozygous for the inactivated allele since the 8.3 kb band, diagnostic for the uninterrupted α-1,3-Gal T gene (see Example 9), was also present in all six lanes.

Two cell lines, designated hereinafter "8D1" and "7C2," were chosen for further analysis. Cell lines 8D1 and 7C2 were identified by Southern analysis to contain an α-1,3-Gal T allele where homologous recombination had occurred at the 3' boundary of the construct.

Figure 19:
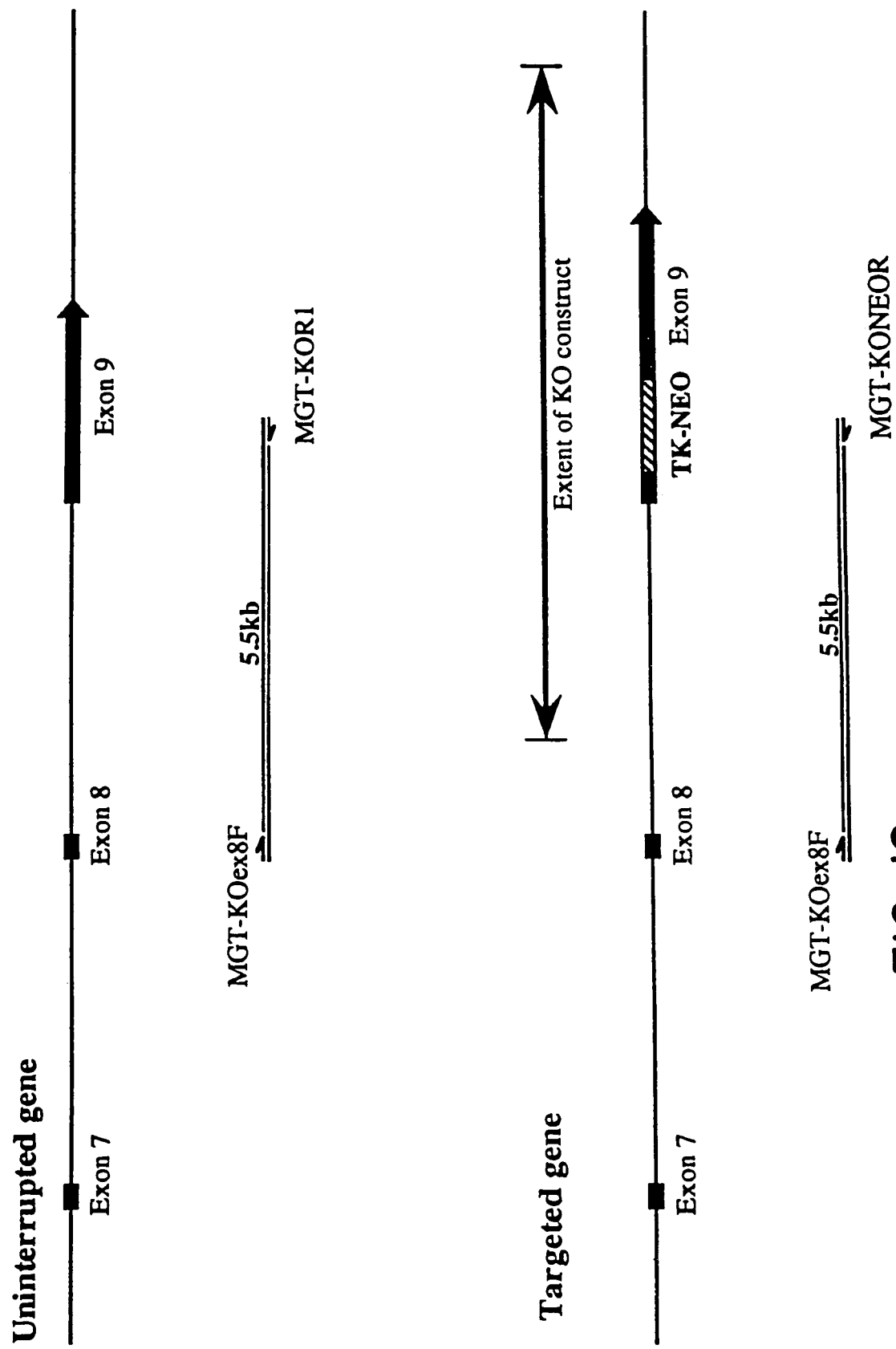
FIG. 19 depicts the "long" PCR products derived from wild type and interrupted α-1,3-GalT genes using the designated primers.

Long range PCR was then used to determine whether or not homologous recombination had occurred at the 5' boundary of the construct within these cell lines. Two sets of primers were used in separate PCR experiments:

1) Wild-type Primers:
MGT-KOex8F and MGT-KOR1 span the intron between exons 8 & 9, and amplify a 5.5 kb fragment from the wild-type α-1,3-GalT gene (FIG. 19)

Sequences:
MGT-KOex8F

5'TGCTGGAAAAGTACTACGCCACACAGAAACTCA-3' (SEQ ID NO: 14)
(Nucleotides 1014–1046 in FIG. 4)
MGT-KOR1

5'AGCCAGAGTAATAGTGTCAAGTTTCCATCACAA-3' (SEQ ID NO: 15)
(Nucleotides 1779–1811 in FIG. 4)

2) Knockout Primers:
MGT-KOex8F and MGT-KONeoR span exon 8 to the $Neo^R$ gene cassette in the "knock-out" allele and amplify a 5.5 kb fragment from the knocked out allele (FIG. 19)

Sequence:
MGT-KONeoR

5'-GCCACACGCGTCACCTTAATATGCCAAGTGGAC-3' (SEQ ID NO: 16)
(Nucleotides 323–355; FIG. 16)

Each reaction contained ~100 ng genomic DNA as template in a reaction volume of 50 μl and contained 25mM Tris HCl (pH9.1), 16 mM $(NH_4)_2SO_4$, 250 μM dNTPs, 3.5 mM $MgCl_2$, 100 ng each primer, 2 units Taq polymerase and 0.025 units Pfu polymerase. The reactions were heated at 94° C. for 1 min, then 45 cycles of 94° C. for 15 sec, 68° C. for 6 min, followed by a single step of 72° C. for 10 min. Genomic DNAs from putative "knock-out" ES cell lines from CBA/C mice (homozygous for the wild-type α-1,3-Gal T allele) were amplified in separate reactions using each set of primers. A 101 aliquot of each PCR was analyzed by Southern blotting (Sambrook et al., 1989).

Figure 20:
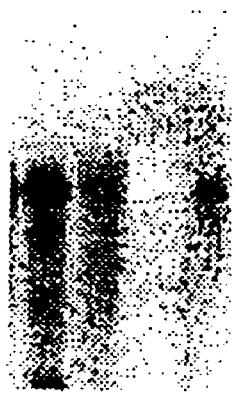
FIG. 20 is a Southern blot of long PCR products obtained from wild type and knockout mice.

The results are illustrated in FIG. 20:

Knockout Primers:
A 5.5 kb fragment that hybridized to the 1.3 kb $Neo^R$ gene cassette (FIG. 16) was generated from 7C2 DNA (FIG. 20; lane 4) and 8D1 DNA (not shown). This band was not generated from CBA/cDNA (FIG. 20; lane 3).

Wild-type Primers:
A 5.5 kb fragment that hybridized to the α-1,3-Gal T gene probe (isolated by Sal I digestion of pαGT-S4.0) was generated from 7C2 and CBA/cDNA's (FIG. 20; lanes 1 and 2 respectively) and 8D1 DNA (not shown). This product did not hybridize to the $Neo^R$ gene probe.

These results demonstrate that homologous recombination had occurred at the 5' boundary of the construct in cell lines 8D1 & 7C2.

EXAMPLE 14

Generation of Animals Carrying an ES Cell Genome

The procedures provided in this Example are adapted for mouse ES cells. However, the general strategy is substantially the same for porcine ES cells and PGC's.

I. Preparation of ES Cells for Injection
ES cells are split into wells of a 24-well dish at cell densities of 1:2, 1:4, 1:8 and 1:16, relative to the initial density, two and three days before injection. The most vigorous and least differentiated cultures are chosen on the basis of morphology.

II. Embryo Injection and Production of Chimeric Mice
Mouse embryos are collected from either superovulated or naturally mated female mice, approximately 3.5 days after mating. After overnight culture in M16 medium (Bradley, Production and Analysis of Chimaeras. In *Teratocarcinomas and Embryonic Stem Cells a Practical Approach* (E. J. Robertson, ed.) IRL Press, Oxford, pp. 113–52 (1987)), those that have cavitated to form blastocysts are microinjected with about 12 to 20 ES cells. This microsurgical procedure is performed with instruments drawn from capillary glass, and injection is controlled with micrometer syringe-based hydraulic devices. A differential interference contrast-equipped inverted microscope is used to view the procedure.

After injection, blastocysts are transferred to the uterus of pseudopregnant female mice. Chimeric mice are identified by coat color contribution by the ES cells. Chimeric mice show agouti coat colour derived from the host blastocyst, and chinchilla contributed by the ES cells.

Chimeric mice were generated from ES cells carrying the interrupted α-1,3-Gal T allele (including 8D1, 7C2 cells) by injection into C57Bl/6J x CBA F2 blastocysts. The ability of individual chimaeric mice to transmit the ES cell characteristics through the germ-line was estimated by glucose phosphate isomerase (Gpi) analysis of sperm (Bradley, supra, (i987)); Mann et al., J. Reprod & Fert. 99, 505–512 (1993). Glucose phosphate isomerase catalyses the interconversion of glucose-6-phosphate to fructose-6-phosphate. Mice have a single structural Gpi locus with two main alleles Gpi 1A and Gpi 1B. Gpi 1A codes for protein which appears as a slow cathodically migrating band during electrophoresis and occurs in strains such as BALB/c and C129. (The ES cells used here were derived from strain 129 mice). Gpi 1B determines an enzyme that moves faster than Gpi 1A and occurs in the wild and in strains such as C57 and CBA (used here to derive host blastocysts).

Heterozygotes have the two parental bands plus an intermediate band which indicates the dimeric structure of the enzyme. Multiple electrophoretic forms occasionally observed are due to oxidation of sulfyhdryl groups and not due to tissue-specific expression. In chimaeric mice, the ratio of Gpi 1A (strain 129-derived) to Gpi 1B (derived from the host blastocyst) indicates the proportion of cells with the ES cell genotype within different tissues. The appearance of Gpi 1A (derived from the ES cells) in the sperm suggests that the mouse is able to transmit the ES cell genotype through the germ-line.

III. Generation of Mice Homozygous for the Genetic Change Introduced into the ES Cells.
Chimeric mice with sperm derived from ES cells were mated to BALB/c mice. Offspring with the 129/Ola X BALB/c genotype (i.e. heterozygous for the ES cell genotype) are grey. Half of these grey mice were expected to carry the interrupted allele. Mice heterozygous for the interrupted allele were identified by PCR analysis of genomic DNA obtained from blood.

To generate mice homozygous for the inactivated α-1,3-Gal T gene, the heterozygous mice were mated to each other. One quarter of the offspring were expected to be homozygous for the interrupted gene. Homozygotes were identified by PCR analysis of genomic DNA obtained from blood. The PCR strategy was based on the insertion of a Neo$^R$ gene in the Sal I site of exon 9 of the α-1,3-Gal T gene (FIG. 13).

Wild-type Primers:

E9F: 5'TCAGCATGATGCGCATGAAGAC 3' (SEQ ID NO: 17)

(homologous to sequence about 40 to 60 bp 5' to the Sal I site of exon 9, corresponding to nucleotides 1257–1278; FIG. 4)

E9R2: 5'TGGCCGCGTGGTAGTAAAAA 3' (SEQ ID NO: 18)

(homologous to a region about 175 to 195 bp 3' to the Sal I site of exon 9, corresponding to nucleotides 1511–1492; FIG. 4)

Figure 21:
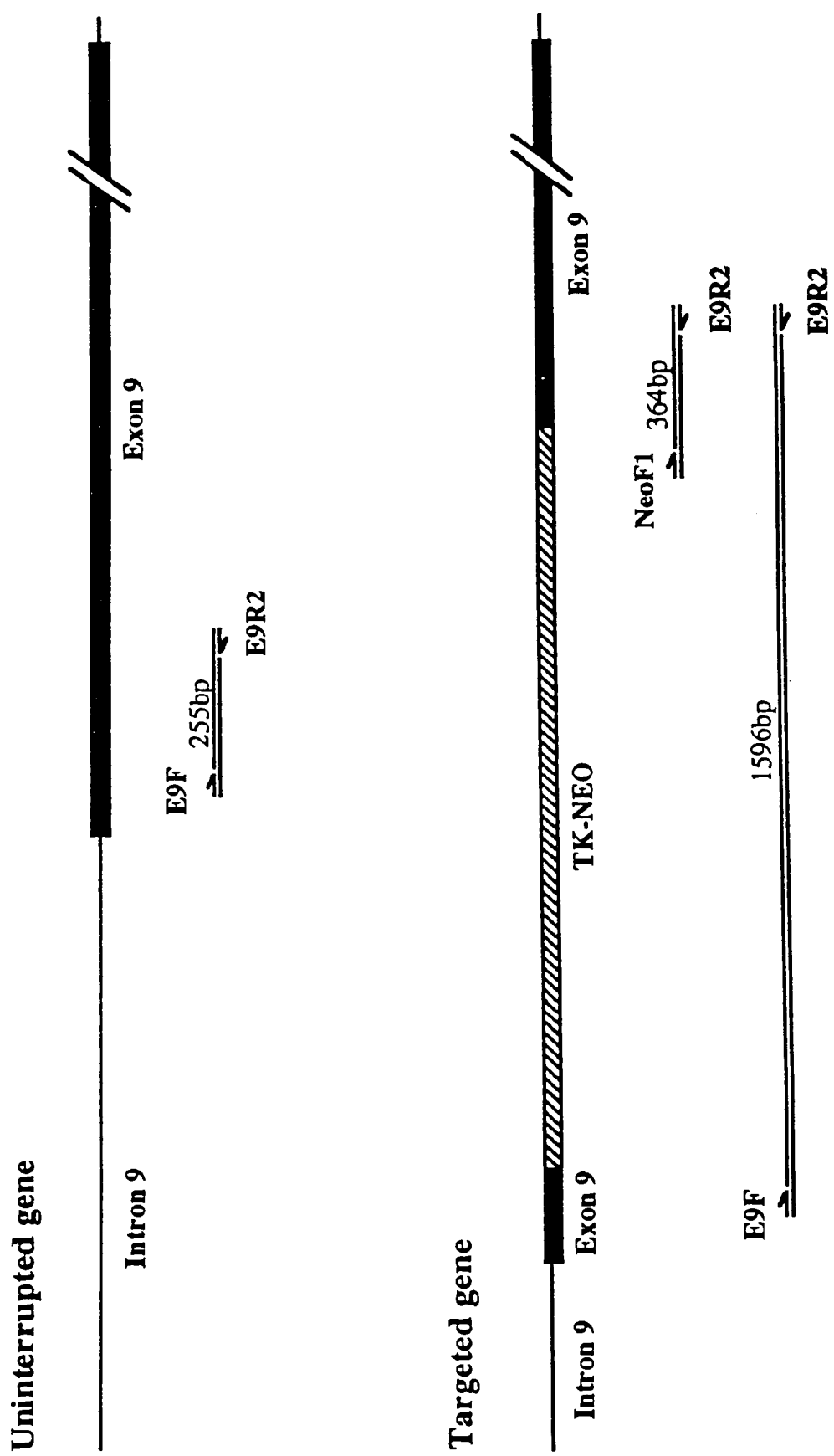
FIG. 21 depicts the PCR products used for identification of the interrupted (targeted) galT locus.

The expected fragment size generated from the wild-type allele is 255 bp (FIG. 21). These primers also can potentially generate a 1596 bp PCR fragment from the interrupted allele. In practice this fragment was not generated when both the wild-type and interrupted alleles were present, probably because the smaller 255 bp product is amplified preferentially.

Knock-out Primers:

NeoF1: 5' TCTTGACGAGTTCTTCTGAG 3' (SEQ ID NO: 19)

(corresponding to nucleotides 1170–1189; FIG. 16)

E9R2: (the same primer described above to detect the wild-type allele)

The expected fragment size is 364 bp (FIG. 21).

Mice were grown to weaning age and bled from the tail. Sodium Heparin was added to about 10 U/ml. PCR amplification was conducted on 1 μl of heparinised blood (~10$^4$ nucleated cells) in a 50 μl reaction volume containing 100 mM Tris-Acetate pH 8.8, 3.5 mM MgCl$_2$, 0.2 mM dNTPs, and 2 units Tth DNA polymerase. Each reaction contained both the wild-type and knock-out primers at a concentration of 2 ng/μl for each primer. To ensure that Tth polymerase was not inhibited by heparinized blood, each reaction was performed in duplicate.

One of the reactions was spiked with two DNA samples:
i) 10 fg (~600 molecules) of linearized KO plasmid pNeoαGT10.8B.
ii) 1 fg (~1000 molecules) of a 983 bp RT-PCR product that includes Exon 9.

The other reaction was not spiked. Thus, two separate PCR reactions were set up for each blood sample. In addition, control PCR reactions with no genomic DNA template and with or without spikes were conducted. Each reaction mix was heated at 94° C. for 3 min., then incubated for 40 cycles at 94° C. for 40 sec., 53° C. for 40 sec., and 72° C. for 40 sec. Aliquots of 5 μl of each reaction mix were electrophoresed on a 3% agarose gel, and DNA fragments were visualized on a UV light box after staining with ethidium bromide. HpaII-digested pUC19 plasmid DNA was used for markers.

Figure 22:
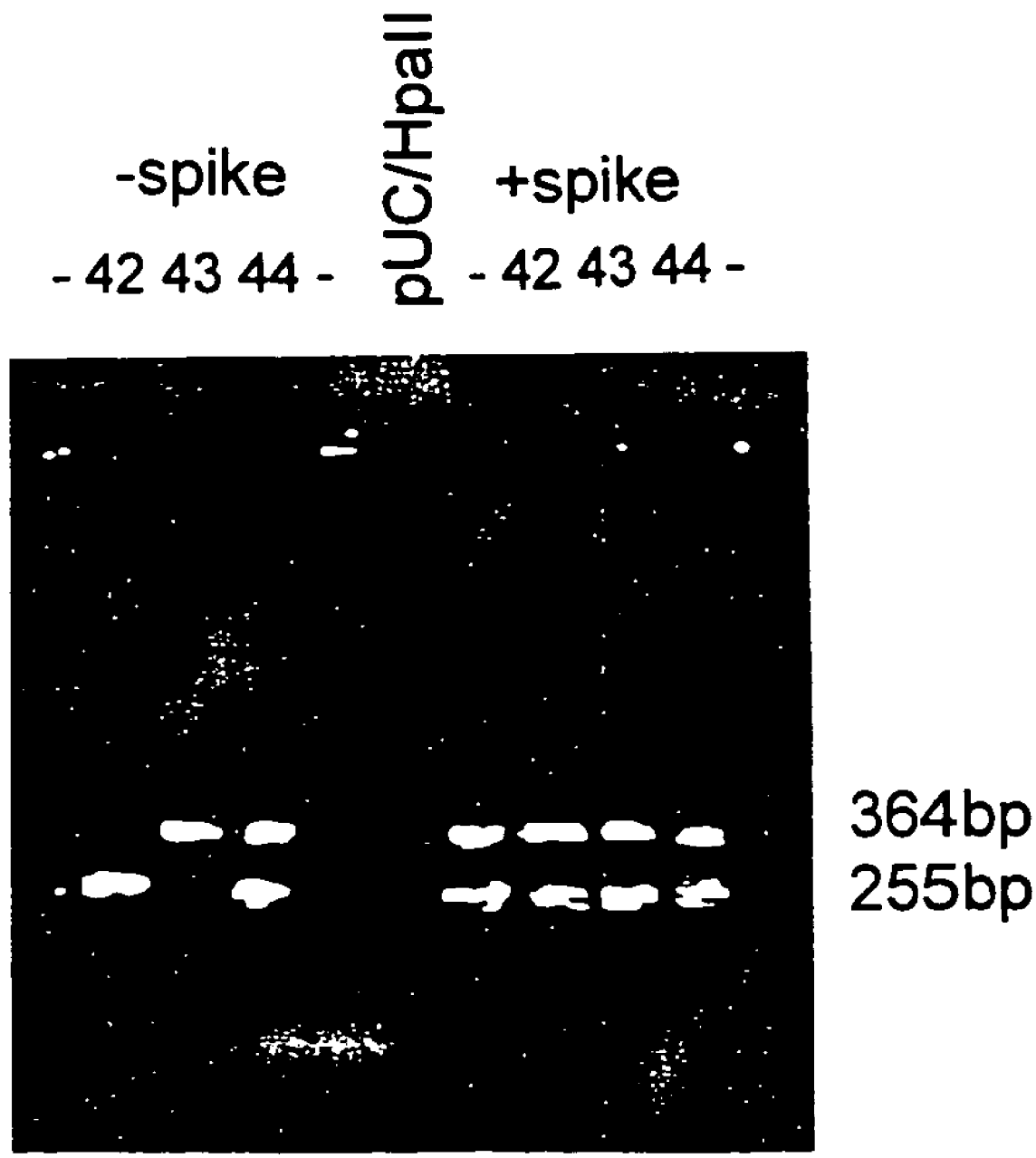
FIG. 22 shows PCR products generated from mice carrying interrupted (inactivated) GalT alleles.

Results of the PCR analysis for three mice, and a "no DNA" control, are shown in FIG. 22. For mouse #42, the KO primers generated a 364 bp band in the + spike reaction only. The wild-type primers generated a 255 bp band in the + spike and − spike reactions. These results demonstrate that mouse #42 is homozygous for the wild-type allele. For mouse #43, the wild-type primers generated a 255 bp band in the + spike reaction only. The KO primers generated a 364 bp band in the + spike and − spike reactions. These results demonstrate that mouse #43 is homozygous for the interrupted allele. For mouse #44, the KO primers generated a 364 bp band in the + spike and − spike reactions. The wild-type primers generated a 255 bp band in the + spike and − spike reactions. These results demonstrate that mouse #44 is heterozygous for the interrupted allele. In the control PCR reactions, no product was evident when template was not included. PCR products of 364 bp and 255 bp were evident when pNeoαGT10.8B and Exon 9 RT-PCR DNA were the only templates included in the control reactions.

EXAMPLE 15

Characterization of Homozygous Knockout Mice

I. Absence of Gal T mRNA in Gal T Knockout Mice
A. RNA Isolation

Total RNA was extracted using the RNAzol™ B kit (BIOTECX Laboratories, Inc., 6023 South Loop East, Houston, Tex. 77033, USA.), supplied by Bresatec. This extraction procedure is based on the method described by Chomczynski et al., Anal. Biochem. 162: 156–159 (1987), and involves homogenization in a guanidinium/phenol solution, a chloroform extraction, 2 isopropanol precipitations, and 75% EtOH washes. The RNA was stored as an EtOH precipitate at −20° C. and quantitated by measuring absorption at wavelength 260 nm in water. The integrity and quantitation was confirmed by electrophoresis in agarose/formaldehyde gels. Sambrook et al. *Molecular Cloning, A Laboratory Manual.* Second Edition. (1989)

B. RT-PCR

First strand cDNA synthesis involved:
annealing 2 μg of total RNA from kidney, heart or liver with 120 ng oligo dT primer (Gibco BRL, M-MLV Reverse Transcriptase Kit) at 65° C. for 5 minutes in 5 μl of 10 mM Tris-HC1, 1 mM EDTA (pH8)
reverse transcription at 37° C. for 1–2 hours in a final reaction volume of 20 1l utilizing the M-MLV Reverse Transcriptase Kit(Gibco BRL). Each reaction contained 5 mM DTT, 0.1 μg/μl BSA, 1 mM dNTPS, 40 U of human placental RNAse Inhibitor (Bresatec), 200 U of M-MLV Reverse Transcriptase and the associated RTase buffer at 1× concentration.

C. PCR Analysis of cDNA

α-1,3-Gal T cDNA was detected by PCR amplification of oligo dT-primed cDNA template. Failure to generate this PCR fragment, in conjunction with the control PCR results, indicated that α-1,3-Gal T mRNA was absent from the RNA preparation. To demonstrate that the α-1,3-Gal T primers supported amplification of the α-1,3-Gal T template, each reaction was assembled in duplicate, and one of the reactions was spiked with 0.1 fg (~100 molecules) of a 983 bp mouse α-1,3-Gal T cDNA product (generated by primers 7F and mGT-3UR, spanning exon 7 to the 3' untranslated region). As a second control to demonstrate that cDNA synthesis had occurred, a ferrochelatase PCR fragment was generated from the cDNA template.

1. Primers:
Primers to detect α-1,3-Gal T cDNA:

7F: 5'-TGGAGATCGCATTGAAGAGC 3' (SEQ ID NO: 20)

(corresponding to nucleotides 889–911 within exon 7 (FIG. 4)

9R2: 5'-TGGCCGCGTGGTAGTAAAAA 3' (SEQ ID NO: 21)

(corresponding to nucleotides 1492–1511 within exon 9 (FIG. 4)

Primers 7F and 9R2 were expected to generate a fragment of ~619 bp (FIG. 23) from the cDNA template. These primers will not generate a fragment from genomic DNA possibly present in the cDNA preparation, since the primers span two large introns.

mGT-3UR: 5'-GGGTTTTGGTTTTGATTGTT 3' (SEQ ID NO: 22)

(corresponding to nucleotides 1866–1888 within the 3' untranslated region; FIG. 4).

This primer was used with primer 7F to generate the DNA fragment used in the control spike PCRs.

Primers to detect mouse ferrochelatase cDNA (EcoRI linkers, underlined):

FC-F: 5'-CTGAATTCATGTTAAACATGGGAGGCCCC 3' (SEQ ID NO: 23)

(corresponding to nucleotides 215–235, Taketani et al., J. Biol. Chem. 265: 19377–80 (1990)).

gFC-R: 5'-CTGAATTCTGCCCACTCCCTGCCGATG 3' (SEQ ID NO: 24)

(corresponding to nucleotides 888–908, Taketani et al., J. Biol. Chem. 265: 19377–80 (1990)).

Figure 23:
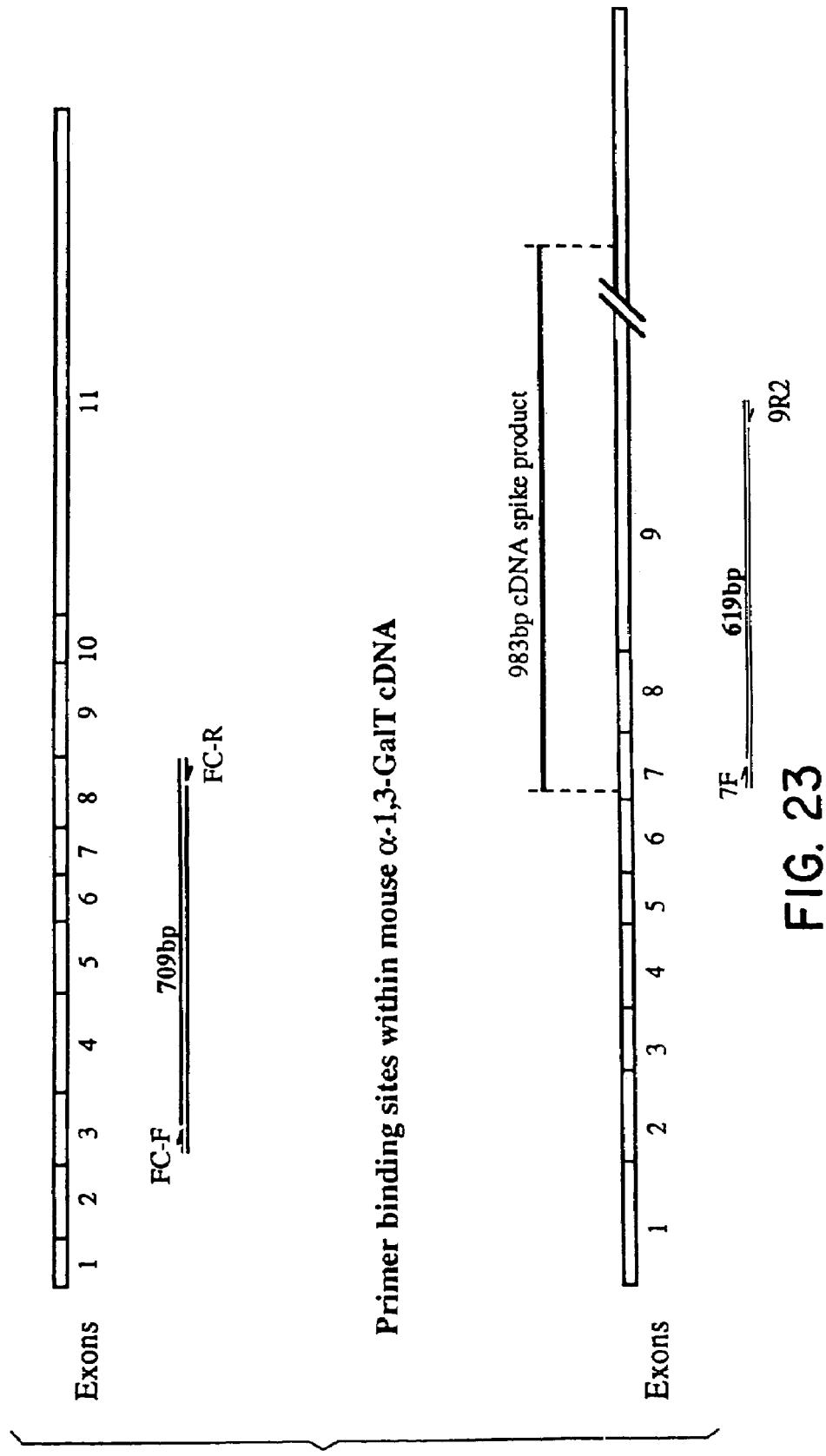
FIG. 23 depicts the PCR products expected from PCR analysis of cDNA generated from α-1,3-GalT mA in normal and knockout mice. The ferrochelatase primers and PCR fragment represent a control demonstrating that cDNA synthesis had occurred.

These primers were expected to generate a 709 bp fragment (FIG. 23). These primers will not generate a fragment from genomic DNA possibly present in the cDNA preparation, since the primers span five introns.

Reaction volumes were 50 μl, consisting of 4 μl of the first strand cDNA synthesis reaction, 100 ng of each primer, 2 mM $MgCl_2$, 0.3 mM dNTPS, 2 U of Taq-Polymerase (Bresatec) and Taq reaction buffer (Bresatec) at 1× concentration. Reactions were heated at 94° C. for 2 min, then 29 cycles of 94° C. for 15 sec, 58° C. for 30 sec and 72° C. for 1 min followed by single steps of 72° C. for 4 min and 4° C. for 5 min. A 10 μl aliquot of each PCR was electrophoresed on a 2% agarose gel and DNA fragments were visualized on a UV light box after staining the gel with ethidium bromide.

FIG. 24 shows the PCR fragments generated from RNA isolated from kidney (K), heart (H) and liver (L) of a wild-type mouse, and mice heterozygous or homozygous for the interrupted α-1,3-Gal T allele. FIG. 24(i) shows that the 709 bp ferrochelatase fragment was generated from each of the cDNA preparations, indicating that cDNA template was produced from the reverse transcription reaction, and was available for the α-1,3-Gal T gene primers. The 619 bp α-1,3-Gal T fragment was present in each of the reactions spiked with the 983 bp α-1,3-Gal T cDNA product (FIG. 24(ii)), indicating that amplification of the α-1,3-Gal T cDNA (spike) template had occurred.

In the reactions that were not spiked (FIG. 24 (iii)), the 619 bp α-1,3-Gal T fragment was detected in cDNAs synthesized from the wild-type and heterozygous RNAs. This indicates that α-1,3-Gal T mRNA is present in the kidney, heart and liver of the wild-type and heterozygous mice. The 619 bp fragment was not detected in the unspiked homozygous KO reactions, indicating that α-1,3-Gal T mRNA is not synthesized in the homozygous KO mice.

II. Test for Expression of the GAL Epitope in Homozygous Knockout Mice Using Anti-Gal Antibodies with Fluorescence-Activated Cell Sorting (FACS)

A. Solutions

Solutions 1 to 5 are 10× isotonic.

1. 1.68 M NaCl (948.21 g/l) Dry salts overnight in hot oven before weighing 2. 1.68 M KCl (125 g/l) Dry salts overnight in hot oven before weighing 3. 1.12 M $CaCl_2$ (165 g/l $CaCl_2 2H_2O$) Dry salts overnight in hot oven before weighing 4. 1.68 M $MgSO_4$ (414 g/l $MgSO_4 7H_2O$) Do not dry in hot oven 5. Potassium phosphate buffer pH 7.2:
  a) 1.68 M $KH_2PO_4$ (229 g/L)
  b) 1.12 M $K_2HPO_4$ (226 g/L $K_2HPO_4$ $3H_2O$ or 195 g/l $K_2HPO_4$)

Potassium phosphate buffer is prepared by mixing together equal volumes of solutions a) and b). To pH the buffer, remove a small sample, dilute 1:50 and read on pH meter.

6. Hepes buffer 1 M (CSL, Melbourne Australia)
7. KDS BSS:

Add stock solutions in the following order to double-distilled water (DDW):

| Stock | Ratio of Solutions |
| --- | --- |
| DDW | 1210 |
| NaCl | 121 |
| KCL | 3 |
| $CaCl_2$ | 3 |
| $MgSO_4$ | 1 |
| Potassium phosphate buffer | 2 |
| Hepes | 20 |

Filter Sterlise, store at 4° C.

8. KDS/BSS/2% HSA/0.02% azide:

| KDS/BSS | 244.5 ml |
| --- | --- |
| Human serum albumin (CSL, Melbourne, Australia) | 5 ml |
| 10% Na azide in MT-PBS | 0.5 ml |

9. FITC dilution: Dilute 7.5 ul FITC-IgG to 600 ul with KDS/BSS

10. Red cell lysis buffer:
0.168 M $NH_4Cl$ in double distilled water 11. 4% paraformaldehyde (PFA)

| Solutions: | | |
| --- | --- | --- |
| A. | $NaH_2PO_4 2H_2O$ | 22.6 g/L |
| B. | NaOH | 25.2 g/L |
| C. | 40% paraformaldehyde: 1) 4 g paraformaldehyde (BDH, Kilsyth, Australia, #29447) dissolved in 10 ml double distilled water. Heat 70° C. 2 hours on stirrer in fume hood and a few drops of 2M NaOH are added until the solution becomes clear. 2) 0.54 g glucose is then added. 3) Store RT in light proof bottle. | |
| D. | Add together 83 ml of A + 17 ml of B. | |
| E. | Final 4% PFA fixative solution: 90 ml of D + 10 ml of C. pH 7.4–7.6; adjust pH with 1M HCl. | |

12. Hanks Balanced Salt Solution (Ca and Mg free) (HBBS):

| KCL | 400 mg |
| --- | --- |
| $KH_2PO_4$ | 60 mg |
| NaCl | 8 g |

-continued

| | |
|---|---|
| NaHCO3 | 350 mg |
| Na$_2$HPO$_4$2H$_2$O | 68 mg |
| Glucose | 1 g |
| H$_2$O | to 1 liter | adjust to pH 7.0; filter sterilize

13. Sheep antihuman IgG and IgM fluorescein isothiocyanate (FITC) F(ab)2 fragments (Silenus, Hawthorn, Australia):

B. Methods

1. Eye bleed mice, collect 300–400 ul into pre-chilled Ependorf tube, store on ice, add EDTA 20 mg/ml to give final concentration of 2 mg/ml.

2. Transfer blood (including appropriate human controls) to 10 ml plain tube and add 10 ml red cell lysis buffer (0.168 M NH$_4$Cl) pre-warmed to 42° C.; incubate for several minutes or until cells have lysed.

3. Pellet cells by centrifugation (800×g, 7 min, 4° C.).

4. Resuspend cells in 10 ml KDS/BSS/2% HSA/0.02% NaN$_3$

5. Pellet cells as above; repeat steps 4 & 5.

6. Resuspend cells in 1000 ul KDS/BSS/2% HSA/0.1% NaN$_3$; transfer aliquots to V bottom FACS tubes.

7 Pellet cells as above.

8. Resuspend cells in 100 ul KDS/BSS/2% HSA/0.1% NaN$_3$

9. Add 50 ul of purified anti-GAL antibody (see Example 1, above), normal human serum (NHS) or HBBS/2% HSA/0.1% NaN$_3$ and incubate 45 min.

10. Add 2 ml KDS/BSS/2% HSA/0.02% NaN3; centrifuge cells as above.

11. Add 50 ul of a 1:80 dilution of sheep antihuman IgG or IgM FITC F(ab)$_2$ fragment (Silenus).

12. Add 2 ml KDS/BSS/2% HSA/0.02% NaN3; centrifuge cells as above.

13. Resuspend cells in 300 ul KDS/BSS/2% HSA/0.02% NaN3.

14. Transfer samples to plastic round-bottom FACS tubes and add 3 ul of propidium iodide (100 ug/ml); samples are now ready for analysis; keep on ice.

15. Analyse on Beckman FACS scan using peripheral blood lymphocyte settings.

C. Results

The results of these experiments are given below:

| | median channel fluorescence (log scale) | peak channel fluorescence (log scale) |
|---|---|---|
| MOUSE 129 (Normal) PBL + FITC anti-IgG alone (neg. control) | 9 | 9 |
| MOUSE 19 PBL (wild type) GAL IgG | 197 | 286 |
| MOUSE 21 PBL (Gal KO) GAL IgG | 22 | 15 |
| MOUSE 129 (Normal) PBL + FITC anti-IgM alone (neg. control) | 7 | 1 |
| MOUSE 19 PBL (wild type) GAL IgM | 185 | 167 |
| MOUSE 21 PBL (Gal KO) GAL IgM | 34 | 18 |
| MOUSE 129 PBL (normal) PBL + FITC IgG alone (neg. control) | 8 | 9 |
| MOUSE 129 PBL (normal) GAL IgG | 120 | 328 |
| MOUSE 9 PBL (Gal KO) GAL IgG | 10 | 9 |

The results of human anti-Gal binding to human peripheral blood lymphocytes (negative control) are not shown but were negative. These experiments demonstrate that human anti-Gal (IgG and IgM) antibodies bind to peripheral blood cells of the homozygous α1,3 galactosyltransferase knockout mice (mouse 21 and mouse 9) very weakly if at all. This confirms the expected lack of the galactose α1,3 galactose (GAL) epitope in such mice. In contrast, peripheral blood cells of normal mice (mouse 129 and mouse 19) of the same strain display clear binding of anti-Gal antibodies.

III. Test for Expression of the GAL Epitope in Homozygous Knockout Mice Using IB$_4$ Lectin with FACS IB$_4$ Lectin has an exclusive affinity for terminal α-D-galactosyl residues, and is demonstrated below to be useful for characterizing the knockout mice.

A. Solutions 1. 4% paraformaldehyde (see above)
2. Mouse Tonicity PBS (MT-PBS)

| | |
|---|---|
| Na$_2$HPO$_4$ | 2.27 g |
| NaH$_2$PO$_4$2H$_2$O | 0.62 g |
| NaCl | 8.7 g |

Make up to 1 liter with DDW

3. Dead Cell Removal Buffer (DCRB):
   4.5 g Sorbitol
   7.6 g Glucose monohydrate, (6.93 g if anhydrous)
   12.5 ml KDS/BSS
   Make up to 100 ml with DDW
   Filter, store at 4° C.
   Open only under sterile conditions
4. KDS/BSS (Mouse Tonicity, Hepes Buffered Balanced Salt Solution pH 7.2) (see above)
5. Red cell lysis buffer (see above)
6. KDS/BSS/2% HSA/0.02% azide (see above)
7. Hanks Balanced Salt Solution (Ca and Mg free) (see above)

B. Methods

1. Remove spleen, hold with curved forceps and collect splenocytes by injecting with a 27 gauge needle bent at 90° C., injecting (2.5 ml syringe) 100–200 ul buffer into the spleen two or three times. Using the flat surface of the bent needle massage cells out of holes made in spleen. Repeat injections and removal of cells until no cells remain in capsule.

2. Transfer splenocytes to 10 ml tube and centrifuge to pellet cells (500×g, 7 min, 4° C.).

3. Remove supernatant and add 3 ml red cell lysis buffer pre-warmed to 42° C.; incubate for several minutes or until cells have lysed. Underlay with 1 ml HIFCS (heat inactivated fetal calf serum) and stand on ice 5 minutes. Top to 10 ml with KDS BSS/10% HIFCS.

4. Centrifuge as above.

5. Resuspend cells in 3 ml dead cell removal buffer; mix well with pipette.

6. Pass through a glass pipette plugged with cotton wool and collect cells into a 10 ml tube. Don't force cells through, allow to drain under gravity.

7. Underlay cells with 1 ml BSS/10% HIFCS.

8. Centrifuge as above.

9. Remove supernatant.

10. Centrifuge as above; repeat steps 4 & 5.

11. Add 0.5 ml cold 4% paraformaldehyde (PFA).

12. Incubate on ice for 5 min with intermittent mixing.

13. Add 2 ml ice cold HBBS and centrifuge as above.

14. Repeat washings with 2 ml and then 1 ml HBBS.

15. Resuspend cells in 10 ul KDS/BSS/2% HSA/01.% $NaN_3$; transfer to V bottom FACS tubes.

16. Add FITC IB4 lectin (Sigma, Cat. No. L 2895), 50 ul at 20 ug/ml, or 50 ul HBBS; incubate on ice for 30 min.

17. Add 2 ml KDS/BSS/2% HSA/0.1% $NaN_3$; spin cells as above.

18. Resuspend cells in 300 ul KDS/BSS/2% HSA/0.1% NaN3.

19. Transfer samples to plastic round-bottom FACS tubes; samples are now ready for analysis; keep on ice.

20. Analyse on FACS scanner using peripheral blood lymphocyte setting.

C. Samples

1. Mouse 129 splenocytes alone
2. Mouse 129 splenocytes+IB4 lectin
3. human PBL alone
4. Human PBL+IB4 lectin D. Results Results of these experiments are given below:

| | mean fluorescence channel (log scale) | median fluorescence channel (log scale) | peak fluorescence channel (log scale) |
|---|---|---|---|
| splenocytes alone (autofluorescence) | 1 | 1 | 1 |
| mouse 19 (wild type) splenocytes | 252 | 58 | 16 |
| mouse 21 (KO mouse) splenocytes | 3 | 2 | 1 |

The results demonstrate that IB4 lectin binds spleen cells of the homozygous α1,3 galactosyltransferase gene targeted (Gal KO) mouse (mouse 21) very weakly if at all. This confirms the expected lack of the galactose α1,3 galactose (GAL) epitope in such mice. In contrast, peripheral blood cells of a normal mouse (mouse 19) of the same strain binds $IB_4$ lectin strongly.

IV. Immunohistological Assessment of Mouse Tissues for the Presence of the Gal Epitope Using ANTI-GAL Antibodies.

A. Reagents

| 1. TBS: Tris Buffered Saline | |
|---|---|
| NaCl | 8 g |
| KCl | 0.2 g |
| Tris base | 3 g | dissolve in 800 ml distilled water. Adjust pH to 8.0 with 1 M HCl. Adjust volume to 1 L. Sterilise by autoclaving. Store at RT.

2. Blocking Buffer:

TBS+2% bovine serum albumin (BSA)+10% rabbit serum:

3. Peroxidase Conjugates:

DAKO (Denmark) peroxidase (POD) conjugated to rabbit anti-human IgG(fragment) and DAKO (Denmark) peroxidase (POD) conjugated to rabbit anti-human IgM (fragment).

Conjugates were both separately pre-absorbed on 10% mouse liver powder at 4° C. overnight, then centrifuged at 18,000×g for 10 minutes in a Biofuge and then at 30 psi for 30 min in a Beckman airfuge. Conjugated antisera were diluted 1/50 in 2% blocking buffer (TBS+0.2% BSA+2% rabbit serum) with 16% normal mouse serum.

4. Mouse Liver Powder Preparation:

As modified from Antibodies, a Laboratory Manual Ed Harber and David Lane, Cold Spring Harbour Laboratories (1988) p663:

a) Prepare a fine suspension of mouse liver in mouse tonicity phosphate buffered saline (MT-PBS). Mash liver through a sieve with a 5 ml plunger. Discard any fibrous tissue. One gram of tissue should be resuspended in approximately 1 ml MT-PBS.

b) Transfer the tissue/saline suspension to ice for 5 min.

c) Add 8 ml of acetone (−20° C.) (Univar 6, Ajax Chemicals) for 10 minutes. Mix vigorously. Incubate on ice for 30 minutes with occasional vigorous mixing.

d) Collect the precipitate by centrifugation at 10,000 g (9,000 rpm in Sorvall RC-5B refrigerated superspeed centrifuge). Spin for 10 minutes.

e) Resuspend the pellet with fresh acetone (−20° C.) and mix vigorously. Allow to sit on ice for 10 minutes.

f) Centrifuge at 10,000 g for 10 minutes. Transfer the pellet to a clean piece of filter paper. Spread the precipitate and allow to air-dry at room temperature.

g) After the pellet is dry, transfer it to an airtight container. Remove any large pieces that will not break into a fine powder. Dessicate and store at 4° C. Yield as approximately 10–20% of the original wet weight. To use acetone powders, add to a final concentration of 1%. Incubate for 30 min at 4° C. Spin at 10,000 g for 10 minutes. (13,000 rpm in Biofuge)

5. DAB/$H_2O_2$/Imidazole:

Peroxidase substrate: 3,3'-Diaminobenzidine tetrahydrochloride (DAB) (Sigma, Missouri)

1 tablet DAB (take out of fridge 10 min before use)

1 tablet urea $H_2O_2$ (Sigma, Missouri)

add to 15 ml tris HCL, pH 7.6+0.01M imidazole (0.0102 g), (Sigma, Missouri)

make up immediately before use

6. Tris HCL:

1.211 g Tris in 200 ml double distilled water pH 7.6

7. Animal Serum Sources:

Mouse and rabbit sera were obtained in-house (St. Vincent's Hospital, Dept. of Clinical Immunology).

Sheep serum was obtained from the University of Melbourne Veterinary Clinic and Hospital, Werribee, Australia.

8. Harris Haematoxylin:

Haematoxylin C.I. 75290 (BDII, Poole, U.K. #34037) 10 g
Absolute ethanol 200 ml
Potassium alum 200 g
double distilled water 2000 ml
glacial acetic acid 80 ml Preparation:
1. Dissolve haematoxylin in absolute ethanol
2. Heat to dissolve alum in double distilled water
3. Mix solution 1 and 2
4. Immediately before use add 80 ml 1% sodium iodate and 80 ml glacial acetic acid

9.

| 9. Scott's Tap Water: | |
|---|---|
| Sodium hydrogen carbonate | 14 g |
| MgSO$_4$ | 80 g |
| Tap water | 4 liters |

B. Methods
1. Cut 4 um sections of the relevant tissue on cryostat
2. Tissue should be free of cracks
3. Air dry slides for 30 min
4. Apply 10% blocking buffer at room temp in humidified chamber, 60 min
5. Remove blocking antibody with tissue made to fine point
6. Apply 1st antibody, anti-GAL, or 2% blocking buffer as control, 50 ul, ensure no air bubbles and incubate at room temp in humidified chamber for 30 min
7. Wash off with Tris buffered saline (TBS) 3 times 2 minutes washes
8. Apply second antibody 1:50 peroxidase (POD) conjugated rabbit anti-human IgG and IgM (DAKO, Denmark); incubate 30 min at room temp in humidified chamber
9. Wash off with Tris buffered saline (TBS) 3 times 3 minute washes
10. Wash off with TBS as above
11. Incubate DAB/H$_2$O$_2$/imidazole for 10 minutes
12. Wash in water
13. Stain with haemotoxylin C-10 seconds
14. Wash in water
15. Place in Scotts tap water for 15 seconds
16. Wash in water
17. Wash in absolute alcohol (×3) (Univar 214, Ajax chemicals)
18. Wash in absolute xylene (×3) (Univar 577, Ajax chemicals)
19. Coverslip using automatic coverslip machine (Tissue Tek)

Controls:
1. Buffer only+POD conjugated rabbit anti-human IgM (negative)
2. Buffer only+POD conjugated rabbit anti-human IgG (negative)
3. Human kidney (negative)
4. Pig renal cortex (positive)

Samples:
1. Mouse 129 SV (control) kidney.
2. mouse 9 (Gal Knockout) kidney
3. mouse 21 (Gal Knockout) kidney C. Results

| KIDNEY | | | |
|---|---|---|---|
| | GLOMERULI | ENDOTHELIUM | comments |
| MOUSE 129 anti-IgM | POSITIVE | POSITIVE | |
| MOUSE 9 anti-IgM | NEGATIVE | NEGATIVE | weak adventitial staining |
| MOUSE 21 anti-IgM | NEGATIVE | NEGATIVE | weak adventitial staining |
| MOUSE 129 anti-IgG | POSITIVE | POSITIVE | |
| MOUSE 9 anti-IgG | NEGATIVE | NEGATIVE | |
| MOUSE 21 anti-IgG | NEGATIVE | NEGATIVE | |
| POD conjugated antibody alone | ALL NEGATIVE | ALL NEGATIVE | |

These results indicate that human anti-Gal IgG and IgM antibodies do not bind kidney tissue of the α1,3 galactosyltransferase gene targeted (Gal KO) mice (mouse 21 and mouse 9). This confirms that lack of the galactose α1,3 galactose (GAL) epitope in the gene targeted (KO) mice. In contrast, these antibodies react strongly with the endothelium of blood vessels and the glomeruli of a normal mouse of the same strain (129).

V. Immunohistological Examination of Mouse Tissues Using IB$_4$ Lectin

A. Reagents
1. Blocking buffer: TBS+2% BSA+10% sheep serum
2. FITC IB$_4$ (Sigma, Missouri, USA #L-2895)
   1 mg diluted in 1 ml HBBS to give stock solution, then dilute to final volume of 20 ug/ml in TBS+2% BSA+2% sheep serum
3. Peroxidase anti-FITC
   Boehringer anti-fluorescein POD Fab fragments; dilute 1/300 in 2% blocking buffer
4. DAB/H$_2$O$_2$/Imidazole—see above
5. Tris HCL—see above
6. Animal serum sources—see above
7. Harris Haematoxylin—see above
8. Scott's Tap Water—see above B. Methods
1. Preparation of Sections; same as Section 4B, steps 1–7 above.
2. Apply 50 μl FITC conjugated IB4 (Sigma # 1–2894) 20 μg/ml, incubate in a humidified chamber for 30 minutes.
3. Wash with TBS, 3 minutes (×3).
4. Apply 50 μl per oxidase conjugated anti-FITC Fab fragments (Boehringer Mannheim), diluted 1–3—with TBS+2% BSA+2% sheep serum. Incubate for 30 minutes in humidified chamber.
5. Wash with TBS, 3 minutes (×3).
6. Processing for microscopy—same as Section IVB steps 14–22.

Controls
1. Buffer only+POD anti-FITC (negative)
2. Human kidney (negative)
3. Pig renal cortex (positive)

Samples 1st Experiment
1. Mouse 129 SV normal mouse heart liver kidney lung
2. mouse 6 wild type heart liver kidney lung
3. mouse 7 heterozygote KO heart liver kidney lung
4. mouse 9 homozygous KO heart liver kidney lung Samples 2nd Experiment
1. mouse 19 wild type heart liver-kidney lung
2. mouse 20 heterozygote KO heart liver kidney lung
3. mouse 21 homozygous KO heart liver kidney lung C. Results

| Kidney | | |
|---|---|---|
| | GLOMERULI | ENDOTHELIUM |
| HUMAN | NEGATIVE | NEGATIVE |
| PIG | POSITIVE | POSITIVE |
| 129 MOUSE | POSITIVE | POSITIVE |
| MOUSE 6 | POSITIVE | POSITIVE |
| MOUSE 7 | POSITIVE | POSITIVE |
| MOUSE 9 | NEGATIVE | NEGATIVE |
| MOUSE 19 | POSITIVE | POSITIVE |
| MOUSE 20 | POSITIVE | POSITIVE |
| MOUSE 21 | NEGATIVE | NEGATIVE |
| anti-FITC alone | ALL NEGATIVE | ALL NEGATIVE |

| Liver | | |
|---|---|---|
| | ENDOTHELIUM | BILE DUCT |
| 129 MOUSE | POSITIVE | POSITIVE |
| MOUSE 6 | POSITIVE | POSITIVE |
| MOUSE 7 | POSITIVE | POSITIVE |
| MOUSE 9 | NEGATIVE | NEGATIVE |
| MOUSE 19 | POSITIVE | POSITIVE |
| MOUSE 20 | POSITIVE | POSITIVE |
| MOUSE 21 | NEGATIVE | NEGATIVE |
| anti-FITC alone | ALL NEGATIVE | ALL NEGATIVE |

| Heart | | | |
|---|---|---|---|
| | ENDOTHELIUM | PERINUCLEAR | ENDO-MYOCARDIUM |
| 129 MOUSE | POSITIVE | POSITIVE | POSITIVE |
| MOUSE 6 | POSITIVE | POSITIVE | POSITIVE |
| MOUSE 7 | POSITIVE | POSITIVE | POSITIVE |
| MOUSE 9 | NEGATIVE | NEGATIVE | NEGATIVE |
| MOUSE 19 | POSITIVE | POSITIVE | POSITIVE |
| MOUSE 20 | POSITIVE | POSITIVE | POSITIVE |
| MOUSE 21 | NEGATIVE | NEGATIVE | NEGATIVE |
| anti-FITC alone | ALL NEGATIVE | ALL NEGATIVE | ALL NEGATIVE |

| Lung | | | |
|---|---|---|---|
| | ENDOTHELIUM | BRONCHI | PARENCHYMA |
| 129 MOUSE | POSITIVE | POSITIVE | POSITIVE |
| MOUSE 6 | POSITIVE | POSITIVE | POSITIVE |
| MOUSE 7 | POSITIVE | POSITIVE | POSITIVE |
| MOUSE 9 | NEGATIVE | NEGATIVE | NEGATIVE |
| MOUSE 19 | POSITIVE | POSITIVE | POSITIVE |
| MOUSE 20 | POSITIVE | POSITIVE | POSITIVE |
| MOUSE 21 | NEGATIVE | NEGATIVE | NEGATIVE |
| anti-FITC alone | ALL NEGATIVE | ALL NEGATIVE | ALL NEGATIVE |

These results indicate that $IB_4$ lectin does not bind kidney, heart, liver or lung tissue of the α1,3 galactosyltransferase gene targeted (Gal KO) homozygous mice (mouse 21 and mouse 9). This confirms the lack of the galactose α1,3 galactose (GAL) epitope in the gene targeted (KO) mice. In contrast these antibodies react strongly with the tissues of a normal mouse and heterozygous KO mice (mouse 129, mouse 6, mouse 7, mouse 19, mouse 20) of the same strain.

VI. Resistance of Spleen Cells from Knockout Mice to Lysis by Human Serum

Lysis of spleen cells by human serum was tested through use of a $^{51}$chromium release assay. See in general Example 4, above.

A. Preparation of Mouse Splenocytes—Shortman, K. J. et al, Immunological Methods. 1:273–287 (1972).:

Dissect out spleen, avoid damaging outer membranes and carefully remove mesentery tissue and fat.

Place in petri dish, with 1 ml RPMI 1640 (Gibco BRL)/10% Heat-inactivated foetal calf serum (HI-FCS). (Heat-inactivation=40 Min at 56° C.).

Gently tease out cells into petri dish, collect and centrifuge 500×g, 5 min, 4° C.

Remove RPMI/10% HIFCS, gently resuspend cells in 3 ml 0.9% NH4C1 (0.168M), using a Pasteur pipette. (Use Pasteur pipettes or wide-bore pipettes for all re suspension and transfer procedures)

Transfer to 10 ml tube, underlay with 1 ml HIFCS, stand on ice, 5 min.

Transfer supernatant to clean tube, centrifuge 500×g, 7 min, 4° C.

Discard supernatant, re-suspend cells in 3 ml dead cell removal buffer, mix well with pipette.

Pass through cotton wool plug in glass pipette (under gravity, do not force through), collect cells into 10 ml tube.

Underlay cells with 1 ml HI-FCS.

Centrifuge 500×g, 1 min, 4° C.

Remove supernatant, re-suspend cells in 50 μl RPMI, 10% HI-FCS. Store cells on ice.

B. Preparation of Serum:

Human—Collect whole blood from a pool of normal donors; allow to stand at room temp. for 2 hours.

Wring the clot with an 'Orange stick'; spin Remove and pool serum. Store half at −70° C. in 3 ml aliquot's (normal human serum); heat-inactivate the other half, see below.

Fetal calf serum—purchased from Gibco BRL, and stored at −20° C.

C. Cell Counting:

1. Add 5 μl cells to 95.0 μl RPMI, 10% HI-FCS
2. Remove 10 μl cells, add 10 μl Acridine Orange/Et Br solution, (Lee, S. K. et al. Eur J. Immunol. 1975. 5: 259–262)
3. Count cells, (viable=green, deads=orange).
4. Cell viability should be approx. 90–100%
5. Calculate cell number.

D. $^{51}$Chromium Labelling:

| Cell Type | Incubation conditions | |
|---|---|---|
| | Time | Amount$^{51}$Cr/$10^7$ cells |
| Freshly prepared cells: (eg., splenocytes or lymphocytes) | ~2 hours | ~150–300 μCl |
| Cultured Cells: | ~1 hour | ~100 μCl |

Labelling:
 Combine:
  cells (2×10$^7$)
  ($^{51}$Cr) Sodium Chromate in 0.9% NaCl solution (the volume added depends on cell type as indicated above and on the specific activity of the —(51Cr) Sodium Chromate).
  RPMI/2% HIFCS up to a total of 200 μl
  Incubate at 37° C. for time shown above with gentle agitation every 15 min.
 E. Washing
  Place 4 ml HI-FCS into 10 ml tube and carefully layer labelling reaction on top with a swirling motion; centrifuge 5 min, 500×g, 4° C.
  Remove top two layers with a careful circular motion using a glass pipette.
  Resuspend cells in 1 ml RPMI/2% HI FCS
  Pellet cell suspension through another 4 ml HI FCS
  Resuspend cell pellet in 1 ml RPMI/2% HI FCS, store on ice.
 F. Release Assay:
  Perform assay in 96-well microtire plate (ICN-FLOW).
  Assay should be set up in quadruplicate.
  Assay is performed in a total volume of 180 μl.

Assay:

| | NHS | *HI-NHS | 16% SDS | CELLS | RPMI/ 2% HIFCS |
|---|---|---|---|---|---|
| MAX Release | — | 90 μl | 22.5 μl | 25 μl | 42.5 μl |
| Spont. Release | — | 90 | | 25 | 65 μl |
| 5% NHS | 9 μl | 81 | | 25 | 65 |
| 10% NHS | 18 | 72 | | 25 | 65 |
| 20% NHS | 36 | 54 | | 25 | 65 |
| 30% NHS | 54 | 36 | | 25 | 65 |
| 40% NHS | 72 | 18 | | 25 | 65 |
| 50% NHS | 90 | — | | 25 | 65 |

*HI = heat inactivated

All volumes indicated are in μl
Reaction components are added to the plate in the order: RPMI, Serum and $^{51}$Cr-labelled cells.
Cover plate with plate-sealer
Incubate, 4 hours, 37° C.
Spin plate, 1500 rpm, 0.5 min.
Remove plate-scaler, remove 80 μl from each wall, count released chromium on gamma counter.

Calculate specific lysis for each well according to the formula:

$$\% \text{ Specific Lysis} = \frac{(\text{Test cpm} - \text{Spontaneous release cpm})}{(\text{Maximal release cpm} - \text{Spontaneous release cpm})} \times 100$$

Calculate mean and standard deviation for each experimental point. Graph % Human serum (X axis) against % Specific lysis (Y axis) for each type of cell (wild type, heterozygote KO and homozygous KO)

Figure 25:
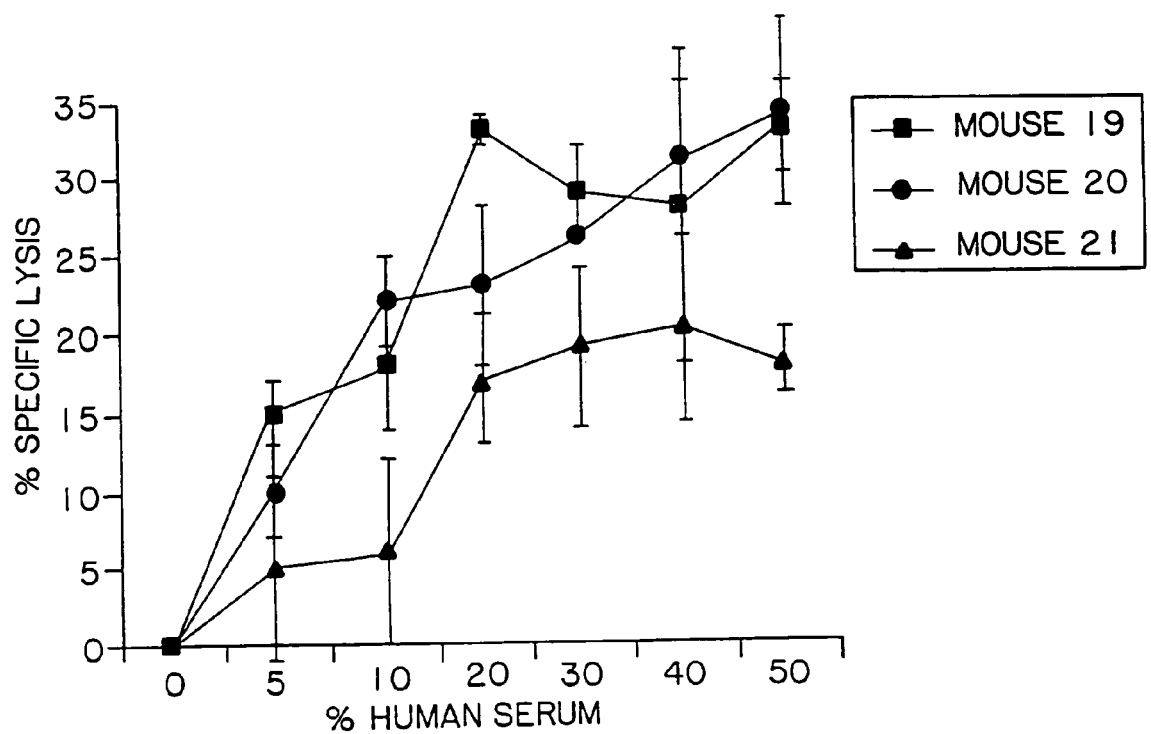
FIG. 25 is a graphical representation of the relative protection of spleen cells, derived from GalT knockout mice, from lysis by human serum.

The results of these experiments are depicted in FIG. 25. The results indicate that spleen cells from a homozygous knockout mouse are relatively resistant to lysis by human serum, in comparison to spleen cells derived from mice heterozygous for the interrupted allele or from wild-type mice.

EXAMPLE 16

Generation of Knockout Animals Through Microinjection of Eggs

Transgenic animals are generated routinely by microinjection of DNA into the pronuclei of fertilised eggs. Generally this technology results in the random integration of the transgene in the genome. However, conventional transgenic technology has resulted in homologous recombination between the injected transgene and the endogenous gene. See, for example, Brinster et al., Proc. Nat. Acad. Sci. USA 86: 1087–91 (1989). Described below are procedures for inactivating the α-1,3-Gal T gene in pigs through microinjection of eggs with gene targeting constructs.

I. Gene Targeting Constructs

The frequency of homologous recombination in embryos is improved if the gene targeting constructs are prepared with isogenic DNA. Therefore the "knock out" constructs are prepared from DNA isolated from the boar used to fertilize the oocytes used for microinjection. DNA is isolated from the tail or ear tissue, and genomic fragments from both α-1,3-Gal T alleles of the boar, encompassing exons 8 & 9 are cloned using long range PCR or conventional genomic library technologies. Clones for each of the α-1,3-Gal T alleles are identified using restriction fragment length polymorphism identification and DNA sequencing. Constructs to target both alleles are made by interrupting the coding sequence of exon 9, either by deletion or by inserting a heterologous DNA fragment. The constructs contain at least 8 kb of homologous DNA to promote efficient homologous recombination.

Various approaches can be used to detect gene targeting events, depending on the strategies used in designing the knockout constructs. Several such approaches, and the corresponding strategies for construction of constructs, are provided below:
 a) PCR of Genomic DNA:
  Homologous DNA on one side of the interrupting DNA fragment is constructed to be less than 1 kb, allowing PCR amplification of a short diagnostic fragment. (Amplification of small fragments generally is relatively efficient).

b) Reverse Transcription/PCR:

A deletion of about 100 bp within exon 9 is made, allowing synthesis of a shortened α-1,3-Gal T mRNA in correctly targeted cells. The shortened mRNA is detected by RT/PCR, using primers that amplify a fragment extending from exon 8 and encompassing the deletion site.

c) Green Fluorescent Protein (GFP) Gene Expression:

GFP is a protein from the bioluminescent jelly fish *Aequorea victoria*. It absorbs blue light. (395 nm) and fluoresces to emit green light (509 nm). GFP is a useful marker for gene expression. Chafie et al., Green Fluorescent Protein as a Marker for Gene Expression. Science 263: 802–5 (1994). The α-1,3-Gal T gene is interrupted within exon 9 by in-frame insertion of the GFP coding region. Expression of the GFP gene (with resulting fluorescence at 509 nm) is driven by the α-1,3-Gal T gene promoter in correctly targeted cells.

II. Generating Embryos for Microinjection

Fertilized embryos are generated as described by Nottle et al., (1993). Proc Aust Soc for Reproductive Biol 26, 33. The protocol involves:

a) Sperm from the boar providing DNA for the targeting construct is collected and stored frozen in liquid $N_2$.

b) Superovulation of Donor Gilts:

Gilts are mated at the second oestrus, and aborted between days 25–40 days of gestation to synchronise the subsequent oestrus cycles. Abortion is achieved by intramuscular injection of 1 mg cloprostenol (a prostaglandin F2a analogue), followed by a second 0.5 mg injection 24 hours later. Gilts are superovulated by injection of 1000 i.u. equine chorionic gonadotrophin (eCG) or pregnant mare serum gonadotrophin at the time of the second cloprostenol injection, and a subsequent injection 72 hours later of 500 i.u. human chorionic gonadotrophin (hCG).

c) Fertilization:

Superovulated gilts are artificially inseminated 20–30 hours after the hCG injection, followed by a second insemination 2–4 hours later, with semen from the boar that provided DNA for the targeting construct.

d) Embryo Collection:

Embryos are collected surgically 50–56 hours after hCG injection prior to fusion of the pronuclei. Oviducts are flushed with 15–20 ml phosphate saline buffer containing 1% fetal calf serum. One-cell embryos are recovered by searching oviductal flushings using low magnification microscopy.

III. Microinjection of Embryos

Embryos are centrifuged at 12000×g for 8 min to stratify the cytoplasm and allow the pronuclei to be visualised, and held in Dulbecco's Minimal Essential Medium with 25 mM Hepes and 5 mg/ml bovine serum albumin. Pronuclei are injected, using differential interference contrast optics, with 4–10 picolitres of DNA (10 ng/μl) in PBS. Gene targeting with isogenic DNA is maximized by coinjecting both allelic constructs derived from the boar into the male pronucleus.

IV. Transfer of Injected Embryos to Recipient Gilts

The oestrus cycles of recipient gilts are synchronized with those of donors. The recipients are mated and aborted using the protocol described above, and injected with 500 i.u. eCG. Injected embryos are transferred surgically (20–40 per oviduct) to recipients on the same day that they are collected from donor gilts.

V. Screening for Homologous Recombination

Homologous recombinants can be detected by analysis of tissue from the born piglets. Screening procedures involve PCR technology, the precise strategy depending on the design of the gene targeting construct. Because many α-1,3-Gal T mRNA molecules are synthesized from a single α-1,3-Gal T gene in expressing cells, the RT/PCR approach can be more sensitive than PCR amplification of genomic DNA. The RT/PCR screening strategy relies on successful transcription of the interrupted gene and relative stability of the shortened mRNA.

Alternatively, constructs that promote expression of heterologous genes (eg: GFP) in correctly targeted cells allow embryos to be screened at the blastocyst stage for marker gene expression (i.e.: GFP expression can be detected by measuring fluorescence within blastocysts at 509 nm). The microinjected embryos are cultured in vitro until blastocyst development, screened for fluorescence, and fluorescing embryos transferred into recipients.

EXAMPLE 17

A Novel Variant of Leukemia Inhibitory Factor (LIF)

Previous reports have demonstrated the existence of two forms of murine LIF. The original form (from the D transcript) was expressed and commercialized by AMRAD Corporation Ltd (Kew Victoria, Australia). The protein product derived from this transcript (hereinafter "D-LIF") is sold commercially by AMRAD as "ESGRO™". Another form of LIF (hereinafter "M-LIF"), derived from an alternative transcript, is described in U.S. patent application Ser. No. 07/994,099 and in Rathjen et al., Cell 62: 1105–14 (1990). The present inventors have now found a third transcript of LIF (hereinafter "D-LIF") which is found in ES cells and in human teratocarcinoma-derived cell lines such as the GCT 27 teratocarcinoma-derived cell lines described by Pera et al., Differentiation 42: 10 (1989).

The T-LIF protein is found intracellularly in contrast to the other two forms of LIF which are both extracellular. The transcript was cloned using the RACE PCR technique (see below) from murine ES cells and human GCT 27 teratocarcinoma-derived cell lines, and sequenced using standard methods. The presence of the T-LIF transcript was confirmed by PCR analysis of ES cell mRNA and RNA' ase protection on GCT 27 RNA. The transcript comprises a novel first exon, located in the first intron of the LIF gene, spliced to the known exon 2 and exon 3 sequences. The mouse nucleotide sequence (SEQ ID NO: 25) and deduced amino acid sequence (SEQ ID NO: 26) are set out in FIG. 26. The human nucleotide sequence (SEQ ID NO: 31) and deduced amino acid sequence (SEQ ID NO: 32) are set out in FIG. 27.

Figure 28:
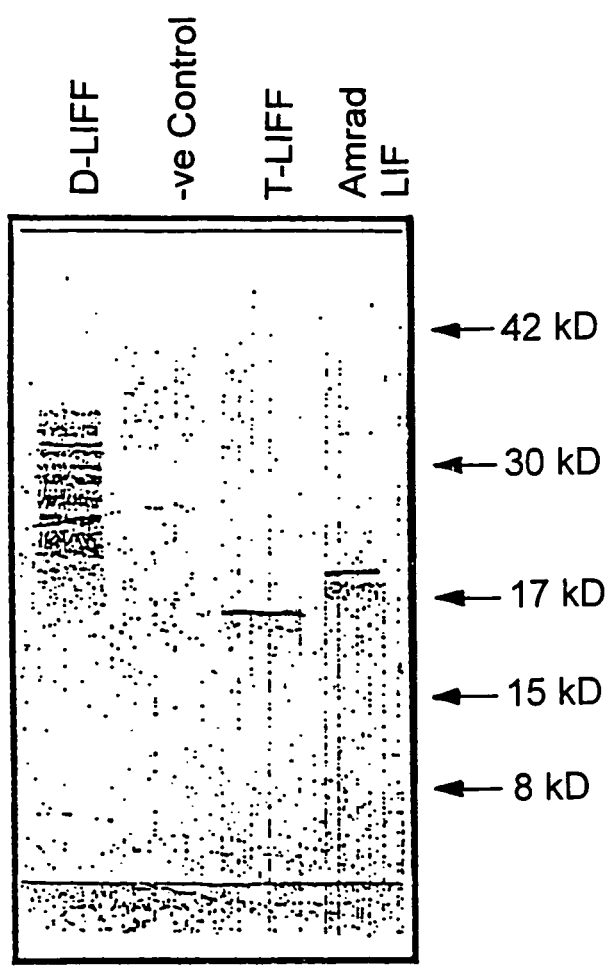
FIG. 28 is a Western blot of LIF polypeptides expressed from transfected COS cells.

When expressed in a COS cell expression system, the murine T-LIF transcript produces a 17 kD protein that is unglycosylated (D-LIF is glycosylated in the Golgi during the secretion process) (FIG. 28). Translation of T-LIF initiates at the first in-frame initiation codon (ATG) in exon 2 to produce a protein of 158 amino acids. The protein is 45 amino acids shorter than the unprocessed D-LIF protein and 22 amino acids shorter than the mature D-LIF product generated by cleavage of the signal sequence. Because the T-LIF protein does not contain a signal sequence, it does not leave the cell and is unglycosylated. The T form of LIF is efficacious in preventing the differentiation of ES cells in culture.

Methods

Race cDNA Cloning

Cytoplasmic RNA (10 μg) from CP1 murine ES cells (Bradley et al., Nature 309: 255–56 (1984) was reverse transcribed from the oligonucleotide 5' ACACGGTACT-TGTTGCA-3' (SEQ ID NO: 27), which hybridizes to residues 500–484 of the murine LIF cDNA. The RNA was added to 20 pmol of primer and 2 µl of 10×annealing buffer (500 mM Tris-HCl. (pH 8.0), 60 mM $MgCl_2$, 400 mM KCl) in a total volume of 16 µl, heated to 85° C. for 0.5 min, and cooled slowly to room temperature. The elongation reaction was carried out as described by Frohman et al. (Proc. Natl. Acad. Sci. USA 85: 8998–9002 (~1988)). Excess oligonucleotide was removed by gel filtration through a 2 ml Sephacryl S-400 (Pharmacia) column equilibrated with 0.05×TE (TE=10 mM Tris-HCl pH 7.6, 1.0 mM EDTA). Fractions of 5011 corresponding to the cDNA radioactive peak were pooled, concentrated by vacuum centrifugation, and resuspended in 23 µl of $H_2O$. To tail the 3'-end of the cDNA with dG residues, 3 µl of 10 mM dGTP and 6 µl of 5×tailing buffer (Bethesda Research Laboratories) were added and the mixture was incubated at 37° C. for 60 min. and then at 70° C. for 15 min. After ethanol precipitation, the cDNA template was resuspended in 500 µl $H_2O$.

PCR was carried out using a mouse LIF specific oligonucleotide, 5'-TTCTGGTCCCGGGTGATATTGGTCA-3' (residues 389–365) (SEQ ID NO: 28), and an anchor oligonucleotide, 5'-CCATGGCCTCGAGGGC-CCCCCCCCCCCCC-3' (SEQ ID NO: 29). PCR was carried out in a final volume of 50 µl containing 7 µl of the cDNA template and 34 pmol of each oligonucleotide. Reaction conditions were as recommended by Perkin-Elmer Cetus, with a final concentration of 1.5 mM $MgCl_2$. DNA was denatured prior to the addition of Taq polymerase (Perkin-Elmer Cetus) by heating the reaction mixture to 94° C. for 5 min. Each PCR cycle (35 in total) consisted of denaturation for 2 min at 94° C., annealing for 2 min at 55° C., and elongation for 3 min at 72° C. After the final elongation (30 min at 72° C.), samples were ethanol precipitated, digested with SmaI and XhoI and analyzed by agarose gel electrophoresis. DNA was purified from agarose gels using Geneclean and cloned into SalI- and SmaI-digested TST7 19U (Stratagene). Suitable recombinant plasmids were purified by the rapid boiling method.

Double-stranded sequencing was performed with Sequenase version 2.0 (USB) according to the manufacturers recommendations.

Biological Assay for LIF Activity

An undifferentiated, murine ES cell culture (MBL5; Pease et al., Dev. Biol. 141: 344–52 (1990), between passages 15 and 30) is trypsinized and made into a single cell suspension. The cells are pelleted by centrifugation and resuspended in complete ES Cell Medium without LIF (DMEM (without Hepes), 10% FCS, 1 mM βME, 1 mM glutamine). The cells are then seeded into 24-well microtitre plates at $5 \times 10^2$ cells/16 mm well containing 1 ml of ES Cell Medium without LIF.

Figure 29:
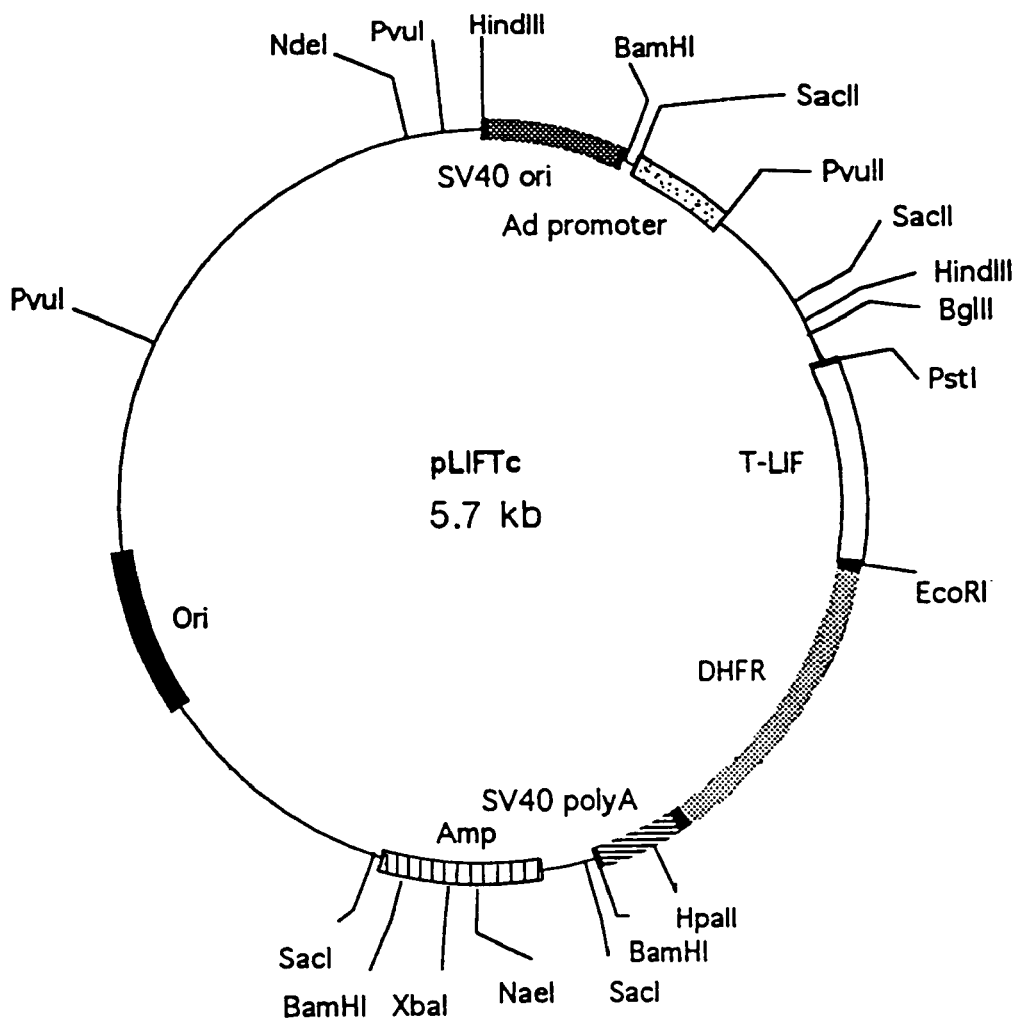
FIG. 29 is a diagram of the expression plasmid used for transfection of the COS cells of FIG. 27.

The complete T-LIF open reading frame was reconstructed from the PCR product and inserted into the COS cell expression vector pXMT2 as described by Rathjen et al., Cell 62: 1105–14 (1990). The plasmid used for transfection of COS cells is shown in FIG. 29. The COS cells were transfected by electroporation. Supernatants from COS cells expressing T-LIF were added to the above ES cells in various dilutions (1/5, 1/10, 1/50, 1/100, 1/50, 1/1000) and incubated for 4 days in an incubator with 10% $CO_2$. Controls used supernatants from COS cells expressing D-LIF (pDR1, Rathjen et al., Cell 62: 1105–14 (1990)).

LIF activity is assessed as present if cells morphologically resemble ES-cells after 4 days and are distinct from the controls incubated without any form of LIF. The ES-cells are also stained for alkaline phosphatase as undifferentiated ES-cells are positive for this marker.

Even though T-LIF is produced intracellularly, sufficient numbers of cells lyse to give significant amounts of LIF activity in the culture supernatants. If the COS cells expressing T-LIF are lysed, more LIF activity is released.

PCR Detection of T-LIF Transcript

Figure 30:
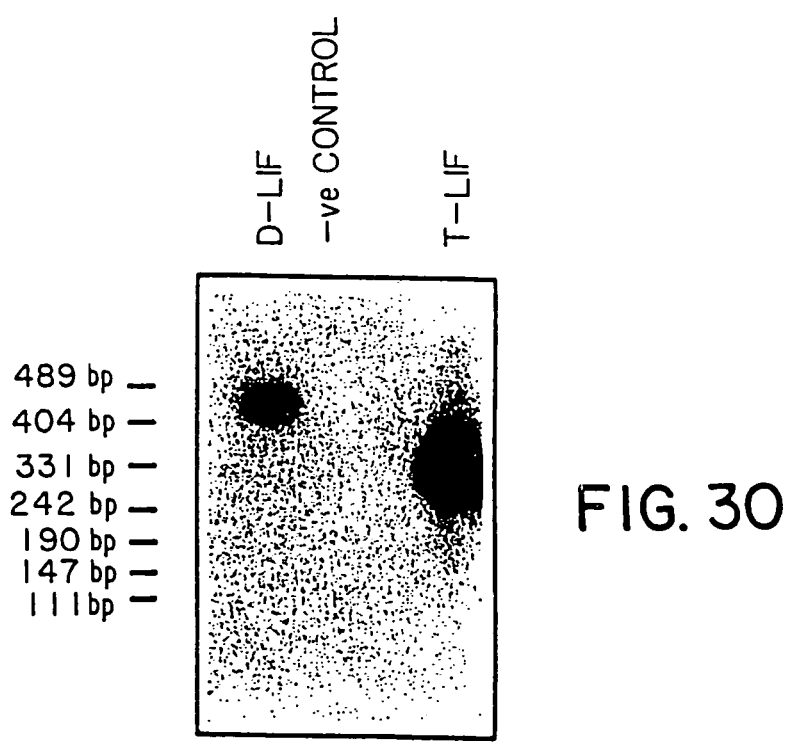
FIG. 30 is a Southern blot of PCR-amplified cDNA from murine ES cells, using a LIF-specific probe.

PCR was carried but on ES cell cDNA (prepared as described above except that the cDNA was not tailed with dG). PCR conditions were as described above except that 2 mM $MgCl_2$ was used in the reactions. The oligonucleotides 5'-CACCTTTCGCTTTCCT-3' (SEQ. ID NO. 30) and 5'-TTCTGGTCCCGGGTGATATTGGTCA-3' (SEQ. ID. NO 28) were used at 80 picograms/reaction. Products of the PCR reaction were ethanol precipitated as described above, separated electrophoretically on a 2% agarose gel and transferred to a nylon membrane for detection using Southern hybridization (FIG. 30). The probe was the full length D-LIF transcript isolated from pDR1 (Rathjen et al., Cell 62: 1105–14 (1990). The control experiment is designed to detect all LIF transcripts using internal primers 5'-TTCTG-GTCCCGGGTGATATTGGTCA-3' (SEQ. ID. NO 28) and 5'-CTGTTGGTTCTGCACTGGA-3' (SEQ. ID. NO. 33).

The foregoing detailed description has been provided for a better understanding of the invention only and no unnecessary limitation should be understood therefrom as some modifications will be apparent to those skilled the art without deviating from the spirit and scope of the appended claims.

We claim:

1. A method for generating a porcine cell comprising at least one inactivated α-1,3 galactosyltransferase gene, the method comprising:
   (a) providing a plurality of porcine cells;
   (b) introducing, in vitro, into said cells a DNA construct comprising a disrupted porcine α-1,3 galactosyltransferase gene, wherein the disruption is by insertion of an exogenous sequence into said gene such that disruption prevents expression of functional α-1,3 galactosyltransferase, wherein the gene, prior to disruption, encodes a porcine α-1,3 galactosyltransferase with the amino acid sequence of SEQ ID NO:10;
   (c) incubating said cells such that homologous recombination occurs between the chromosomal sequence encoding α-1,3 galactosyltransferase and the introduced DNA construct comprising the disrupted α-1,3 galactosyltransferase gene; and
   (d) identifying a porcine cell comprising at least one inactivated α-1,3 galactosyltransferase gene,
   wherein the gene, prior to disruption, encodes a porcine α-1,3 galactosyltransferase with the amino acid sequence of SEQ ID NO:10.

2. The method of claim 1, wherein said disruption is within exon 4, exon 7, exon 8, or exon 9 of the porcine α-1,3 galactosyltransferase gene.

3. The method of claim 1, wherein said exogenous sequence is a selectable marker.

4. The method of claim 3, wherein said selectable marker is selected from the group consisting of the neo$^R$ gene and the hyg$^R$ gene.

5. The method of claim 1, wherein said exogenous sequence is flanked at its 5' and 3' ends by FRT DNA elements, and wherein stop codons have been inserted 3' to the selectable marker for each of the three reading frames for the porcine α-1,3 galactosyltransferase gene.

6. A porcine cell comprising at least one disrupted α-1,3 galactosyltransferase gene, wherein the disruption is by insertion of an exogenous sequence into said gene such that the disruption prevents expression of functional α-1,3 galactosyltransferase and wherein the gene, prior to disruption, encodes the porcine α-1,3 galactosyltransferase with the amino acid sequence of SEQ ID NO:10, wherein the cell is in vitro.

7. The porcine cell of claim 6, wherein said disruption is within exon 4, exon 7, exon 8, or exon 9 of the porcine α-1,3 galactosyltransferase gene.

8. The porcine cell of claim 6, wherein said exogenous sequence is a selectable marker.

9. The porcine cell of claim 8, wherein said selectable marker is selected from the group consisting of the neo$^R$ gene and the hyg$^R$ gene.

10. The porcine cell of claim 6, wherein said exogenous sequence is flanked at its 5' and 3' ends by FRT DNA elements, and wherein stop codons have been inserted 3' to the selectable marker for each of the three reading frames for the porcine α-1,3 galactosyltransferase gene.

* * * * *

SEQUENCE LISTING (1) GENERAL INFORMATION:

(iii) NUMBER OF SEQUENCES: 33

(2) INFORMATION FOR SEQ ID NO: 1:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

GTGAATTCAG CCCTGCCTCC TTCTGCAG                                    28

(2) INFORMATION FOR SEQ ID NO: 2:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

GTGAATTCAG GAGAAAATAA TGAATGTC                                    28

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

GTGAATTCGG GATCTGCCTT GTACCACC                                    28

(2) INFORMATION FOR SEQ ID NO: 4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

GTGAATTCGA AATCACTGGG AATTTACA                                    28

(2) INFORMATION FOR SEQ ID NO: 5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

AGGAATTCAG CATGATGCGC ATGAAGAC                                    28

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

TTTGAATTCT TTTTTTTTTT TVN                                         23

(2) INFORMATION FOR SEQ ID NO: 7:

(i) SEQUENCE CHARACTERISTICS:
        (A) LENGTH: 1412 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

```
AGCCCTGCCT CCTTCTGCAG AGCAGAGCTC ACTAGAACTT GTTTCGCCTT TTACTCTGGG          60

GGGAGAGAAG CAGAGGATGA GGAGAAAATA ATG AAT GTC AAA GGA AGA GTG GTT          114
                                 Met Asn Val Lys Gly Arg Val Val
                                  1               5

CTG TCA ATG CTG CTT GTC TCA ACT GTA ATG GTT GTG TTT TGG GAA TAC          162
Leu Ser Met Leu Leu Val Ser Thr Val Met Val Val Phe Trp Glu Tyr
         10                  15                  20

ATC AAC AGC CCA GAA GGT TCT TTG TTC TGG ATA TAC CAG TCA AAA AAC          210
Ile Asn Ser Pro Glu Gly Ser Leu Phe Trp Ile Tyr Gln Ser Lys Asn
 25                  30                  35                  40

CCA GAA GTT GGC AGC AGT GCT CAG AGG GGC TGG TGG TTT CCG AGC TGG          258
Pro Glu Val Gly Ser Ser Ala Gln Arg Gly Trp Trp Phe Pro Ser Trp
                 45                  50                  55

TTT AAC AAT GGG ACT CAC AGT TAC CAC GAA GAA GAA GAC GCT ATA GGC          306
Phe Asn Asn Gly Thr His Ser Tyr His Glu Glu Glu Asp Ala Ile Gly
             60                  65                  70

AAC GAA AAG GAA CAA AGA AAA GAA GAC AAC AGA GGA GAG CTT CCG CTA          354
Asn Glu Lys Glu Gln Arg Lys Glu Asp Asn Arg Gly Glu Leu Pro Leu
         75                  80                  85

GTG GAC TGG TTT AAT CCT GAG AAA CGC CCA GAG GTC GTG ACC ATA ACC          402
Val Asp Trp Phe Asn Pro Glu Lys Arg Pro Glu Val Val Thr Ile Thr
     90                  95                 100

AGA TGG AAG GCT CCA GTG GTA TGG GAA GGC ACT TAC AAC AGA GCC GTC          450
Arg Trp Lys Ala Pro Val Val Trp Glu Gly Thr Tyr Asn Arg Ala Val
105                 110                 115                 120

TTA GAT AAT TAT TAT GCC AAA CAG AAA ATT ACC GTG GGC TTG ACG GTT          498
Leu Asp Asn Tyr Tyr Ala Lys Gln Lys Ile Thr Val Gly Leu Thr Val
                125                 130                 135

TTT GCT GTC GGA AGA TAC ATT GAG CAT TAC TTG GAG GAG TTC TTA ATA          546
Phe Ala Val Gly Arg Tyr Ile Glu His Tyr Leu Glu Glu Phe Leu Ile
            140                 145                 150

TCT GCA AAT ACA TAC TTC ATG GTT GGC CAC AAA GTC ATC TTT TAC ATC          594
Ser Ala Asn Thr Tyr Phe Met Val Gly His Lys Val Ile Phe Tyr Ile
        155                 160                 165

ATG GTG GAT GAT ATC TCC AGG ATG CCT TTG ATA GAG CTG GGT CCT CTG          642
Met Val Asp Asp Ile Ser Arg Met Pro Leu Ile Glu Leu Gly Pro Leu
    170                 175                 180

CGT TCC TTT AAA GTG TTT GAG ATC AAG TCC GAG AAG AGG TGG CAA GAC          690
Arg Ser Phe Lys Val Phe Glu Ile Lys Ser Glu Lys Arg Trp Gln Asp
185                 190                 195                 200

ATC AGC ATG ATG CGC ATG AAG ACC ATC GGG GAG CAC ATC CTG GCC CAC          738
Ile Ser Met Met Arg Met Lys Thr Ile Gly Glu His Ile Leu Ala His
                205                 210                 215

ATC CAG CAC GAG GTG GAC TTC CTC TTC TGC ATG GAC GTG GAT CAG GTC          786
Ile Gln His Glu Val Asp Phe Leu Phe Cys Met Asp Val Asp Gln Val
            220                 225                 230

TTC CAA AAC AAC TTT GGG GTG GAG ACC CTG GGC CAG TCG GTG GCT CAG          834
Phe Gln Asn Asn Phe Gly Val Glu Thr Leu Gly Gln Ser Val Ala Gln
        235                 240                 245
```

```
CTA CAG GCC TGG TGG TAC AAG GCA CAT CCT GAC GAG TTC ACC TAC GAG      882
Leu Gln Ala Trp Trp Tyr Lys Ala His Pro Asp Glu Phe Thr Tyr Glu
    250                 255                 260

AGG CGG AAG GAG TCC GCA GCC TAC ATT CCG TTT GGC CAG GGG GAT TTT      930
Arg Arg Lys Glu Ser Ala Ala Tyr Ile Pro Phe Gly Gln Gly Asp Phe
265                 270                 275                 280

TAT TAC CAC GCA GCC ATT TTT GGG GGA ACA CCC ACT CAG GTT CTA AAC      978
Tyr Tyr His Ala Ala Ile Phe Gly Gly Thr Pro Thr Gln Val Leu Asn
                285                 290                 295

ATC ACT CAG GAG TGC TTC AAG GGA ATC CTC CAG GAC AAG GAA AAT GAC     1026
Ile Thr Gln Glu Cys Phe Lys Gly Ile Leu Gln Asp Lys Glu Asn Asp
            300                 305                 310

ATA GAA GCC GAG TGG CAT GAT GAA AGC CAT CTA AAC AAG TAT TTC CTT     1074
Ile Glu Ala Glu Trp His Asp Glu Ser His Leu Asn Lys Tyr Phe Leu
        315                 320                 325

CTC AAC AAA CCC ACT AAA ATC TTA TCC CCA GAA TAC TGC TGG GAT TAT     1122
Leu Asn Lys Pro Thr Lys Ile Leu Ser Pro Glu Tyr Cys Trp Asp Tyr
    330                 335                 340

CAT ATA GGC ATG TCT GTG GAT ATT AGG ATT GTC AAG ATA GCT TGG CAG     1170
His Ile Gly Met Ser Val Asp Ile Arg Ile Val Lys Ile Ala Trp Gln
345                 350                 355                 360

AAA AAA GAG TAT AAT TTG GTT AGA AAT AAC ATC T GACTTTAAAT            1214
Lys Lys Glu Tyr Asn Leu Val Arg Asn Asn Ile
                365                 370

TGTGCCAGCA GTTTTCTGAA TTTGAAAGAG TATTACTCTG CTACTTCCT CAGAGAAGTA    1274

GCACTTAATT TTAACTTTTA AAAAAATACT AACAAAATAC CAACACAGTA AGTACATATT   1334

ATTCTTCCTT GCAACTTTGA GCCTTGTCAA ATGGGAGAAT GACTCTGTGG TAATCAGATG   1394

TAAATTCCCA GTGATTTC                                                 1412

(2) INFORMATION FOR SEQ ID NO: 8:

(i) SEQUENCE CHARACTERISTICS:
        (A) LENGTH: 1828 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

CCGGGGGCCG GGCCGAGCTG GGAGCGTCGA GCCCGCTGCC CAGCGCCCGC CGGCTCCCTC      60

GCGCCCCTGC CCGCCGCCCC GGAGGAGCGC CCGGCGGCCG GCCGACGGGA GCGCAGCGGC     120

ACACCCCGCC CCGGCACGCC CGCGGGGCTC GGGAGGAGGC AGCGCGCCGA CTGTTCCGGC     180

AGCCGAGGAC GCCGCCGGGG AGCCGAGGCG CCGGCCAGCC CCCAGCGCGC CCAGCTTCTG     240

CGGATCAGGG AAACCACGTG TCCTCAAGTG GCCAGCCAGC TGTCCCCAAG AGGAACTTGC     300

CTGGCATTTG CACGGAAAGA CGAGACACTT CACAAAATCA ACGGAGTCAG AAGGCTGCAC     360

CTTCGCTTCC TCCCAGCCCT GCCTCCTTCT GCAGAACGGA GCTCAGTAGA ACTTGGTACT     420

TTTGCCTTTT ACTCTAGGAG GAGAGAAGCA GACGATGAGG AGAAAATA ATG AAT GTC     477
                                                     Met Asn Val

AAA GGA AAA GTG ATT CTG TCA ATG CTG GTT GTC TCA ACT GTC ATT GTT      525
Lys Gly Lys Val Ile Leu Ser Met Leu Val Val Ser Thr Val Ile Val
    5                   10                  15

GTG TTT TGG GAA TAT ATC CAC AGC CCA GAA GGC TCT TTG TTC TGG ATA      573
Val Phe Trp Glu Tyr Ile His Ser Pro Glu Gly Ser Leu Phe Trp Ile
20                  25                  30                  35

AAC CCA TCA AGA AAC CCA GAA GTT GGT GGC AGC AGC ATT CAG AAG GGC      621
```

-continued

```
Asn Pro Ser Arg Asn Pro Glu Val Gly Gly Ser Ser Ile Gln Lys Gly
             40                  45                  50

TGG TGG CTT CCG AGA TGG TTT AAC AAT GGT TAC CAT GAA GAA GAT GGA        669
Trp Trp Leu Pro Arg Trp Phe Asn Asn Gly Tyr His Glu Glu Asp Gly
             55                  60                  65

GAC ATA AAC GAA GAA AAG GAA CAA AGA AAC GAA GAC GAA AGC AAG CTT        717
Asp Ile Asn Glu Glu Lys Glu Gln Arg Asn Glu Asp Glu Ser Lys Leu
         70                  75                  80

AAG CTA TCG GAC TGG TTC AAC CCA TTT AAA CGC CCC GAG GTT GTG ACC        765
Lys Leu Ser Asp Trp Phe Asn Pro Phe Lys Arg Pro Glu Val Val Thr
             85                  90                  95

ATG ACG AAG TGG AAG GCT CCA GTG GTG TGG GAA GGC ACT TAC AAC AGA        813
Met Thr Lys Trp Lys Ala Pro Val Val Trp Glu Gly Thr Tyr Asn Arg
100             105                 110                 115

GCC GTC TTA GAC AAT TAT TAT GCC AAG CAG AAA ATT ACC GTC GGC CTG        861
Ala Val Leu Asp Asn Tyr Tyr Ala Lys Gln Lys Ile Thr Val Gly Leu
                120                 125                 130

ACG GTT TTC GCC GTC GGA AGA TAC ATT GAG CAT TAC TTG GAG GAG TTC        909
Thr Val Phe Ala Val Gly Arg Tyr Ile Glu His Tyr Leu Glu Glu Phe
             135                 140                 145

TTA ACG TCT GCT AAT AAG CAC TTC ATG GTG GGC CAC CCA GTC ATC TTT        957
Leu Thr Ser Ala Asn Lys His Phe Met Val Gly His Pro Val Ile Phe
         150                 155                 160

TAT ATC ATG GTA GAT GAT GTC TCC AGG ATG CCT TTG ATA GAG TTG GGT       1005
Tyr Ile Met Val Asp Asp Val Ser Arg Met Pro Leu Ile Glu Leu Gly
         165                 170                 175

CCT CTG CGC TCC TTC AAA GTG TTT AAG ATC AAG CCT GAG AAG AGG TGG       1053
Pro Leu Arg Ser Phe Lys Val Phe Lys Ile Lys Pro Glu Lys Arg Trp
180             185                 190                 195

CAG GAC ATC AGC ATG ATG CGC ATG AAG ACT ATC GGG GAG CAC ATT GTG       1101
Gln Asp Ile Ser Met Met Arg Met Lys Thr Ile Gly Glu His Ile Val
                 200                 205                 210

GCC CAC ATC CAG CAT GAG GTT GAC TTC CTT TTC TGC ATG GAT GTG GAC       1149
Ala His Ile Gln His Glu Val Asp Phe Leu Phe Cys Met Asp Val Asp
             215                 220                 225

CAG GTC TTC CAA GAC AAG TTT GGG GTG GAG ACC CTG GGC GAG TCG GTG       1197
Gln Val Phe Gln Asp Lys Phe Gly Val Glu Thr Leu Gly Glu Ser Val
         230                 235                 240

GCC CAG CTA CAA GCC TGG TGG TAC AAG GCA GAT CCC AAT GAC TTC ACC       1245
Ala Gln Leu Gln Ala Trp Trp Tyr Lys Ala Asp Pro Asn Asp Phe Thr
     245                 250                 255

TAC GAG AGG CGG AAG GAG TCT GCA GCA TAC ATT CCC TTC GGC GAA GGG       1293
Tyr Glu Arg Arg Lys Glu Ser Ala Ala Tyr Ile Pro Phe Gly Glu Gly
260             265                 270                 275

GAT TTT TAT TAC CAT GCA GCC ATT TTT GGG GGA ACA CCC ACT CAG GTC       1341
Asp Phe Tyr Tyr His Ala Ala Ile Phe Gly Gly Thr Pro Thr Gln Val
                 280                 285                 290

CTT AAC ATC ACC CAG GAA TGC TTC AAA GGA ATC CTC AAG GAC AAG AAA       1389
Leu Asn Ile Thr Gln Glu Cys Phe Lys Gly Ile Leu Lys Asp Lys Lys
             295                 300                 305

AAT GAC ATA GAA GCC CAA TGG CAT GAT GAA AGC CAT CTA AAC AAG TAT       1437
Asn Asp Ile Glu Ala Gln Trp His Asp Glu Ser His Leu Asn Lys Tyr
         310                 315                 320

TTC CTT CTC AAC AAA CCT ACT AAA ATC TTA TCC CCG GAA TAC TGC TGG       1485
Phe Leu Leu Asn Lys Pro Thr Lys Ile Leu Ser Pro Glu Tyr Cys Trp
     325                 330                 335

GAT TAT CAC ATA GGC CTA CCT GCG GAT ATT AAG CTT GTC AAG ATG TCT       1533
Asp Tyr His Ile Gly Leu Pro Ala Asp Ile Lys Leu Val Lys Met Ser
340             345                 350                 355
```

```
TGG CAG ACA AAA GAG TAT AAT GTG GTT AGA AAT AAT GTC T GACTTTGTGC         1583
Trp Gln Thr Lys Glu Tyr Asn Val Val Arg Asn Asn Val
                360                 365

CAGTACATTT CTGAATTTGA GAGAGTATTA TTCTGGCTAC TTCCTCAGAA AAGTAACACT        1643

TAATTTTAAC TTAAAAAAAA ATACTAACAA AAGACCAACA CAGCAAATAC ATATTATTTC        1703

TCCTTGTAAC TTTGAGCCTT GTAATACGGG AGAATGAACC TGTGGTAATC AGATGTAAAT        1763

TCCCAGTGAT TTCTTACCTA TTTTTGGTTG TGGGGGCGGG GAATGGATAC ACCATCAGTT        1823

GAACC                                                                    1828

(2) INFORMATION FOR SEQ ID NO: 9:

(i) SEQUENCE CHARACTERISTICS:
        (A) LENGTH: 3450 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

CGTCTTAGGA GGCTGGAGAT TCTGGGTGGA GCCCTAGCCC TGCCTTTTCT TAGCTGGCTG          60

ACACCTTCCC TTGTAGACTC TTCTTGGAAT GAGAAGTACC GATTCTGCTG AAGACCTCGC         120

GCTCTCAGGC TCTGGGAGTT GGAACCCTCG TACCTTCCTT TCCTCTGCTG AGCCCTGCCT         180

CCTTCGGCAG GCCAGAGCTG ACAGAAGCTC GGTTGCTTTG CTGTTTGCTT TGGAGGGAAC         240

ACAGCTGACG ATGAGGCTGA CTTTGAACTC AAGAGATCTG CTTACCCCAG TCTCCTGGAA         300

TTAAAGGCCT GTACTACCTT GCCTGGACCT AAGATTTTCA TGATCACTAT GCTTCAAGAT         360

CTCCATGTCA ACAAGATCTC CATGTCAAGA TCCAAGTCAG AAACAAGTCT TCCATCCTCA         420

AGATCTGGAT CACAGGAGAA AATA ATG AAT GTC AAG GGA AAA GTA ATC CTG           471
                          Met Asn Val Lys Gly Lys Val Ile Leu
                           1               5

TTG ATG CTG ATT GTC TCA ACC GTG GTT GTC GTG TTT TGG GAA TAT GTC          519
Leu Met Leu Ile Val Ser Thr Val Val Val Val Phe Trp Glu Tyr Val
 10              15                  20                  25

AAC AGC CCA GAC GGC TCT TTC TTG TGG ATA TAT CAC ACA AAA ATT CCA          567
Asn Ser Pro Asp Gly Ser Phe Leu Trp Ile Tyr His Thr Lys Ile Pro
             30                  35                  40

GAG GTT GGT GAG AAC AGA TGG CAG AAG GAC TGG TGG TTC CCA AGC TGG          615
Glu Val Gly Glu Asn Arg Trp Gln Lys Asp Trp Trp Phe Pro Ser Trp
         45                  50                  55

TTT AAA AAT GGG ACC CAC AGT TAT CAA GAA GAC AAC GTA GAA GGA CGG          663
Phe Lys Asn Gly Thr His Ser Tyr Gln Glu Asp Asn Val Glu Gly Arg
     60                  65                  70

AGA GAA AAG GGT AGA AAT GGA GAT CGC ATT GAA GAG CCT CAG CTA TGG          711
Arg Glu Lys Gly Arg Asn Gly Asp Arg Ile Glu Glu Pro Gln Leu Trp
 75                  80                  85

GAC TGG TTC AAT CCA AAG AAC CGC CCG GAT GTT TTG ACA GTG ACC CCG          759
Asp Trp Phe Asn Pro Lys Asn Arg Pro Asp Val Leu Thr Val Thr Pro
         90                  95                 100                 105

TGG AAG GCG CCG ATT GTG TGG GAA GGC ACT TAT GAC ACA GCT CTG CTG          807
Trp Lys Ala Pro Ile Val Trp Glu Gly Thr Tyr Asp Thr Ala Leu Leu
                110                 115                 120

GAA AAG TAC TAC GCC ACA CAG AAA CTC ACT GTG GGG CTG ACA GTG TTT          855
Glu Lys Tyr Tyr Ala Thr Gln Lys Leu Thr Val Gly Leu Thr Val Phe
            125                 130                 135

GCT GTG GGA AAG TAC ATT GAG CAT TAC TTA GAA GAC TTT CTG GAG TCT          903
Ala Val Gly Lys Tyr Ile Glu His Tyr Leu Glu Asp Phe Leu Glu Ser
```

```
                140             145             150
GCT GAC ATG TAC TTC ATG GTT GGC CAT CGG GTC ATA TTT TAC GTC ATG        951
Ala Asp Met Tyr Phe Met Val Gly His Arg Val Ile Phe Tyr Val Met
        155             160             165

ATA GAT GAC ACC TCC CGG ATG CCT GTC GTG CAC CTG AAC CCT CTA CAT        999
Ile Asp Asp Thr Ser Arg Met Pro Val Val His Leu Asn Pro Leu His
170             175             180                         185

TCC TTA CAA GTC TTT GAG ATC AGG TCT GAG AAG AGG TGG CAG GAT ATC       1047
Ser Leu Gln Val Phe Glu Ile Arg Ser Glu Lys Arg Trp Gln Asp Ile
            190             195                         200

AGC ATG ATG CGC ATG AAG ACC ATT GGG GAG CAC ATC CTG GCC CAC ATC       1095
Ser Met Met Arg Met Lys Thr Ile Gly Glu His Ile Leu Ala His Ile
        205             210                         215

CAG CAC GAG GTC GAC TTC CTC TTC TGC ATG GAC GTG GAT CAA GTC TTT       1143
Gln His Glu Val Asp Phe Leu Phe Cys Met Asp Val Asp Gln Val Phe
        220             225             230

CAA GAC AAC TTC GGG GTG GAA ACT CTG GGC CAG CTG GTA GCA CAG CTC       1191
Gln Asp Asn Phe Gly Val Glu Thr Leu Gly Gln Leu Val Ala Gln Leu
    235             240             245

CAG GCC TGG TGG TAC AAG GCC AGT CCC GAG AAG TTC ACC TAT GAG AGG       1239
Gln Ala Trp Trp Tyr Lys Ala Ser Pro Glu Lys Phe Thr Tyr Glu Arg
250             255             260             265

CGG GAA CTG TCG GCC GCG TAC ATT CCA TTC GGA GAG GGG GAT TTT TAC       1287
Arg Glu Leu Ser Ala Ala Tyr Ile Pro Phe Gly Glu Gly Asp Phe Tyr
            270             275             280

TAC CAC GCG GCC ATT TTT GGA GGA ACG CCT ACT CAC ATT CTC AAC CTC       1335
Tyr His Ala Ala Ile Phe Gly Gly Thr Pro Thr His Ile Leu Asn Leu
        285             290             295

ACC AGG GAG TGC TTT AAG GGG ATC CTC CAG GAC AAG AAA CAT GAC ATA       1383
Thr Arg Glu Cys Phe Lys Gly Ile Leu Gln Asp Lys Lys His Asp Ile
        300             305             310

GAA GCC CAG TGG CAT GAT GAG AGC CAC CTC AAC AAA TAC TTC CTT TTC       1431
Glu Ala Gln Trp His Asp Glu Ser His Leu Asn Lys Tyr Phe Leu Phe
        315             320             325

AAC AAA CCC ACT AAA ATC CTA TCT CCA GAG TAT TGC TGG GAC TAT CAG       1479
Asn Lys Pro Thr Lys Ile Leu Ser Pro Glu Tyr Cys Trp Asp Tyr Gln
330             335             340             345

ATA GGC CTG CCT TCA GAT ATT AAA AGT GTC AAG GTA GCT TGG CAG ACA       1527
Ile Gly Leu Pro Ser Asp Ile Lys Ser Val Lys Val Ala Trp Gln Thr
            350             355             360

AAA GAG TAT AAT TTG GTT AGA AAT AAT GTC T GACTTCAAAT TGTGATGGAA       1578
Lys Glu Tyr Asn Leu Val Arg Asn Asn Val
        365             370

ACTTGACACT ATTACTCTGG CTAATTCCTC AAACAAGTAG CAACACTTGA TTTCAACTTT     1638

TAAAAGAAAC AATCAAAACC AAAACCCACT ACCATGGCAA ACAGATGATT CTCCTGACA      1698

CCTTGAGCCT GTAATATGTG AGAAAGAGTC TATGGCAAGT AATCAGGTAT AAATTCTCAA     1758

TGATTTCTTA TATATTCTGG GTCTTGGGAA AACTTGATTC TAGAAATCAA AATTAATTTG     1818

ACAAAGGAAA AGCAGATGCC GGAAACTTCT TCCCAGTCTG TCATACAATT CACCACTGGC     1878

CAGGTGCTGA GAGAAGCATT AGGGAACAGT GTGGGTTGTG TCAGAGTTGG ACGGCTCCAT     1938

CCCTTTGGCT TCATTATCTT CCTCCTCATG GAGATTCTAA AGCAACCCAG AGAGGCTTTG     1998

CAGCCAGAGA CCTTTAATAA GGATGCCAAT GTGACCATCA GTCTGTAAAA GCTGATGGCT     2058

CCAGGAGCGC TGGCAGTCCA GGCCCCACTA GGCTATTGTT TCTGTCCTGG GCATAAAGGA     2118

GGCAGAGAGT GCCAATAGGT ACTTTGGTGG CACATGTTCA GAGTCCAGGA AAAATCAAGG     2178

GTGACCACTT AGAGGGACAT AGGACTTGGG GTTGGTGATT GAACTGAGTT ACAAACACAG     2238
```

-continued

```
ACAGCTTTCT TCAGGATGAC TAACAGCAGG AATTGAATGG AAAGTGTGTT CATTTTGTTT    2298

TGCCCAAATT GTATTCATGC TGTTAGCTTT GTGTGTTGAG CCCTGTGGAG AGGGTGTGAC    2358

TGTATCAGGG AAGGAGAGTA CCTCAGCGGA CTGAGGACCA GCACCCTATT ATATCAGAAG    2418

ACAATCTCTC ATCATCAGGT CCTACCTACA ACCTGCTCTG AACCTCCGAG TTCCTCAGCC    2478

CATCGTGTTC CAGTGTGGGG GCCTGTATGG AGCAGGTGAC TGAAGACAAA GCCCCCTGTC    2538

ACATGACCTC ATTTCCCCTG CTCTAGTACT ATGCAAGTGT GACAGCCAGC CAGCCAGATG    2598

TACTGGACAA CATAGGAACC GACTTTATGG CAATGGGAGC CGCAGTCACT ACAACGGAGC    2658

TGCTGAAGGT TCTGTTCCCC GCTCTGAGAG CCTGCAGGAG CCCCTGTATA GGTGGTTCTC    2718

AACCTATGGG TCGCGACCCC TTTGGGAAGT GTTAAATGAC CCTTTCACAG GTGTCCCCTA    2778

AGACGGTTAA AAAACATAGA TATTTCCACT CTGACTGGTA ACAGTAGCAG AATTACAGTT    2838

ATGAAATAGC AAGGGAAATA ATTCTGGGGT TCGTGTCATC CATACCATGA GGAGCTACAT    2898

TAGGTCACAT CATTAGGGAA GTTGAGAAGC ATAGCTCTAC TTGGGTATTT AAGCAAATTA    2958

TGCAAAGGGG GTTGTCGCTC TGTGTTCTGT GTATGCATAT ATTTATATTT TGCTTGTCTT    3018

CCAGTTTAGG TCAATCTGTT TCTTCCTTTA AGCAGTTTAT TTAAAAGGCC ATTGCACCAT    3078

CTTGGTGAAC AGCATGAGGG GTTTCAATAA AAAATAGGAT CTTACCTTTG TCCACAGGGC    3138

TCTACCTCTT ACTTTTCAAT TGTGAACAAA AAAGGTCGCA CACCCAGAGG CAACAAAACC    3198

CACAGAATTC CTGAACCAAT GGGAGATGCC AATGGAAGCA GAGCTTGCAC ATCTGCTAAA    3258

AATTCTGCCT CTCTGTCACT GTGCTGGATC CGTCTAAAGT GGGACAGTTC AATGGTCTGA    3318

AAGTTTCAAA AAGGCTGGGG AATTTGAGGG GATTTTTTTT TAAAATAAAA TTGATCCAAG    3378

TTTAAATCTC TAATGAGTAA GCTTAGGATT TTATTAAAGG TAATTTTTAG ACATTCTTCA    3438

AAATAAGAAT TC                                                        3450
```

(2) INFORMATION FOR SEQ ID NO: 10:

(i) SEQUENCE CHARACTERISTICS:
        (A) LENGTH: 371 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Asn Val Lys Gly Arg Val Val Leu Ser Met Leu Leu Val Ser Thr
1               5                   10                  15

Val Met Val Val Phe Trp Glu Tyr Ile Asn Ser Pro Glu Gly Ser Leu
            20                  25                  30

Phe Trp Ile Tyr Gln Ser Lys Asn Pro Glu Val Gly Ser Ser Ala Gln
        35                  40                  45

Arg Gly Trp Trp Phe Pro Ser Trp Phe Asn Asn Gly Thr His Ser Tyr
    50                  55                  60

His Glu Glu Glu Asp Ala Ile Gly Asn Glu Lys Glu Gln Arg Lys Glu
65                  70                  75                  80

Asp Asn Arg Gly Glu Leu Pro Leu Val Asp Trp Phe Asn Pro Glu Lys
                85                  90                  95

Arg Pro Glu Val Val Thr Ile Thr Arg Trp Lys Ala Pro Val Val Trp
            100                 105                 110

Glu Gly Thr Tyr Asn Arg Ala Val Leu Asp Asn Tyr Tyr Ala Lys Gln
        115                 120                 125
```

```
Lys Ile Thr Val Gly Leu Thr Val Phe Ala Val Gly Arg Tyr Ile Glu
            130                 135                 140
His Tyr Leu Glu Glu Phe Leu Ile Ser Ala Asn Thr Tyr Phe Met Val
145                 150                 155                 160
Gly His Lys Val Ile Phe Tyr Ile Met Val Asp Asp Ile Ser Arg Met
                165                 170                 175
Pro Leu Ile Glu Leu Gly Pro Leu Arg Ser Phe Lys Val Phe Glu Ile
            180                 185                 190
Lys Ser Glu Lys Arg Trp Gln Asp Ile Ser Met Met Arg Met Lys Thr
        195                 200                 205
Ile Gly Glu His Ile Leu Ala His Ile Gln His Glu Val Asp Phe Leu
    210                 215                 220
Phe Cys Met Asp Val Asp Gln Val Phe Gln Asn Asn Phe Gly Val Glu
225                 230                 235                 240
Thr Leu Gly Gln Ser Val Ala Gln Leu Gln Ala Trp Trp Tyr Lys Ala
                245                 250                 255
His Pro Asp Glu Phe Thr Tyr Glu Arg Arg Lys Glu Ser Ala Ala Tyr
            260                 265                 270
Ile Pro Phe Gly Gln Gly Asp Phe Tyr Tyr His Ala Ala Ile Phe Gly
        275                 280                 285
Gly Thr Pro Thr Gln Val Leu Asn Ile Thr Gln Glu Cys Phe Lys Gly
    290                 295                 300
Ile Leu Gln Asp Lys Glu Asn Asp Ile Glu Ala Glu Trp His Asp Glu
305                 310                 315                 320
Ser His Leu Asn Lys Tyr Phe Leu Leu Asn Lys Pro Thr Lys Ile Leu
                325                 330                 335
Ser Pro Glu Tyr Cys Trp Asp Tyr His Ile Gly Met Ser Val Asp Ile
            340                 345                 350
Arg Ile Val Lys Ile Ala Trp Gln Lys Lys Glu Tyr Asn Leu Val Arg
        355                 360                 365
Asn Asn Ile
370

(2) INFORMATION FOR SEQ ID NO: 11:

(i) SEQUENCE CHARACTERISTICS:
        (A) LENGTH: 368 amino acids
        (B) TYPE: amino acid
        (D) TOPOLOGY: linear (ii) MOLECULE TYPE: protein (xi) SEQUENCE DESCRIPTION: SEQ ID NO: 11:

Met Asn Val Lys Gly Lys Val Ile Leu Ser Met Leu Val Val Ser Thr
1               5                   10                  15
Val Ile Val Val Phe Trp Glu Tyr Ile His Ser Pro Glu Gly Ser Leu
            20                  25                  30
Phe Trp Ile Asn Pro Ser Arg Asn Pro Glu Val Gly Gly Ser Ser Ile
        35                  40                  45
Gln Lys Gly Trp Trp Leu Pro Arg Trp Phe Asn Gly Tyr His Glu
50                  55                  60
Glu Asp Gly Asp Ile Asn Glu Glu Lys Glu Gln Arg Asn Glu Asp Glu
65                  70                  75                  80
Ser Lys Leu Lys Leu Ser Asp Trp Phe Asn Pro Phe Lys Arg Pro Glu
                85                  90                  95
Val Val Thr Met Thr Lys Trp Lys Ala Pro Val Val Trp Glu Gly Thr
```

```
                100             105             110
Tyr Asn Arg Ala Val Leu Asp Asn Tyr Tyr Ala Lys Gln Lys Ile Thr
            115                 120                 125
Val Gly Leu Thr Val Phe Ala Val Gly Arg Tyr Ile Glu His Tyr Leu
        130                 135                 140
Glu Glu Phe Leu Thr Ser Ala Asn Lys His Phe Met Val Gly His Pro
145                 150                 155                 160
Val Ile Phe Tyr Ile Met Val Asp Asp Val Ser Arg Met Pro Leu Ile
                165                 170                 175
Glu Leu Gly Pro Leu Arg Ser Phe Lys Val Phe Lys Ile Lys Pro Glu
            180                 185                 190
Lys Arg Trp Gln Asp Ile Ser Met Met Arg Met Lys Thr Ile Gly Glu
        195                 200                 205
His Ile Val Ala His Ile Gln His Glu Val Asp Phe Leu Phe Cys Met
    210                 215                 220
Asp Val Asp Gln Val Phe Gln Asp Lys Phe Gly Val Glu Thr Leu Gly
225                 230                 235                 240
Glu Ser Val Ala Gln Leu Gln Ala Trp Trp Tyr Lys Ala Asp Pro Asn
                245                 250                 255
Asp Phe Thr Tyr Glu Arg Arg Lys Glu Ser Ala Ala Tyr Ile Pro Phe
            260                 265                 270
Gly Glu Gly Asp Phe Tyr Tyr His Ala Ala Ile Phe Gly Gly Thr Pro
        275                 280                 285
Thr Gln Val Leu Asn Ile Thr Gln Glu Cys Phe Lys Gly Ile Leu Lys
    290                 295                 300
Asp Lys Lys Asn Asp Ile Glu Ala Gln Trp His Asp Glu Ser His Leu
305                 310                 315                 320
Asn Lys Tyr Phe Leu Leu Asn Lys Pro Thr Lys Ile Leu Ser Pro Glu
                325                 330                 335
Tyr Cys Trp Asp Tyr His Ile Gly Leu Pro Ala Asp Ile Lys Leu Val
            340                 345                 350
Lys Met Ser Trp Gln Thr Lys Glu Tyr Asn Val Val Arg Asn Asn Val
        355                 360                 365

(2) INFORMATION FOR SEQ ID NO: 12:

(i) SEQUENCE CHARACTERISTICS:
        (A) LENGTH: 371 amino acids
        (B) TYPE: amino acid
        (D) TOPOLOGY: linear (ii) MOLECULE TYPE: protein (xi) SEQUENCE DESCRIPTION: SEQ ID NO: 12:

Met Asn Val Lys Gly Lys Val Ile Leu Leu Met Leu Ile Val Ser Thr
1               5                   10                  15
Val Val Val Val Phe Trp Glu Tyr Val Asn Ser Pro Asp Gly Ser Phe
                20                  25                  30
Leu Trp Ile Tyr His Thr Lys Ile Pro Glu Val Gly Glu Asn Arg Trp
            35                  40                  45
Gln Lys Asp Trp Trp Phe Pro Ser Trp Phe Lys Asn Gly Thr His Ser
        50                  55                  60
Tyr Gln Glu Asp Asn Val Glu Gly Arg Arg Glu Lys Gly Arg Asn Gly
65                  70                  75                  80
Asp Arg Ile Glu Glu Pro Gln Leu Trp Asp Trp Phe Asn Pro Lys Asn
                85                  90                  95
```

```
Arg Pro Asp Val Leu Thr Val Thr Pro Trp Lys Ala Pro Ile Val Trp
            100                 105                 110
Glu Gly Thr Tyr Asp Thr Ala Leu Leu Glu Lys Tyr Tyr Ala Thr Gln
            115                 120                 125
Lys Leu Thr Val Gly Leu Thr Val Phe Ala Val Gly Lys Tyr Ile Glu
            130                 135                 140
His Tyr Leu Glu Asp Phe Leu Glu Ser Ala Asp Met Tyr Phe Met Val
145                 150                 155                 160
Gly His Arg Val Ile Phe Tyr Val Met Ile Asp Asp Thr Ser Arg Met
                165                 170                 175
Pro Val Val His Leu Asn Pro Leu His Ser Leu Gln Val Phe Glu Ile
                180                 185                 190
Arg Ser Glu Lys Arg Trp Gln Asp Ile Ser Met Met Arg Met Lys Thr
            195                 200                 205
Ile Gly Glu His Ile Leu Ala His Ile Gln His Glu Val Asp Phe Leu
            210                 215                 220
Phe Cys Met Asp Val Asp Gln Val Phe Gln Asp Asn Phe Gly Val Glu
225                 230                 235                 240
Thr Leu Gly Gln Leu Val Ala Gln Leu Gln Ala Trp Trp Tyr Lys Ala
                245                 250                 255
Ser Pro Glu Lys Phe Thr Tyr Glu Arg Arg Glu Leu Ser Ala Ala Tyr
            260                 265                 270
Ile Pro Phe Gly Glu Gly Asp Phe Tyr Tyr His Ala Ala Ile Phe Gly
            275                 280                 285
Gly Thr Pro Thr His Ile Leu Asn Leu Thr Arg Glu Cys Phe Lys Gly
            290                 295                 300
Ile Leu Gln Asp Lys Lys His Asp Ile Glu Ala Gln Trp His Asp Glu
305                 310                 315                 320
Ser His Leu Asn Lys Tyr Phe Leu Phe Asn Lys Pro Thr Lys Ile Leu
                325                 330                 335
Ser Pro Glu Tyr Cys Trp Asp Tyr Gln Ile Gly Leu Pro Ser Asp Ile
            340                 345                 350
Lys Ser Val Lys Val Ala Trp Gln Thr Lys Glu Tyr Asn Leu Val Arg
            355                 360                 365
Asn Asn Val
    370

(2) INFORMATION FOR SEQ ID NO: 13:

(i) SEQUENCE CHARACTERISTICS:
        (A) LENGTH: 1340 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

GAGGGCTGCA GGAATTCGAT GATCCCCCAG CTTGAAGTTC CTATTCCGAA GTTCCTATTC      60

TCTAGAAAGT ATAGGAACTT GAAGCTGGGC TGCAGGAATT CGATTCGAGC AGTGTGGTTT     120

TGCAAGAGGA AGCAAAAAGC CTCTCCACCC AGGCCTGGAA TGTTTCCACC CAATGTCGAG     180

CAGTGTGGTT TTGCAAGAGG AAGCAAAAAG CCTCTCCACC CAGGCCTGGA ATGTTTCCAC     240

CCAATGTCGA GCAAACCCCG CCCAGCGTCT TGTCATTGGC GAATTCGAAC ACGCAGATGC     300

AGTCGGGGCG GCGCGGTCCC AGGTCCACTT GGCATATTAA GGTGACGCGT GTGGCCTCGA     360
```

```
ACACCGAGCG ACCCTGCAGC CAATATGGGA TCGGCCATTG AACAAGATGG ATTGCACGCA      420

GGTTCTCCGG CCGCTTGGGT GGAGAGGCTA TTCGGCTATG ACTGGGCACA ACAGACAATC      480

GGCTGCTCTG ATGCCGCCGT GTTCCGGCTG TCAGCGCAGG GGCGCCCGGT TCTTTTTGTC      540

AAGACCGACC TGTCCGGTGC CCTGAATGAA CTCCAAGACG AGGCAGCGCG GCTATCGTGG      600

CTGGCCACGA CGGGCGTTCC TTGCGCAGCT GTGCTCGACG TTGTCACTGA TGCGGGAAGG      660

GACTGGCTGC TATTGGGCGA AGTGCCGGGG CAGGATCTCC TGTCATCTCA CCTTGCTCCT      720

GCCGAGAAAG TATCCATCAT GGCTGATGCA ATGCGGCGGC TGCATACGCT TGATCCGGCT      780

ACCTGCCCAT TCGACCACCA AGCGAAACAT CGCATCGAGC GAGCACGTAC TCGGATGGAA      840

GCCGGTCTTG TCGATCAGGA TGATCTGGAC GAAGAGCATC AGGGGCTCGC GCCAGCCGAA      900

CTGTTCGCCA GGCTCAAGGC GCGGATGCCC GACGGCGAGG ATCTCGTCGT GACCCATGGC      960

GATGCCTGCT TGCCGAATAT CATGGTGGAA AATGGCCGCT TTTCTGGATT CATCGACTGT     1020

GGCCGGCTGG GTGTGGCGGA CCGCTATCAG GACATAGCGT TGGCTACCCG TGATATTGCT     1080

GAAGAGCTTG GCGGCGAATG GGCTGACCGC TTCCTCGTGC TTTACGGTAT CGCCGCTCCC     1140

GATTCGCAGC GCATCGCCTT CTATCGCCTT CTTGACGAGT TCTTCTGAGG GGATCGGCAA     1200

TAAAAAGACA GAATAAAACG CACGGGTGTT GGGCGTTTGT TCGGATCATC AAGCTTGAAG     1260

TTCCTATTCC GAAGTTCCTA TTCTCTAGAA AGTATAGGAA CTTCAAGCTT ATCGATGAGT     1320

AGATCTTGAT CGATACCGTC                                                 1340

(2) INFORMATION FOR SEQ ID NO: 14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

TGCTGGAAAA GTACTACGCC ACACAGAAAC TCA                                    33

(2) INFORMATION FOR SEQ ID NO: 15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

AGCCAGAGTA ATAGTGTCAA GTTTCCATCA CAA                                    33

(2) INFORMATION FOR SEQ ID NO: 16:

(i) SEQUENCE CHARACTERISTICS:
        (A) LENGTH: 36 base pairs
        (B) TYPE: nucleic acid
        (C) STRANDEDNESS: Not Relevant
        (D) TOPOLOGY: linear (ii) MOLECULE TYPE: DNA (xi) SEQUENCE DESCRIPTION: SEQ ID NO: 16:

GCCACACGCG TCACCTTAAT AATATGCCAA GTGGAC                                 36
```

(2) INFORMATION FOR SEQ ID NO: 17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

TCAGCATGAT GCGCATGAAG AC                                        22

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

TGGCCGCGTG GTAGTAAAAA                                           20

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

TCTTGACGAG TTCTTCTGAG                                           20

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

TGGAGATCGC ATTGAAGAGC                                           20

(2) INFORMATION FOR SEQ ID NO: 21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

TGGCCGCGTG GTAGTAAAAA                                           20

(2) INFORMATION FOR SEQ ID NO: 22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

GGGTTTTGGT TTTGATTGTT                                                    20

(2) INFORMATION FOR SEQ ID NO: 23:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

CTGAATTCAT GTTAAACATG GGAGGCCCC                                          29

(2) INFORMATION FOR SEQ ID NO: 24:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

CTGAATTCTG CCCACTCCCT GCCGATG                                            27

(2) INFORMATION FOR SEQ ID NO: 25:

(i) SEQUENCE CHARACTERISTICS:
        (A) LENGTH: 714 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

CTGACACCTT TCGCTTTCCT CTTGCGTGTC CGCCTGCGAC CTTTCCCCAC CCCGGCCTCT         60

TTCCTGGTTG CACCACTTCC TCTCATTCCA AAGGATTGTG CCCTTACTGC TGCTGGTTCT        120

GCACTGGAAA CACGGGGCAG GGAGCCCTCT TCCCATCACC CCTGTAAATG CCACCTGTGC        180

CATACGCCAC CCATGCCACG GCAACCTC ATG AAC CAG ATC AAG AAT CAA CTG           232
                                Met Asn Gln Ile Lys Asn Gln Leu
                                                375

GCA CAG CTC AAT GGC AGC GCC AAT GCT CTC TTC ATT TCC TAT TAC ACA          280
Ala Gln Leu Asn Gly Ser Ala Asn Ala Leu Phe Ile Ser Tyr Tyr Thr
380                 385                 390                 395

GCT CAA GGG GAG CCG TTT CCC AAC AAC GTG GAA AAG CTA TGT GCG CCT          328
Ala Gln Gly Glu Pro Phe Pro Asn Asn Val Glu Lys Leu Cys Ala Pro
                400                 405                 410

AAC ATG ACA GAC TTC CCA TCT TTC CAT GGC AAC GGG ACA GAG AAG ACC          376
Asn Met Thr Asp Phe Pro Ser Phe His Gly Asn Gly Thr Glu Lys Thr
            415                 420                 425

AAG TTG GTG GAG CTG TAT CGG ATG GTC GCA TAC CTG AGC GCC TCC CTG          424
Lys Leu Val Glu Leu Tyr Arg Met Val Ala Tyr Leu Ser Ala Ser Leu

```
                430             435             440
ACC AAT ATC ACC CGG GAC CAG AAG GTC CTG AAC CCC ACT GCC GTG AGC        472
Thr Asn Ile Thr Arg Asp Gln Lys Val Leu Asn Pro Thr Ala Val Ser
        445                 450                 455

CTC CAG GTC AAG CTC AAT GCT ACT ATA GAC GTC ATG AGG GGC CTC CTC        520
Leu Gln Val Lys Leu Asn Ala Thr Ile Asp Val Met Arg Gly Leu Leu
460                 465                 470                 475

AGC AAT GTG CTT TGC CGT CTG TGC AAC AAG TAC CGT GTG GGC CAC GTG        568
Ser Asn Val Leu Cys Arg Leu Cys Asn Lys Tyr Arg Val Gly His Val
                480                 485                 490

GAT GTG CCA CCT GTC CCC GAC CAC TCT GAC AAA GAA GCC TTC CAA AGG        616
Asp Val Pro Pro Val Pro Asp His Ser Asp Lys Glu Ala Phe Gln Arg
            495                 500                 505

AAA AAG TTG GGT TGC CAG CTT CTG GGG ACA TAC AAG CAA GTC ATA AGT        664
Lys Lys Leu Gly Cys Gln Leu Leu Gly Thr Tyr Lys Gln Val Ile Ser
                510                 515                 520

GTG GTG GTC CAG GCC TTC T AGAGAGGAGG TCTTGAATGT ACCATGGACT              713
Val Val Val Gln Ala Phe
    525

G                                                                      714
```

(2) INFORMATION FOR SEQ ID NO: 26:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO: 26:

```
Met Asn Gln Ile Lys Asn Gln Leu Ala Gln Leu Asn Gly Ser Ala Asn
1               5                   10                  15

Ala Leu Phe Ile Ser Tyr Tyr Thr Ala Gln Gly Glu Pro Phe Pro Asn
                20                  25                  30

Asn Val Glu Lys Leu Cys Ala Pro Asn Met Thr Asp Phe Pro Ser Phe
            35                  40                  45

His Gly Asn Gly Thr Glu Lys Thr Lys Leu Val Glu Leu Tyr Arg Met
        50                  55                  60

Val Ala Tyr Leu Ser Ala Ser Leu Thr Asn Ile Thr Arg Asp Gln Lys
65                  70                  75                  80

Val Leu Asn Pro Thr Ala Val Ser Leu Gln Val Lys Leu Asn Ala Thr
                85                  90                  95

Ile Asp Val Met Arg Gly Leu Leu Ser Asn Val Leu Cys Arg Leu Cys
                100                 105                 110

Asn Lys Tyr Arg Val Gly His Val Asp Val Pro Pro Val Pro Asp His
            115                 120                 125

Ser Asp Lys Glu Ala Phe Gln Arg Lys Lys Leu Gly Cys Gln Leu Leu
        130                 135                 140

Gly Thr Tyr Lys Gln Val Ile Ser Val Val Val Gln Ala Phe
145                 150                 155
```

(2) INFORMATION FOR SEQ ID NO: 27:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 27:

ACACGGTACT TGTTGCA                                                        17

(2) INFORMATION FOR SEQ ID NO: 28:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 28:

TTCTGGTCCC GGGTGATATT GGTCA                                               25

(2) INFORMATION FOR SEQ ID NO: 29:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: nucleic acid (xi) SEQUENCE DESCRIPTION: SEQ ID NO: 29:

CCATGGCCTC GAGGGCCCCC CCCCCCCCC                                           29

(2) INFORMATION FOR SEQ ID NO: 30:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 30:

CACCTTTCGC TTTCCT                                                         16

(2) INFORMATION FOR SEQ ID NO: 31:

(i) SEQUENCE CHARACTERISTICS:
            (A) LENGTH: 655 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 31:

GACCTTTTGC CTTTTCTCTC TCCTGGTGCA CCATTTCCTC TCCCTCCCTG AGCCGGAGTT         60

GTGCCCCTGC TGTTGGTTCT GCACTGGAAA CATGGGGCGG GGAGCCCCCT CCCCATCACC        120

CCTGTCAACG CCACCTGTGC CATACGCCAC CCATGTCACA ACAACCTC ATG AAC CAG        177
                                                    Met Asn Gln
                                                          160

ATC AGG AGC CAA CTG GCA CAG CTC AAT GGC AGT GCC AAT GCC CTC TTT         225
Ile Arg Ser Gln Leu Ala Gln Leu Asn Gly Ser Ala Asn Ala Leu Phe
        165                 170                 175

ATT CTC TAT TAC ACA GCC CAG GGG GAG CCG TTC CCC AAC AAC CTG GAC         273
Ile Leu Tyr Tyr Thr Ala Gln Gly Glu Pro Phe Pro Asn Asn Leu Asp
        180                 185                 190

```
AAG CTA TGT GGC CCC AAC GTG ACG GAC TTC CCG CCC TTC CAC GCC AAC      321
Lys Leu Cys Gly Pro Asn Val Thr Asp Phe Pro Pro Phe His Ala Asn
195                 200                 205

GGC ACG GAG AAG GCC AAG CTG GTG GAG CTG TAC CGC ATA GTC GTG TAC      369
Gly Thr Glu Lys Ala Lys Leu Val Glu Leu Tyr Arg Ile Val Val Tyr
210                 215                 220                 225

CTT GGC ACC TCC CTG GGC AAC ATC ACC CGG GAC CAG AAG ATC CTC AAC      417
Leu Gly Thr Ser Leu Gly Asn Ile Thr Arg Asp Gln Lys Ile Leu Asn
            230                 235                 240

CCC AGT GCC CTC AGC CTC CAC AGC AAG CTC AAC GCC ACC GCC GAC ATC      465
Pro Ser Ala Leu Ser Leu His Ser Lys Leu Asn Ala Thr Ala Asp Ile
                245                 250                 255

CTG CGA GGC CTC CTT AGC AAC GTG CTG TGC CGC CTG TGC AGC AAG TAC      513
Leu Arg Gly Leu Leu Ser Asn Val Leu Cys Arg Leu Cys Ser Lys Tyr
        260                 265                 270

CAC GTG GGC CAT GTG GAC GTG ACC TAC GGC CCT GAC ACC TCG GGT AAG      561
His Val Gly His Val Asp Val Thr Tyr Gly Pro Asp Thr Ser Gly Lys
    275                 280                 285

GAT GTC TTC CAG AAG AAG AAG CTG GGC TGT CAA CTC CTG GGG AAG TAT      609
Asp Val Phe Gln Lys Lys Lys Leu Gly Cys Gln Leu Leu Gly Lys Tyr
290                 295                 300                 305

AAG CAG ATC ATC GCC GTG TTG GCC CAG GCC TTC T AGCAGGAGGT             653
Lys Gln Ile Ile Ala Val Leu Ala Gln Ala Phe
                310                 315

CT                                                                    655

(2) INFORMATION FOR SEQ ID NO: 32:

(i) SEQUENCE CHARACTERISTICS:
        (A) LENGTH: 158 amino acids
        (B) TYPE: amino acid
        (C) STRANDEDNESS: single
        (D) TOPOLOGY: linear (ii) MOLECULE TYPE: <Unknown>

(xi) SEQUENCE DESCRIPTION: SEQ ID NO: 32:

Met Asn Gln Ile Arg Ser Gln Leu Ala Gln Leu Asn Gly Ser Ala Asn
1               5                   10                  15

Ala Leu Phe Ile Leu Tyr Tyr Thr Ala Gln Gly Glu Pro Phe Pro Asn
            20                  25                  30

Asn Leu Asp Lys Leu Cys Gly Pro Asn Val Thr Asp Phe Pro Pro Phe
            35                  40                  45

His Ala Asn Gly Thr Glu Lys Ala Lys Leu Val Glu Leu Tyr Arg Ile
    50                  55                  60

Val Val Tyr Leu Gly Thr Ser Leu Gly Asn Ile Thr Arg Asp Gln Lys
65                  70                  75                  80

Ile Leu Asn Pro Ser Ala Leu Ser Leu His Ser Lys Leu Asn Ala Thr
                85                  90                  95

Ala Asp Ile Leu Arg Gly Leu Leu Ser Asn Val Leu Cys Arg Leu Cys
                100                 105                 110

Ser Lys Tyr His Val Gly His Val Asp Val Thr Tyr Gly Pro Asp Thr
            115                 120                 125

Ser Gly Lys Asp Val Phe Gln Lys Lys Lys Leu Gly Cys Gln Leu Leu
        130                 135                 140

Gly Lys Tyr Lys Gln Ile Ile Ala Val Leu Ala Gln Ala Phe
145                 150                 155
```

```
(2) INFORMATION FOR SEQ ID NO: 33:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 33:

CTGTTGGTTC TGCACTGGA                                                   19
```